(12) United States Patent
Otake et al.

(10) Patent No.: US 7,687,514 B2
(45) Date of Patent: Mar. 30, 2010

(54) BENZIMIDAZOLE DERIVATIVES

(75) Inventors: Norikazu Otake, Tsukuba (JP); Minoru Moriya, Tsukuba (JP); Yoshio Ogino, Tsukuba (JP); Kenji Matsuda, Tokyo (JP); Yoshikazu Nagae, Tsukuba (JP); Akio Kanatani, Tsukuba (JP); Takehiro Fukami, Tsukuba (JP)

(73) Assignee: Banyu Pharmaceuticals Co., Ltd., Tokyo (JP)

( * ) Notice: Subject to any disclaimer, the term of this patent is extended or adjusted under 35 U.S.C. 154(b) by 502 days.

(21) Appl. No.: 11/431,274

(22) Filed: May 10, 2006

(65) Prior Publication Data

US 2006/0205750 A1      Sep. 14, 2006

Related U.S. Application Data

(62) Division of application No. 10/463,390, filed on Jun. 18, 2003, now Pat. No. 7,105,526.

(30) Foreign Application Priority Data

Jun. 28, 2002   (JP) .............................. 2002-190978

(51) Int. Cl.
*A61K 31/4747*   (2006.01)
*C07D 221/20*   (2006.01)

(52) U.S. Cl. ........................ 514/278; 514/394; 546/16; 548/300.7

(58) Field of Classification Search ........................ None
See application file for complete search history.

(56) References Cited

U.S. PATENT DOCUMENTS

| | | | |
|---|---|---|---|
| 6,326,375 B1 | 12/2001 | Fukami et al. | |
| 6,566,367 B2 | 5/2003 | Bakthavatchalam et al. | |
| 7,365,079 B2 * | 4/2008 | Otake et al. | 514/278 |

FOREIGN PATENT DOCUMENTS

| | | |
|---|---|---|
| WO | WO 00/27845 | 5/2000 |
| WO | WO 01/14376 | 3/2001 |
| WO | WO 02/48152 | 6/2002 |

* cited by examiner

*Primary Examiner*—Kamal A Saeed
(74) *Attorney, Agent, or Firm*—Baerbel R. Brown; Catherine D. Fitch

(57) ABSTRACT

The present invention relates to a compound of the formula (I):

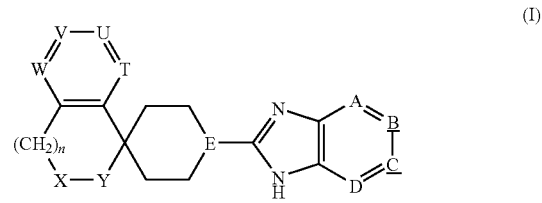

(wherein A, B, C and D are independently nitrogen or optionally substituted methine; E is nitrogen, methine or hydroxy substituted methine; n is 0 or 1; T, U, V and W are independently nitrogen or optionally substituted methine; X is —N($SO_2R^4$)—, —N($COR^5$)— or —CO—; Y is —C($R^6$)($R^7$)—, —O— or —N($R^8$)—, provided that the compound (I) when E is nitrogen, n is 0, X is —CO—, and Y is —O— is excluded) and the like, which are useful as an agent for the treatment of various diseases related to NPY.

20 Claims, No Drawings

BENZIMIDAZOLE DERIVATIVES

CROSS-REFERENCE TO RELATED APPLICATIONS

This application is a divisional application of U.S. Ser. No. 10/463,390, filed Jun. 18, 2003, now U.S. Pat. No. 7,105,526 a U.S. Application which claims priority under 35 U.S.C. §119 from Japanese Application No. JP2002-0190978, filed Jun. 28, 2002.

TECHNICAL FIELD

The present invention is useful in medical fields. In more detail, novel benzimidazole derivatives of the present invention have an effect as neuropeptide Y receptor antagonists and are useful as agents for the treatment of various kinds of cardiovascular disorders, central nervous system disorders, metabolic diseases and the like.

BACKGROUND ART

Neuropeptide Y (hereinafter referred to as NPY), a peptide consisting of 36 amino acids, was first isolated from porcine brain by Tatemoto et al in 1982 (NATURE, vol. 296, p. 659(1982)). NPY is widely distributed in central nervous system and peripheral nervous system, and plays various roles as one of the most abundant peptides in the nervous system. That is, NPY acts as an orexigenic substance in the central nervous system and markedly promotes fat accumulation via the mediation of secretion of various hormones or the action of the nervous system. It is known that continuous intracerebroventricular administration of NPY induces obesity and insulin resistance due to these actions (INTERNATIONAL JOURNAL OF OBESITY, vol. 19, p. 517(1995); Endocrinology, vol. 133, p. 1753(1993)). It is also known that NPY has central actions such as depression, anxiety, schizophrenia, pain, dementia, circadian rhythm control and the like (DRUGS, vol. 52, p. 371(1996); THE JOURNAL OF NEUROSCIENCE, vol. 18, p. 3014(1998)). Furthermore, in the periphery, NPY coexists with norepinephrine in sympathetic-nerve terminals and is related to the tonicity of the sympathetic nervous system. It is known that peripheral administration of NPY causes vasoconstriction and enhances the activities of other vasoconstrictive substances such as norepinephrine (BRITISH JOURNAL OF PHARMACOLOGY, vol. 95, p. 419(1988)). It is also reported that NPY could participate in the development of cardiac hypertrophy as a result of the sympathetic stimulation (PROCEEDING NATIONAL ACADEMIC SCIENCE USA, vol. 97, p. 1595 (2000)).

On the other hand, it is reported that NPY is also involved in the secretory function of sexual hormones and growth hormone, sexual behavior and reproductive function, gastro-intestinal motility, bronchoconstriction, inflammation and alcohol preference (LIFE SCIENCE, vol. 55, p. 551(1994); THE JOURNAL OF ALLERGY AND IMMUNOLOGY, vol. 101, p. S345(1998); NATURE, vol. 396, p. 366(1998)).

NPY has a variety of pharmacological effects resulting from NPY binding to the NPY receptors, to some of which other NPY related peptides including peptide YY and pancreatic polypeptide also bind. It is known that these pharmacological effects of NPY are mediated by the action of at least five receptors with or without synergistic interactions (TRENDS IN NEUROSCIENCE, vol. 20, p. 294(1997)).

It is reported that the central effects mediated by NPY Y1 receptor include remarkable orexigenic effect (ENDOCRINOLOGY, vol. 137, p. 3177(1996); ENDOCRINOLOGY, vol. 141, p. 1011(2000)). Further, NPY Y1 receptor is reported to be involved in anxiety and pain (NATURE, vol. 259, p. 528(1993); BRAIN RESEARCH, vol. 859, p. 361 (2000). In addition, the pressor effect mediated by the strong vasoconstrictor action in the periphery is also reported (FEBS LETTERS, vol. 362, p. 192(1995); NATURE MEDICINE, vol. 4, p. 722(1998)).

It is known that the effects mediated by NPY Y2 receptor include an inhibitory effect on the release of various neurotransmitters in the sympathetic nerve endings (BRITISH JOURNAL OF PHARMACOLOGY, vol. 102, p. 41(1991); SYNAPSE, vol. 2, p. 299(1988)). In periphery, NPY Y2 causes constriction of blood vessel or vas deferens directly or via the control of release of various neurotransmitters (THE JOURNAL OF PHARMACOLOGY AND EXPERIMENTAL THERAPEUTICS, vol. 261, p. 863(1992); BRITISH JOURNAL OF PHARMACOLOGY, vol. 100, p. 190(1990)). Inhibition of lipolysis in adipose tissues is also known (ENDOCRINOLOGY, vol. 131, p. 1970(1992)). Further, inhibition of ion secretion in the gastro-intestinal tract is reported (BRITISH JOURNAL OF PHARMACOLOGY, vol. 101, p. 247(1990)). On the other hand, the effect on the central nervous system functions such as memory, anxiety and the like are also known. (BRAIN RESEARCH, vol. 503, p. 73(1989); PEPTIDES, vol. 19, p. 359(1998)).

It is reported that NPY Y3 receptor exists mainly in brainstem and heart and is related to the regulation of blood pressure and heart rate (THE JOURNAL OF PHARMACOLOGY AND EXPERIMENTAL THERAPEUTICS, vol. 258, p. 633(1991); PEPTIDES, vol. 11, p. 545(1990)). It is also known that NPY Y3 is involved in the control of catecholamine secretion in adrenal gland (THE JOURNAL OF PHARMACOLOGY AND EXPERIMENTAL THERAPEUTICS, vol. 244, p. 468(1988); LIFE SCIENCE, vol. 50, p. PL7 (1992)).

NPY Y4 receptor has high affinity for pancreatic polypeptide in particular. As for the pharmacological effects of NPY Y4, inhibition of pancreatic exocrine secretion and gastrointestinal motility is reported (GASTROENTEROLOGY, vol. 85, p. 1411(1983)). Further, it is reported that NPY enhances the secretion of sexual hormones in the central nervous system (ENDOCRINOLOGY, vol. 140, p. 5171(1999)).

As for the effects mediated by NPY Y5 receptor, fat accumulation effects including orexigenic effect are prominent (NATURE, vol. 382, p. 168(1996); AMERICAN JOURNAL OF PHYSIOLOGY, vol. 277, p. R1428(1999)). It is also reported that the NPY Y5 receptor mediates some CNS effects, such as seizure and epilepsy, or pain and morphine withdrawal symptoms, and the control of circadian rhythm (NATURE MEDICINE, vol. 3, p. 761(1997); PROCEEDING NATIONAL ACADEMIC SCIENCE USA, vol. 96, p. 13518(1999); THE JOURNAL OF PHARMACOLOGY AND EXPERIMENTAL THERAPEUTICS, vol. 284, p. 633 (1998); THE JOURNAL OF NEUROSCIENCE, vol. 21, p. 5367(2001). In addition, diuresis effect and hypoglicemic effect in the periphery are reported (BRITISH JOURNAL OF PHARMACOLOGY, vol. 120, p. 1335(1998); ENDOCRINOLOGY, vol. 139, p. 3018(1998)). NPY is also reported to enhance cardiac hypertrophy as a result of the sympathetic accentuation (PROCEEDING NATIONAL ACADEMIC SCIENCE USA, vol. 97, p. 1595 (2000)).

The effects of NPY are expressed when NPY binds to the NPY receptors in the central or peripheral nervous system. Therefore, the action of NPY can be prevented by blocking its binding to NPY receptors. For this reason, it is expected that substances antagonize NPY binding to NPY receptors may be useful for the prophylaxis or treatment of various diseases related to NPY, for example cardiovascular disorders such as angina, acute or congestive heart failure, myocardial infarction, hypertension, nephropathy, electrolyte abnormality, vasospasm, atherosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, gout, fatty liver, etc., genital or reproductive disorders such as infertility, preterm labor, sexual dysfunction, etc., gastro-intestinal disorders, respiratory disorder, inflammatory diseases or glaucoma, and the like. (TRENDS IN PHARMACOLOGICAL SCIENCE, vol. 15, p. 153(1994); LIFE SCIENCE, vol. 55, p. 551(1994); DRUGS, vol. 52, p. 371(1996); THE JOURNAL OF ALLERGY AND IMMUNOLOGY, vol. 101, p. S345 (1998); NATURE, vol. 396, p. 366(1998); THE JOURNAL OF PHARMACOLOGY AND EXPERIMENTAL THERAPEUTICS, vol. 284, p. 633(1998); TRENDS IN PHARMACOLOGICAL SCIENCE, vol. 20, p. 104(1999); PROCEEDING NATIONAL ACADEMIC SCIENCE USA, vol. 97, p. 1595(2000); THE JOURNAL OF NEUROSCIENCE, vol. 21, p. 5367(2001); PHARMACOLOGY & THERAPEUTICS, vol. 65, p. 397(1995)).

It was recently found that, as a result of the study by the present inventors, a certain NPY receptor antagonist is useful for the prophylaxis or treatment of hypercholesterolemia, hyperlipidemia and arteriosclerosis (International application publication WO99/27965).

International application publication WO00/27845 and WO01/14376 disclose a variety of carboxamide derivatives, and mention that said derivatives have excellent NPY receptor antagonistic activities. International application publication WO02/48152 discloses a variety of spiro(isobenzofuran-1,4'-piperidine)-3-on derivatives, and mentions that said derivatives have an effect to regulate the NPY binding to NPY5 receptors. However, none of the above international publications describes the compounds of the present invention.

DISCLOSURE OF INVENTION

The object of the present invention is to provide novel medicines which exhibit NPY antagonistic activities.

The present inventors have discovered that the compounds of the general formula (I):

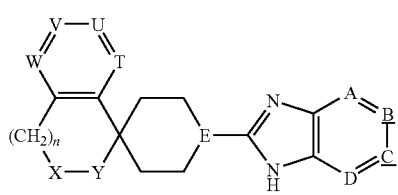

(I)

(wherein A, B, C and D are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and —Q$^1$—Ar$^1$, and at least one of A, B, C and D is said methine group;

Ar$^1$ is aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —Q$^2$—Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

E is nitrogen, methine or hydroxy substituted methine (namely methine substituted by hydroxy);

n is 0 or 1;

Q$^1$ and Q$^2$ are independently a single bond, oxygen, carbonyl or —N(R$^3$)—;

R$^1$ and R$^2$ are independently hydrogen or lower alkyl, or R$^1$ and R$^2$, taken together, form lower alkylene which may be intervened by oxygen, sulfur or imino;

R$^3$ is hydrogen or lower alkyl;

R$^4$ is lower alkyl, aralkyl or aryl;

R$^5$ and R$^8$ are independently hydrogen, lower alkyl, aralkyl or aryl;

R$^6$ and R$^7$ are independently hydrogen, hydroxy, lower alkyl, aralkyl or aryl;

T, U, V and W are independently methine or nitrogen, said methine being optionally substituted by a substituent selected from the group consisting of halogen, lower alkyl, halo-lower alkyl, hydroxy, lower alkoxy and halo-lower alkoxy, and at least two of T, U, V and W are said methine group;

X is —N(SO$_2$R$^4$)—, —N(COR$^5$)— or —CO—;

Y is —C(R$^6$)(R$^7$)—, —O— or —N(R$^8$)—, provided that the compound (I) when E is nitrogen, n is 0, X is —CO— and Y is —O— is excluded)

exhibit NPY antagonistic activities especially on NPY Y5 receptors and show excellent pharmacokinetics such as transport into brain or transport to cerebrospinal fluid, etc., thereby completed the present invention.

Compounds of the present invention (I) exhibit NPY antagonistic effects especially on NPY Y5 receptors and show excellent pharmacokinetics such as transport into brain or transport to cerebrospinal fluid, etc. Also, the compound of the present invention (I) are useful as agents for the treatment of various diseases related to NPY, for example, cardiovascular disorders such as angina, acute or congestive heart failure, myocardial infarction, hypertension, nephropathy, electrolyte abnormality, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipidemia, gout, fatty liver, etc., genital or reproductive disorders such as infertility, preterm labor, sexual dysfunction, etc., gastro-intestinal disorders, respiratory disorder, inflammatory diseases or glaucoma, and the like, also for example, atherosclerosis, hypogonadism, hyperandrogenism, polycystic ovary syndrome, hirsutism, gastro-intestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, gallbladder diseases, cancer (breast, endometrial, colon), breathlessness, hyperuricemia, impaired fertility, low back pain, or increased anesthetic risk, and the like.

The compounds of the present invention (I) are particularly useful as agents for the treatment of bulimia, obesity, diabetes and the like.

The present invention relates to the compounds represented by the general formula (I), or the salts thereof, and the production method and the use thereof.

The means of terms used in the present specification are defined and more detailed description of this invention is described in the following.

"Halogen" refers to fluorine, chlorine, bromine and iodine.

"Lower alkyl" refers to a straight- or branched-chain alkyl group of C1 to C6, and its examples are methyl, ethyl, propyl, isopropyl, butyl, isobutyl, sec-butyl, tert-butyl, pentyl, isopentyl, hexyl, isohexyl and the like.

"Halo-lower alkyl" refers to said lower alkyl substituted with identically or differently one, two or more, preferably one to three said halogen at the substitutable, arbitrary position(s), and its examples are fluoromethyl, difluoromethyl, trifluoromethyl, 2-fluoroethyl, 1,2-difluoroethyl, chloromethyl, 2-chloroethyl, 1,2-dichloroethyl, bromomethyl, iodomethyl and the like.

"Lower alkoxy" refers to straight- or branched-chain alkoxy of C1 to C6 and its examples are methoxy, ethoxy, propoxy, isopropoxy, butoxy, sec-butoxy, isobutoxy, tert-butoxy, pentyloxy, isopentyloxy, hexyloxy, isohexyloxy and the like.

"Halo-lower alkoxy" refers to said lower alkoxy substituted with identically or differently one, two or more, preferably one to three said halogen at substitutable, arbitrary position(s), and its examples are fluoromethoxy, difluoromethoxy, trifluoromethoxy, 2-fluoroethoxy, 1,2-difluoroethoxy, chloromethoxy, 2-chloroethoxy, 1,2-dichloroethoxy, bromomethoxy, iodomethoxy and the like.

"Lower alkoxycarbonyl" refers to an alkoxycarbonyl group containing said lower alkoxy, that is, an alkoxycarbonyl group of C2 to C7, and its examples are methoxycarbonyl, ethoxycarbonyl, propoxycarbonyl, isopropoxycarbonyl, butoxycarbonyl, isobutoxycarbonyl, tert-butoxycarbonyl, pentyloxycarbonyl and the like.

"Lower alkylsulfonyl" refers to a straight- or branched-chain alkylsulfonyl group of C1 to C6, and its examples are methylsulfonyl, ethylsulfonyl, propylsulfonyl, isopropylsulfonyl, butylsulfonyl, sec-butylsulfonyl, isobutylsulfonyl, tert-butylsulfonyl, pentylsulfonyl, isopentylsulfonyl, hexylsulfonyl, isohexylsulfonyl and the like.

"Lower alkylsulfonyloxy" refers to a straight- or branched-chain alkylsulfonyloxy group of C1 to C6, and its examples are methylsulfonyloxy, ethylsulfonyloxy, propylsulfonyloxy, isopropylsulfonyloxy, butylsulfonyloxy, sec-butylsulfonyloxy, isobutylsulfonyloxy, tert-butylsulfonyloxy, pentylsulfonyloxy, isopentylsulfonyloxy, hexylsulfonyloxy, isohexylsulfonyloxy and the like.

"Hydroxy-lower alkyl" refers to said lower alkyl substituted with one, two or more, preferably one or two hydroxy at substitutable, arbitrary position(s), and its examples are hydroxymethyl, 2-hydroxyethyl, 1-hydroxy-1-methylethyl, 1,2-dihydroxyethyl, 3-hydroxypropyl and the like.

"Cyclo-lower alkyl" refers to a cycloalkyl group of C3 to C6, and its examples are cyclopropyl, cyclobutyl, cyclopentyl, cyclohexyl and the like.

"Lower alkenyl" refers to a straight- or branched-chain alkenyl group of C2 to C6, and its examples are vinyl, 1-propenyl, 2-propenyl, isopropenyl, 3-butenyl, 2-butenyl, 1-butenyl, 1-methyl-2-propenyl, 1-methyl-1-propenyl, 1-ethyl-1-ethenyl, 2-methyl-2-propenyl, 2-methyl-1-propenyl, 3-methyl-2-butenyl, 4-pentenyl and the like.

"Lower alkylthio" refers to straight- or branched-chain alkylthio of C1 to C6, and its examples are methylthio, ethylthio, propylthio, isopropylthio, butylthio, sec-butylthio, isobutylthio, tert-butylthio, pentylthio, isopentylthio, hexylthio, isohexylthio and the like.

"Lower alkanoyl" refers to an alkanoyl group containing said lower alkyl, that is, an alkanoyl group of C2 to C7, and its examples are acetyl, propionyl, butyryl, isobutyryl, valeryl, isovaleryl, pivaloyl and the like.

"Lower alkanoylamino" refers to an amino group mono-substituted with said lower alkanoyl, and its examples are acetylamino, propionylamino, butyrylamino, isobutyrylamino, valerylamino, isovalerylamino, pivaloylamino and the like.

"Aryl" refers to phenyl, naphthyl and the like.

"Heteroaryl" refers to 5- or 6-membered monocyclic heteroaromatic group which contains one, two or more, preferably one to three hetero atom(s) identically or differently selected from the group consisting of oxygen, nitrogen and sulfur; or condensed cyclic heteroaromatic group, where said monocyclic heteroaromatic group is condensed with said aryl group or condensed each other with the same or different said monocyclic heteroaromatic group, and its examples are payroll, furyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzofuranyl, benzothienyl, benzoimidazolyl, benzoxazolyl, benzoisoxazolyl, benzothiazolyl, benzoisothiazolyl, indazolyl, purinyl, quinolyl, isoquinolyl, phthalazinyl, naphthylidinyl, quinoxalinyl, quinazolinyl, cinnolinyl, pteridinyl, pyrido[3,2-b]pyridyl and the like.

"Lower alkylamino" refers to an amino group mono-substituted with said lower alkyl, and its examples are methylamino, ethylamino, propylamino, isopropylamino, butylamino, sec-butylamino, tert-butylamino and the like.

"Di-lower alkylamino" refers to an amino group di-substituted with the same or different said lower alkyl, and its examples are dimethylamino, diethylamino, ethylmethylamino, dipropylamino, methylpropylamino, diisopropylamino and the like.

"Lower alkylene which may be intervened by oxygen, sulfur or imino" refers to an alkylene group of C2 to C5, which is not intervened or intervened by one, two or more, preferably one oxygen, sulfur or imino at optional and intervention capable position(s) of said alkylene chain, and its examples are ethylene, trimethylene, tetramethylene, pentamethylene, 2-oxatetramethylene, 2-oxapentamethylene, 3-oxapentamethylene, 2-thiatetramethylene, 2-thiapentamethylene, 3-thiapentamethylene, 2-azatetramethylene, 2-azapentamethylene, 3-azapentamethylene and the like.

"Aralkyl" refers to said lower alkyl substituted with one, two or more, preferably one said aryl at substitutable, arbitrary position(s), and its examples are benzyl, 1-phenylethyl, phenethyl, 1-naphthylmethyl, 2-naphthylmethyl and the like.

The esters of compounds of formula (I) refer to, for example, the pharmaceutically acceptable, common esters of said carboxyl group when the compound has a carboxyl group, and examples thereof are esters with lower alkyl (e.g. methyl, ethyl, propyl, isopropyl, butyl, sec-butyl, tert-butyl, pentyl, isopentyl, neopentyl, cyclopropyl, cyclobutyl, cyclopentyl), esters with aralkyl (e.g. benzyl, phenethyl), esters with lower alkenyl (e.g. allyl, 2-butenyl), esters with lower-alkoxy-lower-alkyl (e.g. methoxymethyl, 2-methoxyethyl, 2-ethoxyethyl), esters with lower-alkanoyloxy-lower-alkyl (e.g. acetoxymethyl, pivaloyloxymethyl, 1-pivaloyloxyethyl), esters with lower-alkoxycarbonyl-lower-alkyl (e.g. methoxycarbonylmethyl, isopropoxycarbonylmethyl), esters with carboxy-lower alkyl (e.g. carboxymethyl), esters with lower-alkoxycarbonyloxy-lower-alkyl (e.g. 1-(ethoxycarbonyloxy)ethyl, 1-(cyclohexyloxycarbonyloxy)ethyl), esters with carbamoyloxy-lower alkyl (e.g. carbamoyloxymethyl), esters with phthalidyl, esters with (5-substituted-2-oxo-1,3-dioxol-4-yl)methyl (e.g. (5-methyl-2-oxo-1,3-dioxol-4-yl)methyl) and the like.

The salts of compounds of formula (I) refer to the pharmaceutically acceptable, common salts, and examples thereof are base addition salt to said carboxyl group when the compound has a carboxyl group, or acid addition salt to said amino or basic heterocyclyl when the compound has an amino or basic heterocyclyl group and the like.

Said base addition salts include salts with alkali metals (e.g. sodium, potassium); salts with alkaline earth metals (e.g. calcium, magnesium); ammonium salts; salts with organic amines (e.g. trimethylamine, triethylamine, dicyclohexylamine, ethanolamine, diethanolamine, triethanolamine, procaine, N,N'-dibenzylethylenediamine) and the like.

Said acid addition salts include salts with inorganic acids (e.g. hydrochloric acid, sulfuric acid, nitric acid, phosphoric acid, perchloric acid), salts with organic acids (e.g. maleic acid, fumaric acid, tartaric acid, citric acid, ascorbic acid, trifluoroacetic acid), salts with sulfonic acids (e.g. methanesulfonic acid, isethionic acid, benzenesulfonic acid, p-toluenesulfonic acid) and the like.

An N-oxide derivative of the compound represented by the formula (I) means a compound of which any one or more than one nitrogen atoms present in the compound of the formula (I) is or are oxidized to form an N-oxide or N-oxides, and such an N-oxide derivative includes, for example, a compound of which nitrogen atom is oxidized in case when T, U, V or/and W in the formula (I) is or are nitrogen.

"An agent for treatment" refers to a medicament which is employed for the treatment and/or prophylaxis of various diseases.

In order to disclose the aforesaid compounds of the general formula (I) of the present invention more specifically, the various symbols used in the formula (I) are explained in more detail by presenting preferred embodiments.

A, B, C and D are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and —$Q^1$—$Ar^1$, and at least one of A, B, C and D is said methine group.

"Methine which is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and —$Q^1$—$Ar^1$" refers to unsubstituted methine or methine having a substituent, wherein said substituent may be selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and —$Q^1$—$Ar^1$.

Halogen as said substituent preferably includes fluorine, chlorine and the like.

Lower alkyl as said substituent preferably includes methyl, ethyl and the like.

Halo-lower alkyl as said substituent preferably includes difluoromethyl, trifluoromethyl and the like.

Lower alkoxy as said substituent preferably includes methoxy, ethoxy and the like.

Halo-lower alkoxy as said substituent preferably includes difluoromethoxy, trifluoromethoxy and the like.

Lower alkoxycarbonyl as said substituent preferably includes methoxycarbonyl, ethoxycarbonyl and the like.

Lower alkylsulfonyl as said substituent preferably includes methylsulfonyl, ethylsulfonyl and the like.

Lower alkylsulfonyloxy as said substituent preferably includes methylsulfonyloxy, ethylsulfonyloxy and the like.

In a group of formula: —N($R^1$)$R^2$ as said substituent, $R^1$ and $R^2$ are independently hydrogen or lower alkyl, or $R^1$ and $R^2$, taken together, form lower alkylene which may be intervened by oxygen, sulfur or imino.

Lower alkyl as $R^1$ or $R^2$ preferably includes methyl, ethyl, propyl and the like.

"Lower alkylene which may be intervened by oxygen, sulfur or imino" formed by taking $R^1$ and $R^2$ together preferably includes pentamethylene, 3-oxapentamethylene and the like, and it, together with nitrogen next thereto, forms piperidino, morpholino, etc.

The preferred embodiment of $R^1$ and $R^2$ includes the case where at least one of $R^1$ or $R^2$ is lower alkyl, or the case where $R^1$ and $R^2$, taken together, form lower alkylene which may be intervened by oxygen, sulfur or imino.

Thus, a group of formula: —N($R^1$)$R^2$ includes, for example, amino, methylamino, ethylamino, propylamino, dimethylamino, diethylamino, ethylmethylamino, 1-azetidinyl, 1-pyrrolidinyl, piperidino, morpholino, thiomorpholino, 1-piperazinyl and the like, among which the preferred are methylamino, dimethylamino, piperidino, morpholino and the like.

In a group of formula: —$Q^1$—$Ar^1$ as said substituent, $Ar^1$ is aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —$Q^2$—$Ar^2$; $Q^1$ is a single bond, oxygen, carbonyl or —N($R^3$)—.

"Aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsufonyl, carboxyl, lower alkanoyl, lower alkoxycarbonyl, lower alkanoylamino and —$Q^2$—$Ar^2$" refers to unsubstituted said aryl or said heteroaryl, or said aryl or said heteroaryl having substituent(s) at the substitutable, arbitrary position(s) wherein said substituent(s) may be one, two or more, preferably one or two member(s) identically or differently selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsufonyl, carboxyl, lower alkanoyl, lower alkoxycarbonyl, lower alkanoylamino and —$Q^2$—$Ar^2$.

Halogen as said substituent preferably includes fluorine, chlorine, bromine and the like.

Lower alkyl as said substituent preferably includes methyl, ethyl, propyl, isopropyl and the like.

Halo-lower alkyl as said substituent preferably includes difluoromethyl, trifluoromethyl and the like.

Hydroxy-lower alkyl as said substituent preferably includes hydroxymethyl, 2-hydroxyethyl, 1-hydroxy-1-methylethyl and the like.

Cyclo-lower alkyl as said substituent preferably includes cyclopropyl, cyclobutyl and the like.

Lower alkenyl as said substituent preferably includes vinyl, 1-propenyl, 2-methyl-1-propenyl and the like.

Lower alkoxy as said substituent preferably includes methoxy, ethoxy and the like.

Halo-lower alkoxy as said substituent preferably includes fluoromethoxy, difluoromethoxy, trifluoromethoxy and the like.

Lower alkylthio as said substituent preferably includes methylthio, ethylthio and the like.

Lower alkylsulfonyl as said substituent preferably includes methylsulfonyl, ethylsulfonyl, propylsulfonyl and the like.

Lower alkanoyl as said substituent preferably includes acetyl, propionyl and the like.

Lower alkoxycarbonyl as said substituent preferably includes methoxycarbonyl, ethoxycarbonyl and the like.

Lower alkanoylamino as said substituent preferably includes acetylamino, propanoylamino and the like.

In a group of formula: —$Q^2$—$Ar^2$ as said substituent, $Ar^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl; $Q^2$ is a single bond, oxygen, carbonyl or —$N(R^3)$—.

"Aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl" refers to unsubstituted said aryl or said heteroaryl, or said aryl or said heteroaryl having substituent(s) at the substitutable, arbitrary position(s) wherein said substituent(s) may be one, two or more, preferably one or two member(s) identically or differently selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl.

Halogen as said substituent preferably includes fluorine, chlorine and the like.

Lower alkyl as said substituent preferably includes methyl, ethyl, propyl, isopropyl and the like.

Halo-lower alkyl as said substituent preferably includes difluoromethyl, trifluoromethyl and the like.

Hydroxy-lower alkyl as said substituent preferably includes hydroxymethyl, 2-hydroxyethyl, 1-hydroxy-1-methylethyl and the like.

Lower alkoxy as said substituent preferably includes methoxy, ethoxy and the like.

Halo-lower alkoxy as said substituent preferably includes fluoromethoxy, difluoromethoxy, trifluoromethoxy and the like.

Lower alkylamino as said substituent preferably includes methylamino, ethylamino and the like.

Di-lower alkylamino as said substituent preferably includes dimethylamino, diethylamino and the like.

Lower alkanoyl as said substituent preferably includes acetyl, propionyl and the like.

Aryl as said substituent preferably includes phenyl and the like.

The substituent(s) of $Ar^2$ preferably include(s) halogen, cyano, lower alkyl, halo-lower alkyl, hydroxy-lower alkyl, hydroxy, halo-lower alkoxy and the like.

Aryl as $Ar^2$ preferably includes phenyl and the like, and heteroaryl as $Ar^2$ preferably includes pyridyl, quinolyl and the like.

In the group of formula: —$N(R^3)$— as $Q^1$ and $Q^2$, $R^3$ is hydrogen or lower alkyl.

$R^3$ preferably includes hydrogen, methyl, ethyl and the like.

$Q^2$ preferably includes a single bond and the like.

The substituent(s) of $Ar^1$ include(s) preferably halogen, hydroxy, lower alkyl, halo-lower alkyl, lower alkenyl, lower alkoxy, lower alkanoyl, —$Q^2$—$Ar^2$ and the like, more preferably halogen, hydroxy, halo-lower alkyl, lower alkoxy and the like.

Aryl as $Ar^1$ preferably includes phenyl and the like, and heteroaryl as $Ar^1$ includes preferably imidazolyl, furyl, thienyl, pyrazolyl, thiazolyl, oxazolyl, isoxazolyl, 1,2,4-oxadiazol, 1,3,4-oxadiazol, pyridyl, pyrazinyl, pyrimidinyl, benzofuranyl, quinolyl and the like, more preferably pyridyl, quinolyl and the like, most preferably pyridyl and the like.

Consequently, $Ar^1$ includes, for example, phenyl, 2-fluorophenyl, 3-fluorophenyl, 4-fluorophenyl, 2,3-difluorophenyl, 2,4-difluorophenyl, 2,6-difluorophenyl, 3,5-difluorophenyl, 2-chlorophenyl, 3-chlorophenyl, 4-chlorophenyl, 2-bromophenyl, 3-bromophenyl, 4-bromophenyl, 2-chloro-4-fluorophenyl, 2-chloro-5-fluorophenyl, 2-chloro-6-fluorophenyl, 2-bromo-4-fluorophenyl, 2-bromo-5-fluorophenyl, 2-methylphenyl, 3-methylphenyl, 4-methylphenyl, 5-fluoro-2-methylphenyl, 3-fluoromethylphenyl, 2-trifluoromethylphenyl, 3-trifluoromethylphenyl, 4-trifluoromethylphenyl, 2-methoxyphenyl, 3-methoxyphenyl, 4-methoxyphenyl, 5-fluoro-2-methoxyphenyl, 3-fluoromethoxyphenyl, 2-difluoromethoxyphenyl, 3-difluoromethoxyphenyl, 2-hydroxy-4-fluorophenyl, 2-hydroxymethylphenyl, 3-hydroxymethylphenyl, 3-hydroxyphenyl, 4-hydroxyphenyl, 2-imidazolyl, 2-furyl, 2-thienyl, 1,2,4-oxadiazol-5-yl, 1,3,4-oxadiazol-2-yl, 1,2,4-thiadiazol-5-yl, 1,3,4-thiadiazol-2-yl, 2-pyridyl, 3-pyridyl, 4-pyridyl, 2-fluoro-5-pyridyl, 3-fluoro-6-pyridyl, 2-pyrimidinyl, 4-benzo[b]furanyl, 5-benzo[b]furanyl, 7-benzo[b]furanyl, 2-quinolyl, 3-quinolyl, 4-quinolyl, 5-quinolyl, 6-quinolyl, 8-quinolyl and the like. Preferably, $Ar^1$ includes phenyl, 2-fluorophenyl, 4-fluorophenyl, 2,4-difluorophenyl, 2,5-difluorophenyl, 2-chloro-4-fluorophenyl, 2-chloro-5-fluorophenyl, 2-trifluoromethylphenyl, 2-difluoromethoxyphenyl, 3-difluoromethoxyphenyl, 3-hydroxyphenyl, 4-hydroxyphenyl, 2-pyridyl, 2-fluoro-5-pyridyl, 3-fluoro-6-pyridyl, 7-benzo[b]furanyl, 2-quinolyl, 3-quinolyl and the like.

$Q^1$ includes preferably a single bond, oxygen, —$N(R^3)$— and the like, more preferably a single bond and the like.

The substituent(s) of methine as A, B, C or D include(s) preferably halogen, halo-lower alkyl, lower alkoxycarbonyl, —$N(R^1)R^2$, —$Q^1$—$Ar^1$ and the like, more preferably —$Q^1$—$Ar^1$ and the like.

The preferred embodiment of A, B, C and D includes, for example, the case where A and D are same or differently unsubstituted methine or nitrogen, and one of B and C is methine having —$Q^1$—$Ar^1$ and the other is unsubstituted methine or nitrogen, more preferably the case where A is unsubstituted methine, B and/or D are nitrogen, and C is methine having —$Q^1$—$Ar^1$.

E is methine, hydroxy substituted methine or nitrogen, preferably methine.

n is 0 or 1, preferably 0.

T, U, V and W are independently methine or nitrogen, said methine being optionally substituted by a substituent selected from the group consisting of halogen, lower alkyl, halo-lower alkyl, hydroxy, lower alkoxy and halo-lower alkoxy, and at least two of T, U, V and W are said methine group.

"Methine which is optionally substituted by a substituent selected from the group consisting of halogen, lower alkyl, halo-lower alkyl, hydroxy, lower alkoxy and halo-lower alkoxy" refers to unsubstituted methine or methine having a substituent, wherein said substituent may be selected from the group consisting of halogen, lower alkyl, halo-lower alkyl, hydroxy, lower alkoxy and halo-lower alkoxy.

Halogen as said substituent preferably includes fluorine, chlorine and the like.

Lower alkyl as said substituent preferably includes methyl, ethyl and the like.

Halo-lower alkyl as said substituent preferably includes difluoromethyl, trifluoromethyl and the like.

Lower alkoxy as said substituent preferably includes methoxy, ethoxy and the like.

Halo-lower alkoxy as said substituent preferably includes fluoromethoxy, difluoromethoxy, trifluoromethoxy and the like.

Said substituent includes preferably halogen, lower alkyl, hydroxy, lower alkoxy and the like, more preferably halogen and the like.

The preferred embodiment of T, U, V and W includes, for example, the case where T, U, V and W are independently methine optionally having said substituent, preferably halogen, lower alkyl, hydroxy and lower alkoxy, more preferably halogen; or the case where one of T, U, V and W is nitrogen, preferably the case where one of T, U, V and W is nitrogen and one of the remainder is methine having said substituent, preferably halogen, lower alkyl, hydroxy and lower alkoxy, more preferably halogen; or the case where one of T, U, V and W is nitrogen and all of the remainder are unsubstituted methine.

X is —N(SO$_2$R$^4$)—, —N(COR$^5$)— or —CO—. Y is —C(R$^6$)(R$^7$)—, —O— or —N(R$^8$)—. R$^4$ is lower alkyl, aralkyl or aryl. R$^5$ and R$^8$ are independently hydrogen, lower alkyl, aralkyl or aryl. R$^6$ and R$^7$ are independently hydrogen, hydroxy, lower alkyl, aralkyl or aryl.

Lower alkyl as R$^4$, R$^5$, R$^6$, R$^7$ or R$^8$, each independently, preferably includes methyl, ethyl, propyl and the like.

Aralkyl as R$^4$, R$^5$, R$^6$, R$^7$ or R$^8$, each independently, preferably includes benzyl and the like.

Aryl as R$^4$, R$^5$, R$^6$, R$^7$ or R$^8$, each independently, preferably includes phenyl and the like.

R$^4$ and R$^5$ preferably include, for example, lower alkyl and the like.

The preferred embodiment of R$^6$ and R$^7$ includes, for example, the case where both R$^6$ and R$^7$ are hydrogen.

R$^8$ includes preferably, for example, hydrogen, lower alkyl and the like, more preferably hydrogen and the like.

The preferred embodiment of n, X and Y includes, for example, the case where n is 0, X is —N(SO$_2$R$^4$)— or —N(COR$^5$)—, preferably —N(SO$_2$R$^4$)—, and Y is —C(R$^6$)(R$^7$)—; or the case where n is 0 or 1, preferably 0, X is —CO—, and Y is —O— or —N(R$^8$)—, preferably —O—. In the latter case, it is more preferable when X is —CO— and Y is —O— or —NH—, and further preferable when X is —CO— and Y is —O—.

The present invention excludes a compound of the formula (I), wherein at the same time E is nitrogen, n is 0, X is —CO— and Y is —O—.

In more detail, a group of formula (a):

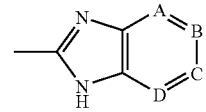

in the formula (I) includes a group of formula (a$_1$):

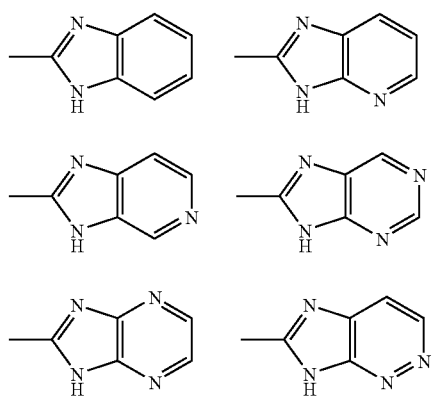

wherein methine in the formula (a$_1$) is optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and —Q$^1$—Ar$^1$, and the like, more preferably a group of formula (a$_2$)

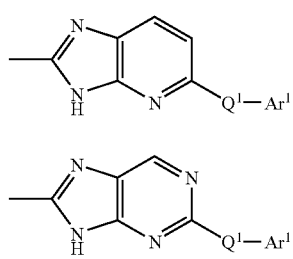

(wherein Ar$^1$ and Q$^1$ have the aforesaid meaning), and the like.

Moreover, a group of formula (b):

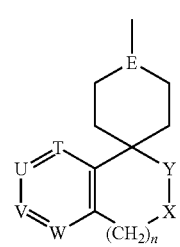

in the formula (I) includes a group of formula (b₁):

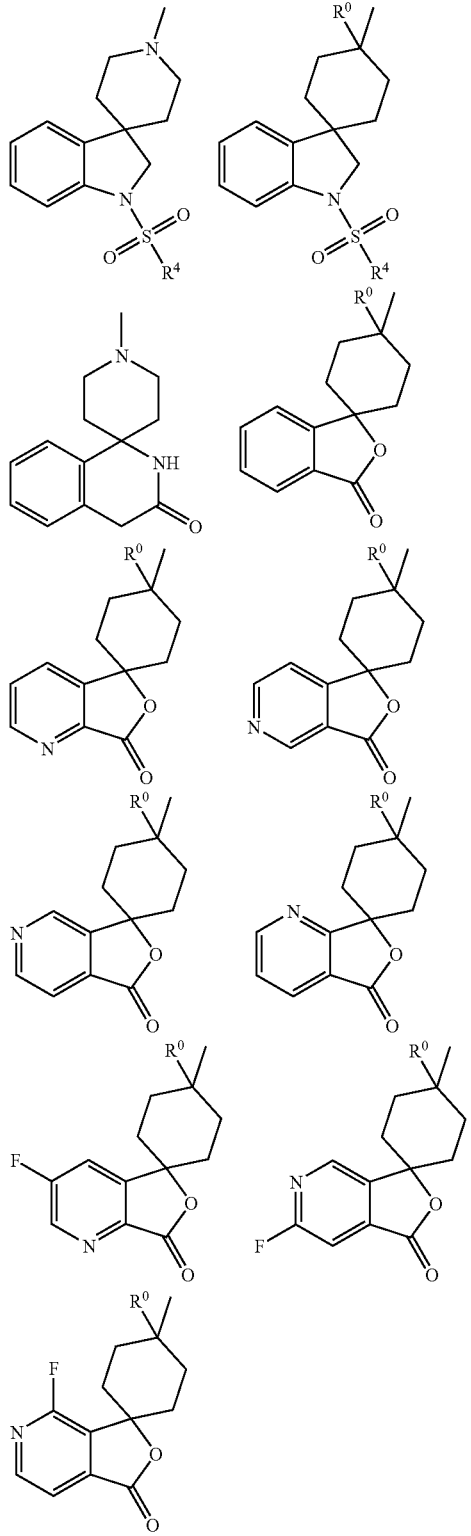

(wherein R⁰ is hydrogen or hydroxy; R⁴ has the aforesaid meaning),
and the like.

Preferred compounds of the formula (I) are, for example, compounds of the formula (I-a):

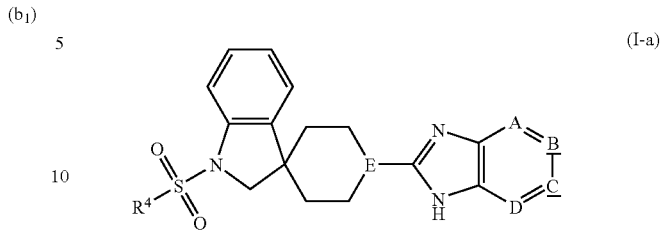

(wherein A, B, C, D, E and R⁴ have the aforesaid meaning); compounds of the formula (I-b):

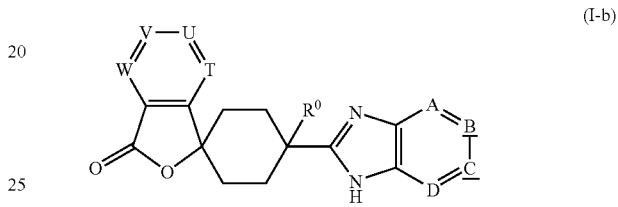

(wherein A, B, C, D, R⁰, T, U, V and W have the aforesaid meaning); compounds of the formula (I-c):

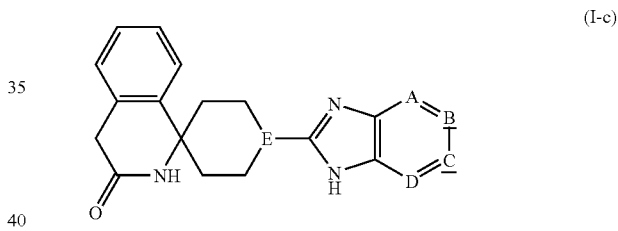

(wherein A, B, C, D and E have the aforesaid meaning); or the like.

Among the compounds of the formula (I), the formula (I-a), the formula (I-b) or the formula (I-c), the preferred compounds are, for example, compounds in which A, B, C and D are aforesaid preferred embodiment, Ar¹ is phenyl or heteroaryl, more preferably phenyl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsufonyl, carboxyl, lower alkanoyl, lower alkoxycarbonyl, lower alkanoylamino and —Q²—Ar², and R⁰ is hydrogen.

Further, among the compound of the formula (I-b), the preferred compounds are, for example, compounds in which all of T, U, V and W are unsubstituted methine; or compounds in which one of T, U, V and W is nitrogen, preferably one of T, U, V and W is nitrogen and all of the remainder are unsubstituted methine or one of the remainder is methine having fluorine or chlorine.

The compounds of the present invention may include stereoisomers such as optical isomers, diastereoisomers and geometrical isomers, or tautomers depending upon the mode of substituents. The compounds of the present invention include all the stereoisomers, tautomers and their mixtures.

For example, compounds of the formula (I-a) include stereoisomers such as a trans-form compound of the formula (I-1a) or (I-1a'):

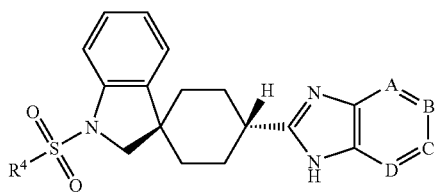
(I-1a)

and a cis-form compound of the formula (I-2a) or (I-2a'):

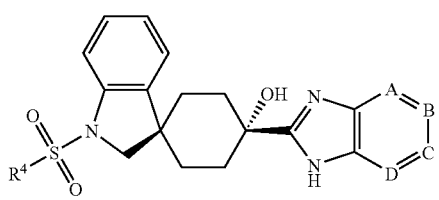
(I-1a')

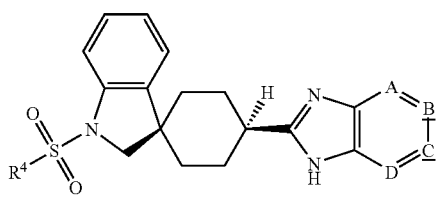
(I-2a)

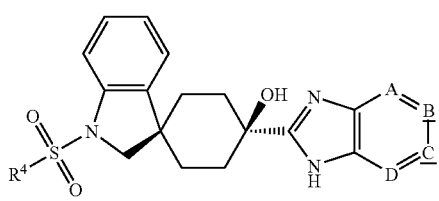
(I-2a'), and compounds of the formulae (I-1a) and (I-2a') are preferable.

Compounds of the formula (I-b) include stereoisomers such as a trans-form compound of the formula (I-1b) or (I-1b'):

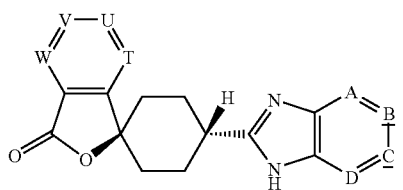
(I-1b)

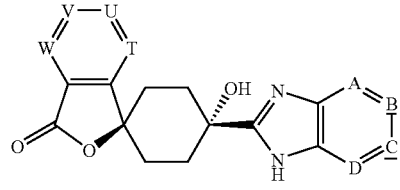
(I-1b')

and a cis-form compound of the formula (I-2b) or (I-2b'):

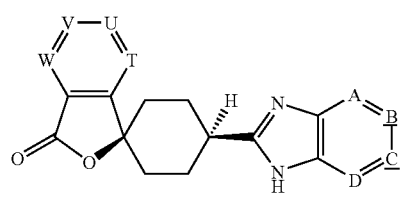
(I-2b)

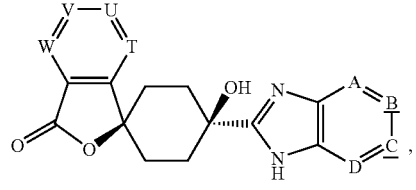
(I-2b'), and compounds of formulae (I-1b) and (I-2b') are preferable.

Compounds of the formula (I-c) wherein E is methine, include stereoisomers such as a trans-form compound of the formula (I-1c) or (I-1c'):

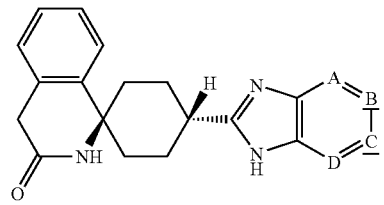
(I-1c)

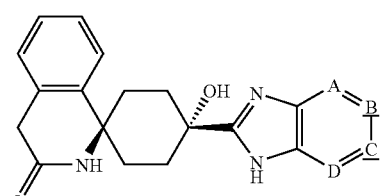
(I-1c')

and a cis-form compound of the formula (I-2c) or (I-2c'):

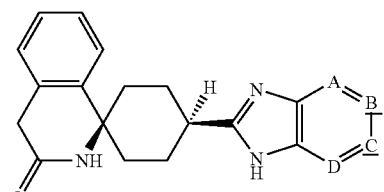
(I-2c)

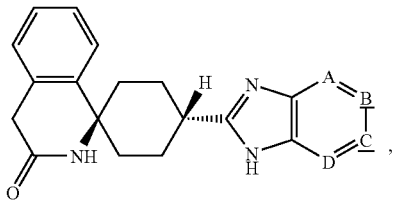

(I-2c')

and compounds of the formulae (I-1c) and (I-2c') are preferable.

Also included within the scope of the invention are polymorphs, hydrates and solvates of the compounds of the present invention.

The present invention also includes prodrugs of the compounds of this invention within its scope. In general, such prodrugs are functional derivatives of the compounds of the present invention which can be readily converted in vivo into the required compound. Thus, in the treatment methods for various diseases according to the present invention, the term "administering" shall encompass not only administration of the compound specified in this disclosure but also administration of a compound which is converted in vivo into the specified compound when it is administered to a patient. Conventional procedures for selection and preparation of suitable prodrug derivatives are described, for example, in "Design of Prodrugs," ed. H. Bundgaard, Elsevier (1985), which are entirely incorporated by reference in this specification. Metabolites of these compounds include active compounds produced upon introduction of compounds of the present invention into the biological milieu, and are encompassed in the scope of the present invention.

The specific compound of the formula (I) is, for example, 2-[1-methylsulfonylspiro[indoline-3,4'-piperidin]-1'-yl]-5-chlorobenzimidazole, 5,6-dichloro-2-[1-methylsulfonyl-spiro[indoline-3,4'-piperidin]-1'-yl]benzimidazole, 5-chloro-2-[1-ethylsulfonylspiro[indoline-3,4'-piperidin]-1'-yl]benzimidazole, trans-5-chloro-2-[3'-oxospiro[cyclohexane-1,1'(3'H)-isobenzofuran]-4-yl]-6-(trifluoromethyl)benzimidazole, trans-5-(4-fluorophenyl)-2-[3'-oxospiro[cyclohexane-1,1'(3'H)-isobenzofuran]-4-yl]benzimidazole, trans-2-[3-oxospiro[6-azaisobenzofuran-1(3H),1'-cyclo-hexan]-4'-yl]-5-phenylbenzimidazole, trans-5-(3-fluorophenyl)-2-[3-oxospiro[6-azaisobenzofuran-1(3H),1'-cyclo-hexan]-4'-yl]benzimidazole, trans-5-(4-fluorophenyl)-2-[3-oxospiro[6-azaisobenzofuran-1(3H),1'-cyclo-hexan]-4'-yl]benzimidazole, trans-2-[3'-oxospiro[cyclohexane-1,1'(3'H)-isobenzofuran]-4-yl]-5-(2-pyridyl)imidazo[4,5-b]pyridine, trans-2-[3'-oxospiro[cyclohexane-1,1'(3'H)-isobenzofuran]-4-yl]-6-(2-pyridyl)imidazo[4,5-b]pyridine, trans-5-(2-fluorophenyl)-2-[3-oxospiro[6-azaisobenzofuran-1(3H),1'-cyclo-hexan]-4'-yl]imidazo[4,5-b]pyridine, trans-2-[3-oxospiro[6-azaisobenzofuran-1(3H),1'-cyclo-hexan]-4'-yl]-6-phenylimidazo[4,5-c]pyridine, trans-6-(2-fluorophenyl)-2-[3-oxospiro[6-azaisobenzofuran-1(3H),1'-cyclo-hexan]-4'-yl]imidazo[4,5-c]pyridine, trans-2-[3-oxospiro[6-azaisobenzofuran-1(3H),1'-cyclo-hexan]-4'-yl]-5-phenylimidazo[4,5-b]pyrazine, trans-5-(4-fluorophenyl)-2-[3-oxospiro[6-azaisobenzofuran-1(3H),1'-cyclohexan]-4'-yl]imidazo[4,5-b]pyrazine, trans-6-(4-fluorophenyl)-2-[3-oxospiro[6-azaisobenzofuran-1(3H),1'-cyclohexan]-4'-yl]imidazo[4,5-c]pyridazine, trans-2-(2-fluorophenyl)-8-[3'-oxospiro[cyclohexane-1,1'(3'H)-isobenzofuran]-4-yl]purine, trans-2-(3-fluorophenyl)-8-[3'-oxospiro[cyclohexane-1,1'(3'H)-isobenzofuran]-4-yl]purine, trans-2-(4-fluorophenyl)-8-[3'-oxospiro[cyclohexane-1,1'(3'H)-isobenzofuran]-4-yl]purine, trans-2-(2-methoxyphenyl)-8-[3'-oxospiro[cyclohexane-1,1'(3'H)-isobenzofuran]-4-yl]purine, trans-2-(4-methoxyphenyl)-8-[3'-oxospiro[cyclohexane-1,1'(3'H)-isobenzofuran]-4-yl]purine, trans-2-(2-methylphenyl)-8-[3'-oxospiro[cyclohexane-1,1'(3'H)-isobenzofuran]-4-yl]purine, trans-8-[3'-oxospiro[cyclohexane-1,1'(3'H)-isobenzofuran]-4-yl]-2-(2-trifluoromethylphenyl)purine, trans-2-(2-chloro-4-fluorophenyl)-8-[3'-oxospiro[cyclo-hexane-1,1'(3'H)-isobenzofuran]-4-yl]purine, trans-2-(2-hydroxymethylphenyl)-8-[3'-oxospiro[cyclo-hexane-1,1'(3'H)-isobenzofuran]-4-yl]purine, trans-2-(2-furyl)-8-[3'-oxospiro[cyclohexane-1,1'(3'H)-isobenzofuran]-4-yl]purine, trans-8-[3'-oxospiro[cyclohexane-1,1'(3'H)-isobenzofuran]-4-yl]-2-(2-thienyl)purine, trans-8-[3'-oxospiro[cyclohexane-1,1'(3'H)-isobenzofuran]-4-yl]-2-(2-payroll)purine, trans-2-(3-fluoropyridin-6-yl)-8-[3'-oxospiro[cyclohexane-1,1'(3'H)-isobenzofuran]-4-yl]purine, trans-2-(2-chloropyridin-6-yl)-8-[3'-oxospiro[cyclohexane-1,1'(3'H)-isobenzofuran]-4-yl]purine, trans-2-(2-fluorophenoxy)-8-[3'-oxospiro[cyclohexane-1,1'(3'H)-isobenzofuran]-4-yl]purine, trans-2-(2,6-difluorophenoxy)-8-[3'-oxospiro[cyclohexane-1,1'(3'H)-isobenzofuran]-4-yl]purine, trans-8-[3'-oxospiro[cyclohexane-1,1'(3'H)-isobenzofuran]-4-yl]-2-(1-piperidyl)purine, trans-8-[3-oxospiro[6-azaisobenzofuran-1(3H),1'-cyclo-hexan]-4'-yl]-2-phenylpurine, trans-2-(2-fluorophenyl)-8-[3-oxospiro[6-azaisobenzofuran-1(3H),1'-cyclohexan]-4'-yl]purine, trans-2-(3-fluorophenyl)-8-[3-oxospiro[6-azaisobenzofuran-1(3H),1'-cyclohexan]-4'-yl]purine, trans-2-(4-fluorophenyl)-8-[3-oxospiro[6-azaisobenzofuran-1(3H),1'-cyclohexan]-4'-yl]purine, trans-2-(2-chlorophenyl)-8-[3-oxospiro[6-azaisobenzofuran-1(3H),1'-cyclohexan]-4'-yl]purine, trans-2-(3-chlorophenyl)-8-[3-oxospiro[6-azaisobenzofuran-1(3H),1'-cyclohexan]-4'-yl]purine, trans-2-(4-chlorophenyl)-8-[3-oxospiro[6-azaisobenzofuran-1(3H),1'-cyclohexan]-4'-yl]purine, trans-2-(2-chloro-4-fluorophenyl)-8-[3-oxospiro[6-azaisobenzofuran-1(3H),1'-cyclohexan]-4'-yl]purine, trans-2-(4-methoxyphenyl)-8-[3-oxospiro[6-azaisobenzofuran-1(3H),1'-cyclohexan]-4'-yl]purine, trans-2-(2-methylphenyl)-8-[3-oxospiro[6-azaisobenzofuran-1(3H),1'-cyclohexan]-4'-yl]purine, trans-2-(2-difluoromethoxyphenyl)-8-[3-oxospiro[6-azaiso-benzofuran-1(3H),1'-cyclohexan]-4'-yl]purine, trans-2-(3-difluoromethoxyphenyl)-8-[3-oxospiro[6-azaiso-benzofuran-1(3H),1'-cyclohexan]-4'-yl]purine, trans-8-[3-oxospiro[6-azaisobenzofuran-1(3H),1'-cyclo-hexan]-4'-yl]-2-(2-trifluoromethylphenyl)purine, trans-2-(2,4-difluorophenyl)-8-[3-oxospiro[6-azaisobenzofuran-1(3H),1'-cyclohexan]-4'-yl]purine, trans-2-(2,5-difluorophenyl)-8-[3-oxospiro[6-azaisobenzo-furan-1(3H),1'-cyclohexan]-4'-yl]purine, trans-2-(2-bromo-4-fluorophenyl)-8-[3-oxospiro[6-azaiso-benzofuran-1(3H),1'-cyclohexan]-4'-yl]purine, trans-2-(4-chloro-2-fluorophenyl)-8-[3-oxospiro[6-azaiso-benzofuran-1(3H),1'-cyclohexan]-4'-yl]purine, trans-8-[3-oxospiro[6-azaisobenzofuran-1(3H),1'-cyclo-hexan]-4'-yl]-2-(3-quinolyl)purine, trans-8-[5-fluoro-3-oxospiro[6-azaisobenzofuran-1(3H),1'-cyclohexan]-4'-yl]-2-phenylpurine, trans-8-[5-fluoro-3-oxospiro[6-azaisobenzofuran-1(3H),1'-cyclohexan]-4'-yl]-2-(2-fluorophenyl)purine, trans-2-(2,4-difluorophenyl)-8-[5-fluoro-3-oxospiro[6-aza-isobenzofuran-1(3H),1'-cyclohexan]-4'-yl]purine, trans-2-(2,5-difluorophenyl)-8-[5-fluoro-3-oxospiro[6-aza-isobenzofuran-1(3H),1'- cyclohexan]-4'-yl]purine, trans-2-(4-fluorophenyl)-8-[7-hydroxy-3-oxospiro[6-aza-isobenzofuran-1(3H),1'-cyclohexan]-4'-yl]purine, 5,6-dichloro-2-[3,4-dihydro-3-oxospiro[isoquinoline-1(2H),4'-piperidin]-1'-yl]benzimidazole, 2-[3,4-dihydro-3-oxospiro[isoquinoline-1(2H),4'-piperidin]-1'-yl]-5-phenylbenzimidazole, 8-[3,4-dihydro-3-oxospiro[isoquinoline-1(2H),4'-piperidin]-1'-yl]-2-phenylpurine, 8-[3,4-dihydro-3-oxospiro[isoquinoline-1(2H),4'-piperidin]-1'-yl]-2-(2-fluorophenyl)purine, 8-[3,4-dihydro-3-oxospiro[isoquinoline-1(2H),4'-piperidin]-1'-yl]-2-(4-fluorophenyl)purine, trans-8-[3',4'-dihydro-3'-oxospiro[cyclohexane-1,1'(2'H)-isoquinolin]-4-yl]-2-phenylpurine, trans-2-[3',4'-dihydro-3'-oxospiro[cyclohexane-1,1'(2'H)-isoquinolin]-4-yl]-5-phenylbenzimidazole, trans-8-[3',4'-dihydro-3'-oxospiro[cyclohexane-1,1'(2'H)-isoquinolin]-4-yl]-2-(2-fluorophenyl)purine, trans-8-[3',4'-dihydro-3'-oxospiro[cyclohexane-1,1'(2'H)-isoquinolin]-4-yl]-2-(4-fluorophenyl)purine, trans-2-(4-fluorophenyl)-8-[7-hydroxy-3-oxospiro[6-azaiso-benzofuran-1(3H), 1'-cyclohexan]-4'-yl]purine, trans-2-(4-fluorophenyl)-8-[3-oxospiro[6-azaisobenzofuran-1(3H), 1'-cyclohexan]-4'-yl]purine 6-oxide, trans-2-(4-fluoro-2-hydroxyphenyl)-8-[3-oxospiro[6-azaiso-benzofuran-1(3H), 1'-cyclohexan]-4'-yl]purine, trans-2-(4-fluorophenyl)-6-hydroxy-8-[3-oxospiro[6-azaiso-benzofuran-1(3H), 1'-cyclohexan]-4'-yl]purine, trans-2-(4-hydroxyphenyl)-8-[3-oxospiro[6-azaisobenzofuran-1(3H), 1'-cyclohexan]-4'-yl]purine, trans-2-(4-fluoro-3-hydroxyphenyl)-8-[3-oxospiro[6-azaiso-benzofuran-1(3H), 1'-cyclohexan]-4'-yl]purine, cis-2-(4-fluorophenyl)-8-[4'-hydroxy-3-oxospiro[6-azaiso-benzofuran-1(3H), 1'-cyclohexan]-4'-yl]purine, and the like.

Among these compounds, the preferable compound is, for example, trans-8-[3'-oxospiro[cyclohexane-1,1'(3'H)-isobenzofuran]-4-yl]-2-phenylpurine, trans-2-(2-fluorophenyl)-8-[3'-oxospiro[cyclohexane-1,1'(3'H)-isobenzofuran]-4-yl]purine, trans-2-(4-fluorophenyl)-8-[3-oxospiro[6-azaisobenzofuran-1(3H), 1'-cyclohexan]-4'-yl]purine, trans-2-(2,5-difluorophenyl)-8-[3-oxospiro[6-azaisobenzo-furan-1(3H), 1'-cyclohexan]-4'-yl]purine, trans-8-[5-fluoro-3-oxospiro[6-azaisobenzofuran-1(3H),1'-cyclohexan]-4'-yl]-2-(2-fluorophenyl)purine, trans-5-(2-fluorophenyl)-2-[3-oxospiro[6-azaisobenzofuran-1(3H), 1'-cyclohexan]-4'-yl]imidazo[4,5-b]pyridine, and the like.

The process for producing compounds of the present invention is illustrated as follows.

Compounds (I) of the present invention can be synthesized, for example, by the following production methods or the processes shown in examples, but these embodiments are not intended to restrict the process for producing compounds (I) of this invention.

Production Process 1

A compound of the formula (I-1) or N-oxide derivative thereof:

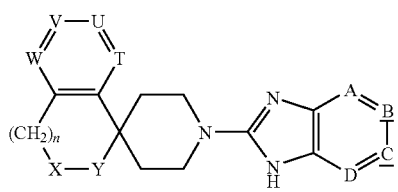

(I-1)

(wherein A, B, C, D, n, T, U, V, W, X and Y have each the same meaning as defined above) can be prepared by reacting a compound of the formula (II):

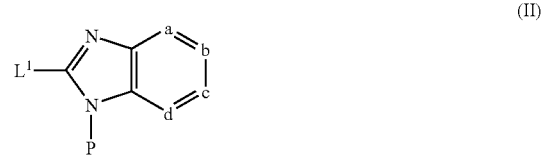

(II)

(wherein a, b, c and d are independently methine or nitrogen, said methine being optionally substituted by a substituent selected from the group consisting of halogen, cyano, lower alkyl, halo-lower alkyl, lower alkoxy, halo-lower alkoxy, lower alkoxycarbonyl, lower alkylsulfonyl, lower alkylsulfonyloxy, —N(R$^{1p}$)R$^{2p}$, —Q$^{1p}$—Ar$^1p$ and optionally protected hydroxy, and at least one of a, b, c and d is said methine;

Ar$^1p$ is aryl or heteroaryl, any of which is optionally substituted by a substituent selected from the group consisting of halogen, nitro, lower alkyl, halo-lower alkyl, cyclo-lower alkyl, lower alkenyl, lower alkoxy, halo-lower alkoxy, lower alkylthio, lower alkylsulfonyl, lower alkanoyl, lower alkoxycarbonyl, lower alkanoylamino, —Q$^{2p}$—Ar$^{2p}$, optionally protected hydroxy, optionally protected hydroxy-lower alkyl, and optionally protected carboxyl;

Ar$^2p$ is aryl or heteroaryl, any of which is optionally substituted by a substituent selected from the group consisting of halogen, cyano, lower alkyl, halo-lower alkyl, lower alkoxy, halo-lower alkoxy, lower alkylamino, di-lower alkylamino, lower alkanoyl, aryl, optionally protected hydroxy-lower alkyl and optionally protected hydroxy;

L$^1$ is a leaving group;

P is an imino-protecting group;

Q$^1p$ and Q$^2p$ are independently a single bond, oxygen, optionally protected carbonyl or —N(R$^3$)—;

R$^1p$ and R$^2p$ are independently an amino-protecting group, an imino-protecting group, hydrogen or lower alkyl, or R$^1p$ and R$^{2p}$, taken together, form lower alkylene which may be intervened by oxygen, sulfur or optionally protected imino;

R$^3$ has the same meaning as defined above) with a compound of the formula (III):

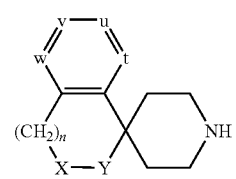

(III)

(wherein n, X and Y have each the same meaning as defined above, provided that the compound (III) when n is 0, X is —CO— and Y is —O— is excluded) or its salt to give a compound of the formula (IV-1):

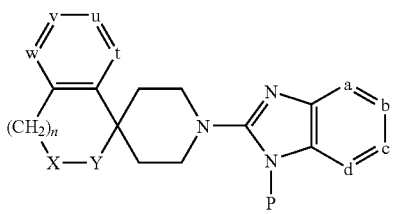

(IV-1)

(wherein a, b, c, d, n, P, t, u, v, w, X and Y have each the same meaning as defined above), and optionally removing wherefrom protecting group(s) and/or oxidizing nitrogen atom(s) of the compound (IV-1).

The leaving groups represented by $L^1$ include, for example, halogen (e.g. chlorine, bromine, iodine), organic sulfonyl (e.g. methanesulfonyl, ethanesulfonyl, benzenesulfonyl), organic sulfonyloxy (e.g. methanesulfonyloxy, trifluoromethanesulfonyloxy, p-toluenesulfonyloxy) and the like.

The present process refers to a process for preparing a compound of the formula (I) wherein E is nitrogen, namely a compound of the formula (I-1).

In the above reaction, when a reactant has an amino, imino, hydroxy, carboxyl, carbonyl or the like which does not participate in the reaction, the reaction may be carried out after protecting the amino, imino, hydroxy, carboxyl, carbonyl with an amino- or imino-protecting group, a hydroxy-protecting group, a carboxyl-protecting group, or a carbonyl-protecting group, followed by deprotection after completion of the reaction.

The "amino- or imino-protecting group" is not particularly restricted, so long as it has such protective function. There are employed, for example, aralkyl (e.g. benzyl, p-methoxybenzyl, 3,4-dimethoxybenzyl, o-nitrobenzyl, p-nitrobenzyl, benzhydryl, trityl); lower alkanoyl (e.g. formyl, acetyl, propionyl, butyryl, pivaloyl); benzoyl; arylalkanoyl (e.g. phenylacetyl, phenoxyacetyl); lower alkoxycarbonyl(e.g. methoxycarbonyl, ethoxycarbonyl, propyloxycarbonyl, tert-butoxycarbonyl); aralkyloxycarbonyl (e.g. benzyloxycarbonyl, p-nitrobenzyloxycarbonyl, phenethyloxycarbonyl); lower alkylsilyl (e.g. trimethylsilyl, tert-butyldimethylsilyl); tetrahydropyranyl; trimethylsilylethoxymethyl; lower alkylsulfonyl (e.g. methylsulfonyl, ethylsulfonyl); arylsulfonyl (e.g. benzenesulfonyl, toluenesulfonyl) and the like, among which the particularly preferred are acetyl, benzoyl, tert-butoxycarbonyl, trimethylsilylethoxymethyl, methylsulfonyl and the like.

The "hydroxy-protecting group" is not particularly restricted, so long as it has such protective function for hydroxy groups. There are employed, for example, lower alkyl (e.g. methyl, ethyl, propyl, isopropyl, tert-butyl); lower alkylsilyl (e.g. trimethyl silyl, tert-butyldimethylsilyl); lower alkoxymethyl (e.g. methoxymethyl, 2-methoxy-ethoxymethyl); tetrahydropyranyl; trimethylsilylethoxymethyl; aralkyl (e.g. benzyl, p-methoxybenzyl, 2,3-dimethoxybenzyl, o-nitrobenzyl, p-nitrobenzyl, trityl); and acyl (e.g. formyl, acetyl), among which the particularly preferred are methyl, methoxymethyl, tetrahydropyranyl, trityl, trimethylsilylethoxymethyl, tert-butyldimethylsilyl, acetyl and the like.

The "carboxyl-protecting group" is not particularly restricted, so long as it has such protective function for carboxyl groups. There are employed, for example, lower alkyl (e.g. methyl, ethyl, propyl, isopropyl, tert-butyl); halo-lower alkyl (e.g. 2,2,2-trichloroethyl); lower alkenyl (e.g. 2-propenyl); aralkyl (e.g. benzyl, p-methoxybenzyl, p-nitrobenzyl, benzhydryl, trityl) and the like, among which the particularly preferred are methyl, ethyl, tert-butyl, 2-propenyl, benzyl, p-methoxybenzyl or benzhydryl and the like.

The "carbonyl-protecting group" is not particularly limited, so long as it has such protective function for carbonyl groups. There are employed, for example, acetals or ketals, such as ethylene ketal, trimethylene ketal, and dimethyl ketal and the like.

The reaction between a compound of the formula (II) and a compound of the formula (III) is usually carried out by employing an equivalent to excessive mole, preferably an equivalent to 1.5 moles, of compound (III), relative to 1 mole of compound (II).

The reaction is usually carried out in an inert solvent. Preferable examples of such solvent are methylene chloride, chloroform, tetrahydrofuran, dioxane, dimethylformamide, N-methylpyrrolidone, dimethyl sulfoxide and the like, or a mixture thereof and the like.

The reaction is preferably carried out in the presence of a base such as organic bases (e.g. triethylamine, diisopropylethylamine, pyridine, 4-dimethylaminopyridine), inorganic bases (e.g. sodium hydrogen carbonate, sodium carbonate, potassium carbonate, cesium carbonate, sodium hydroxide, potassium hydroxide) and the like.

The base is used in equimolar amount or in excess mole, preferably 1 to 5 moles, relative to 1 mole of the compound of the formula (II).

The reaction temperature is usually from 0° C. to 200° C., preferably 20° C. to 150° C.

The reaction time is usually 5 minutes to 7 days, preferably 30 minutes to 24 hours.

A usual treatment is carried out after completion of the reaction to obtain a crude product of a compound of the formula (IV-1). The resulting compound of the formula (IV-1) is, with or without purification according to the common method, subjected to optional removal of the protecting group for the amino, hydroxy, carboxyl, carbonyl or the like, thereby a compound of the formula (I-1) can be prepared.

Although the method for the removal of said protecting groups depends upon the kinds of the protecting groups, the stability of a desired compound (I-1) and the like, it is carried out by, for example, a solvolysis using an acid or a base, that is, a method wherein for example 0.01 mole to a large excess of acid, preferably trifluoroacetic acid, formic acid, hydrochloric acid and the like, or an equivalent mole to a large excess of base, preferably potassium hydroxide, calcium hydroxide and the like is acted; a chemical reduction using a metal hydride complex; or a catalytic reduction using a palladium-carbon catalyst, a Raney-nickel catalyst, etc.; and the like, according to, for example, a method described in the literature (Protective Groups in Organic Synthesis, T. W. Greene, John Wiley & Sons, (1981)) or its similar method.

The oxidation of a nitrogen atom may be carried out by using of an oxidizing agent (for example m-chloroperbenzoic acid, dioxirane, sodium periodate and hydrogen peroxide). Reaction between a compound of the general formula (IV-1) and an oxidizing agent is usually carried out by employing 0.5 mole to excessive moles, preferably 1 mole to 5 moles of the oxidizing agent based on 1 mole of compound (IV-1).

The reaction is usually carried out in an appropriate solvent which depend on the oxidizing agent used in the reaction. Preferable examples of the solvent include methylene chloride and chloroform for m-chloroperbenzoic acid, acetone and water for dioxirane.

Reaction temperature is usually −50° C. to 100° C., preferably −20° C. to 50° C.

Reaction time is usually 15 minutes to 7 days, preferably 30 minutes to 24 hours.

Production Process 2

A compound of the formula (I-2) or N-oxide derivative thereof:

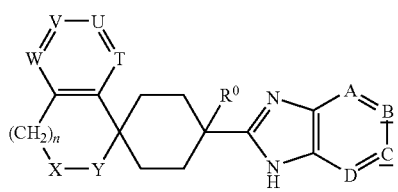
(I-2)

(wherein A, B, C, D, n, R⁰, T, U, V, W, X and Y have each the same meaning as defined above) can be prepared by reacting a compound of the formula (V):

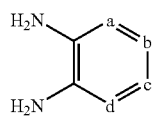
(V)

(wherein a, b, c and d have each the same meaning as defined above) or its salt with a compound of the formula (VI):

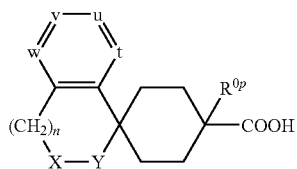
(VI)

(wherein R⁰p is hydrogen or optionally protected hydroxy; n, t, u, v, w, X and Y have each the same meaning as defined above) or its salt to give a compound of the formula (VII):

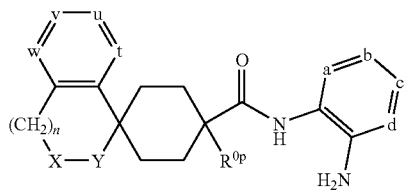
(VII)

(wherein a, b, c, d, n, R$^{Op}$, t, u, v, w, X and Y have each the same meaning as defined above), followed by subjecting the compound (VII) to intramolecular dehydrative ring closure to give a compound of the formula (VIII):

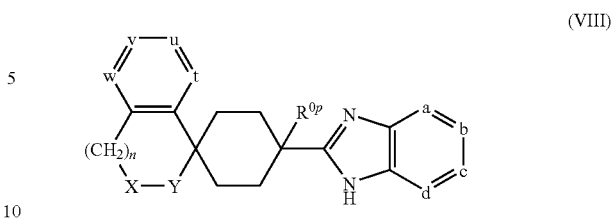
(VIII)

(wherein a, b, c, d, n, R$^{Op}$, t, u, v, w, X and Y have each the same meaning as defined above), and optionally removing wherefrom the protecting group(s) and/or oxidizing nitrogen atom(s) of the compound (VIII).

The present process refers to a process for preparing a compound of the formula (I) wherein E is methine or hydroxy substituted methine, namely a compound of the formula (I-2).

The reaction between a compound of the formula (V) and a carboxylic acid of the formula (VI) is usually carried out by employing 0.5 moles to excessive mole, preferably 1 mole to 1.5 moles of the carboxylic acid (VI), relative to 1 mole of a compound of the formula (V).

The reaction is usually carried out in an inert solvent. Preferable examples of such solvent are methylene chloride, chloroform, tetrahydrofuran, dimethyformamide, pyridine and the like, and a mixture thereof and the like.

The above reaction is preferably carried out in the presence of a condensing agent including, for example, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidino-phosphonium hexafluorophosphate, bromotris(dimethylamino)phosphonium hexafluorophosphate, diphenylphosphoric azide, 1,1'-carbonyldiimidazole and the like.

Such condensing agent can be usually used in 1 mole to excess moles, preferably 1 to 1.5 moles, relative to 1 mole of a compound of the formula (VI).

The reaction temperature is usually from −50° C. to 100° C., preferably −20° C. to 50° C.

The reaction time is usually 30 minutes to 7 days, preferably 1 to 24 hours.

In place of the carboxylic acid of the formula (VI), an activated derivative of said carboxylic acid may be reacted with a compound of the formula (V), thereby a compound of the formula (I-2) can be prepared.

Examples of such activated derivatives of the carboxylic acid of the formula (VI) are acid halides, mixed anhydrides, active esters, active amides and the like.

The acid halides of the carboxylic acid of the formula (VI) can be prepared by reacting a carboxylic acid of the formula (VI) with a halogenating agent in a conventional manner. The halogenating agent used includes, for example, thionyl chloride, phosphorus trichloride, phosphorus pentachloride, phosphorus oxychloride, phosphorus tribromide, oxalyl chloride, phosgene and the like.

The mixed anhydrides of the carboxylic acid of the formula (VI) can be prepared by reacting a carboxylic acid of the formula (VI) with an alkyl chlorocarbonate (e.g. ethyl chlorocarbonate), an aliphatic carboxylic acid chloride (e.g. pivaloyl chloride) and the like according to the conventional method.

The active esters of the carboxylic acid of the formula (VI) can be prepared by reacting a carboxylic acid of the formula (VI) with an N-hydroxy compound (e.g. N-hydroxysuccinimide, N-hydroxyphthalimide, 1-hydroxybenzotriazole); a phenol compound (e.g. 4-nitrophenol, 2,4-dinitrophenol, 2,4,5-trichlorophenol, pentachlorophenol) and the like in the presence of a condensing agent (e.g. N,N'-dicyclohexyl-carbodiimide, 1-(3-dimethylaminopropyl)-3-ethylcarbodiimide) according to the conventional method.

The active amides of the carboxylic acid of the formula (VI) can be prepared by reacting a carboxylic acid of the formula (VI) with 1,1'-carbonyldiimidazole, 1,1'-carbonylbis(2-methyl-imidazole) and the like according to the conventional method.

The reaction between a compound of the formula (V) and a reactive derivative of the carboxylic acid of the formula (VI) is usually carried out by employing 0.5 moles to excessive mole, preferably 1 mole to 1.5 moles of the reactive derivative of the carboxylic acid (VI), relative to 1 mole of compound (V).

The reaction is usually carried out in an inert solvent. Preferable examples of such inert solvent are methylene chloride, chloroform, tetrahydrofuran, dimethylformamide, pyridine and the like, and a mixture thereof and the like.

The above reaction may proceed in the absence of a base, but it is preferable to carry out the reaction in the presence of a base to promote the reaction smoothly.

The bases include organic bases (e.g. triethylamine, diisopropylethylamine, pyridine, 4-dimethylaminopyridine), or inorganic bases (e.g. sodium hydroxide, potassium hydroxide, sodium carbonate, potassium carbonate, sodium hydrogen carbonate).

It is preferable to employ 1 mole to excessive mole of said base to 1 mole of a compound of the formula (V). When the base is liquid, such base can also be used as a solvent.

The reaction temperature is usually −50° C. to 100° C. preferably −20° C. to 50° C.

The reaction time is usually 5 minutes to 7 days, preferably 30 minutes to 24 hours.

A usual treatment is carried out after completion of the reaction to obtain a crude product of a compound of formula (VII). The resulting compound of the formula (VII) may be, with or without purification according to the conventional manner, subjected to optional intramolecular ring closure condensation.

The intramolecular ring closure condensation for preparing a compound of the formula (VIII) from the compound (VII) is usually carried out in the presence of an inert solvent or without any solvent.

Preferred examples of such inert solvents are ethanol, propanol, butanol, pentanol, 1,4-dioxane, dimethoxyethane, dimethylformamide, dimethyl sulfoxide, benzene, toluene, xylene, pyridine and the like, and a mixture thereof and the like.

The reaction temperature is usually from room temperature to the boiling point of the solvent used, preferably 80° C. to 190° C.

The reaction time is usually from 5 hours to 7 days, preferably from 12 hours to 3 days.

The above ring closure may be carried out in the presence of a dehydrating agent or a catalytic-amount of Lewis acid. The dehydrating agent includes, for example, cesium fluoride, phosphorus oxychloride, phosphorus pentachloride, polyphosphoric acid, thionyl chloride and the like. As the Lewis acid, there are exemplified by scandium trifluoromethanesulfonate, yttrium trifluoromethanesulfonate, lanthanum trifluoromethanesulfonate, lanthanide trifluoromethanesulfonate and the like. The ring closure is carried out preferably without any solvent, or in the presence of a solvent such as methylene chloride, chloroform, benzene, toluene, xylene and the like or a mixture thereof.

The amount of the dehydrating agent to be used is usually 1 mole to excessive mole, preferably 2 to 10 moles, relative to 1 mole of a compound of the formula (VII), and that of the Lewis acid is 10 to 200 mole %, preferably 10 to 100 mole %.

In general, the reaction temperature is preferably from room temperature to the boiling point of the solvent used.

The reaction time is from one hour to 7 days, preferably from 5 hours to 3 days.

A compound of the formula (I-2) can be produced by treating a reaction mixture in the usual way after removal of the said protecting group(s) when the product has a protecting group after completion of the reaction, or by treating the mixture directly in the usual way when the protecting group is absent.

The removal of the protecting group(s), the oxidation of nitrogen atom(s) and the post-treatment may be conducted according to the method described in the above Production Process 1.

Production Process 3

A compound of the formula (I-2) or N-oxide derivative thereof:

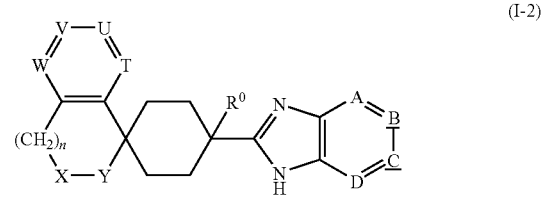

(wherein A, B, C, D, n, R⁰, T, U, V, W, X and Y have each the same meaning as defined above) can be prepared by reacting a compound of the formula (V):

(wherein a, b, c and d have each the same meaning as defined above) or its salt with a compound of the formula (IX):

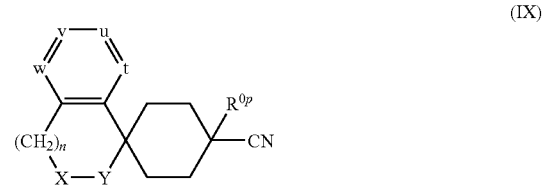

(wherein n, t, $R^{0p}$, u, v, w, X and Y have each the same meaning as defined above) or its salt to give a compound of the formula (VIII):

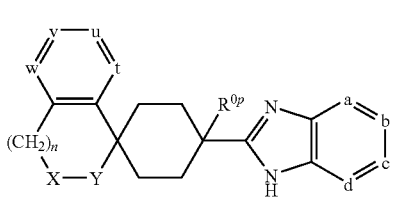

(VIII)

(wherein a, b, c, d, n, $R^{0p}$, t, u, v, w, X and Y have each the same meaning as defined above), and optionally removing wherefrom protecting group(s) and/or oxidizing nitrogen atom(s) of the compound (VIII).

The present process refers to a process for preparing a compound of the formula (I) wherein E is methine or hydroxy substituted methine, namely a compound of the formula (I-2).

The reaction between a compound of the formula (V) and a compound of the formula (IX) is usually carried out by employing 0.5 to 5 moles, preferably 0.7 to 3 moles of a compound of the formula (IX), relative to 1 mole of a compound of the formula (V).

The reaction is usually carried out in the absence of a solvent or in an inert solvent. Preferred examples of the inert solvent are benzene, toluene, xylene, methylene chloride, chloroform, hexane and the like, and a mixture thereof and the like.

The reaction temperature is usually from −20° C. to the boiling point of the solvent used, preferably 20° C. to 200° C.

The reaction time is usually from 30 minutes to 7 days, preferably from 3 hours to 3 days.

The above reaction is preferably carried out in the presence of a Lewis acid such as zinc dichloride, titanium tetrachloride, scandium trifluoromethanesulfonate, ytterbium trifluoromethanesulfonate, lanthanum trifluoromethanesulfonate and the like.

The amount of the Lewis acid used is 10 to 200 mole %, preferably 20 to 100 mole % per mole of a compound of the formula (V).

When the reaction is carried out in the presence of a Lewis acid, it is preferable to effect the reaction without any solvent, or in the presence of a solvent such as methylene chloride, chloroform, benzene, toluene, xylene and the like, or a mixture thereof and the like.

In general, the reaction temperature is from 0° C. to the boiling point of the solvent used, preferably room temperature to 150° C.

The reaction time is usually from 1 hour to 7 days, preferably 12 hours to 3 days.

A compound of the formula (I-2) can be produced by treating a reaction mixture in the usual way after removal of the said protecting group(s) when the product has a protecting group after completion of the reaction, or by treating the mixture directly in the usual way when the protecting group is absent.

The removal of the protecting group(s), the oxidation of nitrogen atom(s) and the post-treatment may be conducted according to the method described in the above Production Process 1.

Production Process 4

A compound of the formula (I-3) or N-oxide derivative thereof:

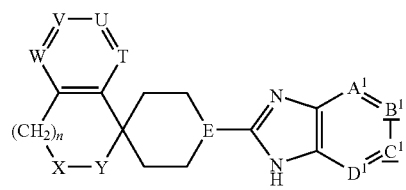

(I-3)

(wherein $A^1$, $\underline{B^1}$, $\underline{C^1}$ and $D^1$ are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N($R^1$)$R^2$ and —$Ar^1$, and at least one of $A^1$, $\underline{B^1}$, $\underline{C^1}$ and $D^1$ is said methine having a group represented by —$Ar^1$; $Ar^1$, E, n, $R^1$, $R^2$, T, U, V, W, X and Y have each the same meaning as defined above) can be prepared by reacting a compound of the formula (X):

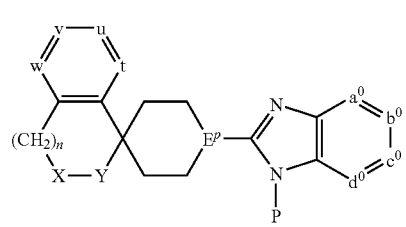

(X)

(wherein $a^0$, $b^0$, $c^0$ and $d^0$ are independently methine or nitrogen, said methine being optionally substituted by a substituent selected from the group consisting of halogen, cyano, lower alkyl, halo-lower alkyl, lower alkoxy, halo-lower alkoxy, lower alkoxycarbonyl, lower alkylsulfonyl, lower alkylsulfonyloxy, —N($R^{1p}$)$R^{2p}$ and optionally protected hydroxy, and at least one of $a^0$, $b^0$, $c^0$ and $d^0$ is said methine group having a halogen or trifluoromethanesulfonyloxy group; $E^p$ is nitrogen, methine or methine substituted by optionally protected hydroxy; and n, P, $R^{1p}$, $R^{2p}$, t, u, v, w, X and Y have each the same meaning as defined above)

with a compound of the formula (XI):

Met—$Ar^{1p}$ (XI)

(wherein Met is a common organometallic atom, and $Ar^1p$ has the same meaning as defined above) in the presence of a catalyst to give a compound of the formula (XII):

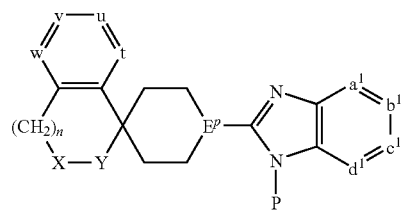

(XII)

(wherein $a^1$, $b^1$, $c^1$ and $d^1$ are independently methine or nitrogen, said methine being optionally substituted by a substituent selected from the group consisting of halogen, cyano, lower alkyl, halo-lower alkyl, lower alkoxy, halo-lower alkoxy, lower alkoxycarbonyl, lower alkylsulfonyl, lower alkylsulfonyloxy, —N($R^{1p}$)$R^{2p}$, —$Ar^1p$ and optionally protected hydroxy, and at least one of $a^1$, $b^1$, $c^1$ and $d^1$ is said methine having a group represented by —$Ar^{1p}$; and $Ar^{1p}$, $E^P$, n, P, $R^{1p}$, $R^{2p}$, t, u, v, w, X and Y have each the same meaning as defined above), and optionally removing wherefrom the protecting group(s) and/or oxidizing nitrogen atom(s) of the compound (XII).

The present process refers to a process for preparing a compound of the formula (I) wherein at least one of A, B, C and D is methine having a group represented by —$Ar^1$, namely a compound of the formula (I-3).

The common organometallic atoms represented by Met are those usually employed in the cross-coupling reaction, and include, for example, lithium, boron, silicon, magnesium, aluminum, zinc, tin and the like, among which boron, zinc, and tin are preferable. As the concrete embodiment of the practical use of such metal atoms, boron is used in the form of boric acid or boric acid ester, etc., zinc is used in the form of zinc chloride, zinc bromide or zinc iodide, etc., and tin is used in the form of tri-lower alkyl tin, etc.

The reaction between a compound of the formula (X) and a compound of the formula (XI) is usually carried out by employing 0.5 to 5 moles, preferably 0.7 to 3 moles of a compound of the formula (XI), relative to 1 mole of a compound of the formula (X).

The catalyst used in the reaction includes a transition metal generally employed in the cross-coupling reaction such as copper, nickel, palladium and the like. More precisely, preferable examples of such catalyst are tetrakis(triphenylphosphine)palladium(0), palladium(II) acetate, bis(triphenylphosphine)palladium(II) chloride, [1,1'-bis(diphenylphosphino)ferrocene]palladium(II) dichloride and the like.

The reaction is usually carried out in an inert solvent. Preferred examples of such inert solvents are water, benzene, toluene, xylene, methylene chloride, chloroform, dimethoxyethane, tetrahydrofuran, dioxane, dimethylformamide and the like, or a mixture thereof and the like.

The reaction temperature is usually from room temperature to the boiling point of the solvent used, preferably 20° C. to 200° C.

The reaction time is usually 30 minutes to 7 days, preferably 3 hours to 2 days.

The above reaction is preferably carried out in the presence of a base such as inorganic bases (e.g. sodium hydroxide, potassium hydroxide, sodium hydrogen carbonate, sodium carbonate, potassium carbonate, cesium carbonate), organic bases (e.g. triethylamine, diisopropylamine) and the like.

The amount of the base used is usually 0.5 to 5 moles, preferably 0.7 to 3 moles of said base, relative to 1 mole of a compound of the formula (X).

A compound of the formula (I-3) can be prepared by treating a reaction mixture in the usual way after removal of the said protecting group(s) when the product has a protecting group after completion of the reaction, or by treating the mixture directly in the usual way when the protecting group is absent.

The removal of the protecting group(s), the oxidation of nitrogen atom(s) and the post-treatment may be conducted according to the method described in the above Production Process 1.

The compounds of the formula (I-1), (I-2) or (I-3) may be readily isolated and purified by the conventional separation technique, and examples of such technique are solvent extraction, recrystallization, column chromatography, preparative thin layer chromatography and the like.

These compounds may be converted into the pharmaceutically acceptable salts or esters by the conventional method, and on the contrary, the conversion of the salts or esters into free compounds may also be carried out according to the conventional method.

The compounds of the formulae (II), (III), (V), (VI), (IX) and (XI) are commercially available, or can be prepared according to the common methods or analogous methods thereto, or the methods shown in Examples and Reference Examples, optionally employed in combination.

The salts of compounds of formula (III), (V), (VI) and (IX) refer to the common salts, for example, base addition salt to carboxyl group when the compound has a carboxyl group, or acid addition salt to amino or basic heterocyclyl when the compound has amino or basic heterocyclyl group(s), and the like.

Aforesaid base addition salts include salts with alkali metals (for example sodium, potassium); alkaline earth metals (for example calcium, magnesium); ammonium or organic amines (for example trimethylamine, triethylamine, dicyclohexylamine, ethanolamine, diethanolamine, triethanolamine, procaine, N,N'-dibenzylethylenediamine), and the like.

Aforesaid acid addition salts include salts with inorganic acids (for example hydrochloric acid, sulfuric acid, nitric acid, phosphoric acid, perchloric acid), organic acids (for example maleic acid, fumaric acid, tartaric acid, citric acid, ascorbic acid, trifluoroacetic acid), sulfonic acids (for example methanesulfonic acid, isethionic acid, benzenesulfonic acid, p-toluenesulfonic acid), and the like.

The utility of compounds of the present invention as a medicament is proved by the following pharmacological tests.

Pharmacological Test 1 (NPY Binding Inhibition Test)

cDNA sequence encoding human NPY Y5 receptor (c.f. International patent publication number WO96/16542) was cloned into expression vectors pcDNA3, pRc/RSV (made by Invitrogen Inc.) and pCI-neo (made by Promega Inc.). The expression vectors thus obtained were transfected to host cells COS-7, CHO and LM(tk-) (American Type Culture Collection) by cationic lipid method (Proceedings of the National Academy of Sciences of the United States of America, 84: 7413(1987)) to give NPY Y5 receptor expression cells.

A membrane sample prepared from the cells which expressed NPY Y5 receptor was incubated together with a test compound and [$^{125}$I]peptide YY (made by NEN) (20,000 cpm) in an assay buffer (25 mM Tris buffer, pH 7.4, containing 10 mM magnesium chloride, 1 mM phenylmethylsulfonyl fluoride, 0.1% bacitracin and 0.5% bovine serum albumin) at 25° C. for 2 hours, then filtered through a glass filter GF/C and washed with 5 mM Tris buffer (pH 7.4) containing 0.3% BSA. The radioactivity of the cake on the glass filter was measured. Non-specific binding was measured in the presence of 1 μM peptide YY, and a 50% Inhibitory Concentration (IC$_{50}$) of the test compound against specific peptide YY binding was determined (Endocrinology, 131: 2090(1992)). The results are shown in Table 1.

TABLE 1

| Compounds | IC$_{50}$(nM) |
| --- | --- |
| Example 6 | 2.2 |
| Example 8 | 1.8 |

TABLE 1-continued

| Compounds | IC$_{50}$(nM) |
|---|---|
| Example 13 | 2.9 |
| Example 17 | 2.7 |
| Example 20 | 2.3 |
| Example 27 | 0.72 |

As shown above, the compounds of this invention potently inhibited peptide YY (NPY homologue) binding to NPY Y5 receptors.

Pharmacological Test 2 (Antagonistic Effect on D-Trp$^{34}$NPY-Induced Feeding Behavior)

A chronic guide cannula (26 gauge, length 11 mm) was inserted stereotaxicly into the third cerebral ventricle of male SD rats (7-8 weeks old, 200-300 g) anesthetized with ketamine/xylazine (single intraperitoneal administration of 74 and 11 mg/kg) and fixed by dental resin. The top of the guide cannula was located 2.2 mm behind bregma, and 8 mm depth from the skull surface on the median line. After about 1-week recovery period, D-Trp$^{34}$NPY (1 μg/0.4 μL/head, synthetic cerebrospinal fluid containing 0.05% bovine serum albumin) was injected into the third ventricle. A test compound suspended in 0.5% aqueous methylcellulose was administered orally 2 hours before the administration of D-Trp$^{34}$NPY, and the food consumption was measured 2 hours after the administration of D-Trp$^{34}$NPY.

The results revealed that 10 mg/kg of the compound of this invention significantly suppressed the increase in food consumption induced by D-Trp$^{34}$NPY (NPY homologue) which was administered to the third ventricle.

Pharmacological Test 3 (Pharmacokinetics Test)

A test compound was orally or intravenously administered to male SD rats (7-10 weeks old, 200-400 g) which abstained from food overnight. About 100 μL of blood was collected from the tail vein at predetermined time, using a heparinized capillary. The blood was centrifuged (4° C., 6,000 r.p.m., 10 minutes) to collect the plasma, to which was added 3-fold amount of ethanol containing an internal standard. The mixture was stirred, allowed to stand at −20° C. for 20 minutes, and then centrifuged (4° C., 10,000 r.p.m., 10 minutes). The supernatant was analyzed by LC/MS/MS, and the concentration of the test compound in the plasma was measured using a relative calibration curve.

The results revealed that the bioavailability of the compound of Example 6 was 78% and its half-life in the blood was 3.0 hours.

Pharmacological Test 4 (Brain/Cerebrospinal Fluid Transport Test)

A test compound was orally or intravenously administered to male SD rats (7-10 weeks old, 200-400 g), and whole blood was collected from the abdominal aorta of said rats anesthetized with ether at predetermined time, using a heparin-treated syringe. Then, the head skin was cut open, and a dental 30 G needle was inserted between the cervical vertebrae, and it was further inserted into the cavum subarachnoideale. After 50 to 100 μL cerebrospinal fluid had been collected by a 1 ml-syringe through a tube connected to said dental 30 G needle, the brain was extracted. The blood sample was centrifuged (4° C., 6,000 r.p.m., 10 minutes) to collect the plasma, to which was added 3-fold amount of ethanol containing an internal standard, and the mixture was stirred. The brain sample was homogenized after addition of 2 ml water, an aliquot of the homogenate was taken and 3-fold amount of ethanol containing an internal standard was added thereto and stirred. The cerebrospinal fluid was stirred after adding 3-fold amount of ethanol containing an internal standard. The samples thus obtained were allowed to stand at −20° C. for 20 minutes, and then centrifuged (4° C., 12,000 g, 10 minutes). The supernatant was analyzed by LC/MS/MS, and the concentration of the test compound in the plasma, brain, and cerebrospinal fluid were measured by the method using a relative calibration curve.

The results revealed that concentrations of the compound of Example 6 in the brain, cerebrospinal fluid and plasma were 1.10 nmol/g, 0.033 μM and 2.77 μM respectively, 2 hours after oral administration (10 mg/kg).

The compounds of the formula (I) can be administered orally or parenterally and, by formulating into a suitable administrable form, may be administered as a therapeutic agent for various diseases, including, for example, cardiovascular disorders such as angina, acute or congestive heart failure, myocardial infarction, hypertension, nephropathy, electrolyte abnormality, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipidemia, gout, fatty liver, etc., genital or reproductive disorders such as infertility, preterm labor, sexual dysfunction, etc., gastro-intestinal disorders, respiratory disorder, inflammatory diseases or glaucoma, and the like, also for example, atherosclerosis, hypogonadism, hyperandrogenism, polycystic ovary syndrome, hirsutism, gastro-intestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, gallbladder diseases, cancer (breast, endometrial, colon), breathlessness, hyperuricemia, impaired fertility, low back pain, or increased anesthetic risk, and the like. In clinical use, the compounds of this invention may be administered after being formulated, together with pharmaceutically acceptable additives, into an appropriate preparation according to the mode of administration. As for said additives, those which are usually used in the field of pharmaceutical formulation may be used, for example, gelatin, lactose, sucrose, titanium oxide, starch, crystalline cellulose, hydroxypropyl methylcellulose, carboxymethylcellulose, corn starch, microcrystalline wax, white petrolatum, magnesium methasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hydrogenated castor oil, polyvinylpyrrolidone, magnesium stearate, light silicic anhydride, talc, vegetable oil, benzyl alcohol, gum arabic, propylene glycol, polyalkylene glycol, cyclodextrin or hydroxypropyl cyclodextrin and the like.

A mixture with said additives may be formulated into the form of solid preparations (for example tablets, capsules, granules, powder, suppositories); or liquid preparations (for example syrups, elixirs, injections). Such preparations may be formulated according to the techniques well-known in the art of pharmaceutical formulation. Liquid preparations may be in the form of preparations which are dissolved or suspended in water or other appropriate media when used, and injectable preparations in particular may be dissolved or suspended in physiological saline or glucose solution if necessary, optionally together with a buffer and a preservative.

When compounds of this invention are used clinically, for example, a daily dose for an adult is 0.01-100 mg/kg, preferably 0.03-1 mg/kg with simultaneous or divided administration when administered orally, and 0.001-10 mg/kg, preferably 0.001-0.1 mg/kg, more preferably 0.01-0.1 mg/kg with simultaneous or divided administration when administered parenterally, though the dose and the frequency of dosage may vary depending upon the sex, age, body weight, the degree of symptoms and the kind and range of the desired treatment effects.

An ordinarily skilled physician, veterinarian or clinician can readily determine and prescribe the effective amount of the drug required to prevent, suppress or arrest the progress of diseases.

All the said preparations may contain 1.0 to 100 wt. %, preferably 1.0 to 60 wt. % of compounds of this invention and may also contain other therapeutically effective compounds.

The compounds of the present invention can be used in combination with other agents useful for treating metabolic disorders and/or eating disorders. The individual component of such combinations can be administered separately at different times or concurrently in divided or single combination forms during the course of therapy. The instant invention is therefore to be understood as embracing all such regimes of simultaneous or divided administration and the term "administering" is to be interpreted accordingly. The scope of combinations of the compounds of this invention with other agents useful for treating metabolic disorders and/or eating disorders includes in principle any combination of any pharmaceutical composition useful for treating metabolic disorders and/or eating disorders.

Diabetes is caused by multiple factors and is most simply characterized by elevated levels of plasma glucose (hyperglycemia) in the fasting state. There are two generally recognized forms of diabetes: type 1 diabetes, or insulin-dependent diabetes mellitus (IDDM), in which patients produce little or no insulin, the hormone which regulates glucose utilization, and type 2 diabetes, or noninsulin-dependent diabetes mellitus (NIDDM), wherein patients produce insulin and even exhibit hyperinsulinemia (plasma insulin levels that are the same or even elevated in comparison with non-diabetic subjects), while at the same time demonstrating hyperglycemia. Type 1 diabetes is typically treated with exogenous insulin administered via injection. However, type 2 diabetics often develop "insulin resistance", such that the effect of insulin in stimulating glucose and lipid metabolism in the main insulin-sensitive tissues, namely, muscle, liver and adipose tissues, is diminished. Patients who are insulin resistant but not diabetic have elevated insulin levels that compensate for their insulin resistance, so that serum glucose levels are not elevated. In patients with NIDDM, the plasma insulin levels, even when they are elevated, are insufficient to overcome the pronounced insulin resistance, resulting in hyperglycemia.

Insulin resistance is primarily due to a receptor binding defect that is not yet completely understood. Resistance to insulin results in insufficient activation of glucose uptake, diminished oxidation of glucose and storage of glycogen in muscle, inadequate insulin repression of lipolysis in adipose tissue and inadequate glucose production and secretion by the liver.

The persistent or uncontrolled hyperglycemia that occurs in diabetics is associated with increased morbidity and premature mortality. Type 2 diabetics are at increased risk of developing cardiovascular complications, e.g., atherosclerosis, coronary heart disease, stroke, peripheral vascular disease, hypertension, nephropathy, neuropathy and retinopathy.

Non-insulin dependent diabetes is also associated with cardiac hypertrophy, in particular left ventricular hypertrophy (Devereux, R. B., Circulation, 101:2271-2276 (2000)). Cardiac hypertrophy, such as left ventricular hypertrophy, is due to the response of the heart to chronic pressure or volume overload. Left ventricular hypertrophy (LVH) is characterized by thickening of the left ventricular wall, including increased left ventricular mass and increased left ventricular wall thickness, and is defined as a left ventricular mass index exceeding 131 $g/m^2$ of the body surface area in men, and 100 $g/m^2$ in women (Savage et al., The Framingham Study, Circulation, 75 (1 Pt 2): 26-33 (1987).

Left ventricular hypertrophy is independently associated with increased incidence of cardiovascular disease, such as congestive heart failure, ischaemic heart disease, cardiovascular and all-cause mortality, sudden death, and stroke. Regression of left ventricular hypertrophy has been associated with a reduction in cardiovascular risk. It has also been found that the incidence of morbid events in patients with progression of left ventricular hypertrophy is greater than in patients with regression of left ventricular hypertrophy.

Current treatments for hypertrophy include non-pharmacological interventions, such as weight reduction, sodium restriction, and aerobic physical exercise can reduce left ventricular mass (Ghali, J. K. et al., American Journal of Geriatric Cardiology, 6:38-49 (1997).

Many patients who have insulin resistance but have not yet developed type 2 diabetes are also at a risk of developing metabolic syndrome, also referred to as syndrome X, insulin resistance syndrome, or plurimetabolic syndrome. The period of 5 to 10 years preceding the development of impaired glucose tolerance is associated with a number of hormonal imbalances, which give rise to an enlargement of visceral fat mass, hypertension, insulin resistance, and hyperlipidemia (Bjornstop, P., Current Topics in Diabetes Research, eds. Belfore, F., Bergman, R. N., and Molinath, G. M., Front Diabetes, Basel, Karger, 12:182-192 (1993)). Similarly, metabolic syndrome is characterized by insulin resistance, along with abdominal obesity, hyperinsulinemia, high blood pressure, low HDL and high VLDL. Although the causal relationship between the various components of metabolic syndrome remains to be confirmed, insulin resistance appears to play an important role (Requen, G. M., et al., N. Eng. J. Med. 334:374-381 (1996); Despres, J-P., et al., N. Engl. J. Med. 334:952-957 (1996); Wajchenberg, B. L., et al., Diabetes/Metabolism Rev. 10:19-29 (1994)). Metabolic syndrome patients, whether or not they develop overt diabetes mellitus, are at increased risk of developing the cardiovascular complications listed above. Associations have also been found between left ventricular hypertrophy and metabolic syndrome (Marcus, R. et al. Circulation, 90:928-936 (1994); Lind, L. et al., J Hypertens. 13:433-38 (1995); Paolisso, G et al., Am J Hypertens., 10:1250-1256 (1997).

Diabetes is treated with a variety of therapeutic agents including insulin sensitizers, such as PPARγ agonists, such as glitazones; biguanides; protein tyrosine phosphatase-1B inhibitors; dipeptidyl peptidase IV inhibitors; insulin; insulin mimetics; sulfonylureas; meglitinides; α-glucoside hydrolase inhibitors; and α-amylase inhibitors.

Increasing the plasma level of insulin by administration of sulfonylureas (e.g. tolbutamide and glipizide) or meglitinides, which stimulate the pancreatic β-cells to secrete more insulin, and/or by injection of insulin when sulfonylureas or meglitinides become ineffective, can result in insulin concentrations high enough to stimulate insulin-resistant tissues. However, dangerously low levels of plasma glucose can result, and increasing insulin resistance due to the even higher plasma insulin levels can occur. The biguanides increase insulin sensitivity resulting in some correction of hyperglycemia. Metformin monotherapy is often used for treating type 2 diabetic patients who are also obese and/or dyslipidemic. Lack of appropriate response to metformin is often followed by treatment with sulfonylureas, thiazolidinediones, insulin, or alpha glucosidase inhibitors. However, the two biguanides, phenformin and metformin, can also induce lactic acidosis and nausea/diarrhea, respectively. Alpha glucosidase inhibitors, such as acarbose, work by delaying absorption of glucose in the intestine. Alpha-amylase inhibitors inhibit the enzymatic degradation of starch or glycogen into maltose, which also reduces the amounts of bioavailable sugars.

The glitazones, also known as thiazolidinediones (i.e. 5-benzylthiazolidine-2,4-diones), are a more recently described class of compounds with potential for a novel mode of action in ameliorating many symptoms of type 2 diabetes. These agents substantially increase insulin sensitivity in muscle, liver and adipose tissue in several animal models of type 2 diabetes resulting in partial or complete correction of the elevated plasma levels of glucose without occurrence of hypoglycemia. The glitazones that are currently marketed are agonists of the peroxisome proliferator activated receptor (PPAR) gamma subtype. PPAR-gamma agonism is generally believed to be responsible for the improved insulin sensitization that is observed with the glitazones. Newer PPAR agonists that are being developed for treatment of Type 2 diabetes and/or dyslipidemia are agonists of one or more of the PPAR alpha, gamma and delta subtypes.

However, treatment of diabetes with PPAR γ agonists has been associated with cardiac hypertrophy, or an increase in heart weight. Recent labeling revisions for Avandia (rosiglitazone maleate), a PPARγ agonist, indicate that patients may experience fluid accumulation and volume-related events such as edema and congestive heart failure. Cardiac hypertrophy related to PPARγ agonist treatment is typically treated by withdrawing PPAR treatment.

Treatment of type 2 diabetes also typically includes physical exercise, weight control and dieting. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. However, weight reduction and increased exercise are difficult for most people with diabetes.

Abnormal glucose homeostasis is also associated both directly and indirectly with obesity, hypertension and alterations in lipid, lipoprotein and apolipoprotein metabolism. Obesity increases the likelihood of insulin resistance, and increases the likelihood that the resulting insulin resistance will increase with increasing body weight. Therefore, therapeutic control of glucose homeostasis, lipid metabolism, obesity and hypertension are critically important in the clinical management and treatment of diabetes mellitus.

Obesity, which can be defined as a body weight more than 20% above the ideal body weight, is a major health concern in Western societies. It is estimated that about 97 million adults in the United States are overweight or obese. Obesity is the result of a positive energy balance, as a consequence of increased ratio of caloric intake to energy expenditure. The molecular factors regulating food intake and body weight balance are incompletely understood. [B. Staels et al., J. Biol. Chem. 270(27), 15958 (1995); F. Lonnquist et al., Nature Medicine 1(9), 950 (1995)]. Although the genetic and/or environmental factors leading to obesity are poorly understood, several genetic factors have been identified.

Epidemiological studies have shown that increasing degrees of overweight and obesity are important predictors of decreased life expectancy. Obesity causes or exacerbates many health problems, both independently and in association with other diseases. The medical problems associated with obesity, which can be serious and life-threatening, include type 2 diabetes mellitus, hypertension, elevated plasma insulin concentrations, insulin resistance, dyslipidemias, hyperlipidemia, endometrial, breast, prostate, kidney and colon cancer, osteoarthritis; respiratory complications, such as obstructive sleep apnea, gallstones, arterioscelerosis, heart disease, abnormal heart rhythms, and heart arrythmias (Kopelman, P. G., Nature 404, 635-643 (2000)). Obesity is also associated with metabolic syndrome, cardiac hypertrophy, in particular left ventricular hypertrophy, premature death, and with a significant increase in mortality and morbidity from stroke, myocardial infarction, congestive heart failure, coronary heart disease, and sudden death.

Abdominal obesity has been linked with a much higher risk of coronary artery disease, and with three of its major risk factors: high blood pressure, diabetes that starts in adulthood, and high levels of fats (lipids) in the blood. Losing weight dramatically reduces these risks. Abdominal obesity is further closely associated with glucose intolerance, hyperinsulinemia, hypertriglyceridemia, and other disorders associated with metabolic syndrome (syndrome X), such as raised high blood pressure, decreased levels of high density lipoproteins (HDL) and increased levels of very low density lipoproteins (VLDL) (Montague et al., Diabetes, 2000, 49: 883-888).

Obesity and obesity-related disorders, such as diabetes, are often treated by encouraging patients to lose weight by reducing their food intake or by increasing their exercise level, thereby increasing their energy output. A sustained weight loss of 5% to 10% of body weight has been shown to improve the comorbidities associated with obesity, such as diabetes, and can lead to improvement of obesity-related disorders such as diabetes, left ventricular hypertrophy, osteoarthritis, and pulmonary and cardiac dysfunction.

Weight loss drugs used for the treatment of obesity include orlistat (Davidson, M. H. et al. (1999) JAMA 281:235-42), dexfenfluramine (Guy Grand, B. et al. (1989) Lancet 2:1142-5), sibutramine (Bray, G. A. et al. (1999) Obes. Res. &:189-98) and phentermine (Douglas, A. et al. (1983) Int. J. Obes. 7:591-5). However, the side effects of these drugs and anti-obesity agents may limit their use. Dexfenfluramine was withdrawn from the market because of suspected heart valvulopathy; orlistat is limited by gastrointestinal side effects; and the use of sibutramine is limited by its cardiovascular side effects which have led to reports of deaths and its withdrawal from the market in Italy.

The term "diabetes," as used herein, includes both insulin-dependent diabetes mellitus (i.e., IDDM, also known as type 1 diabetes) and non-insulin-dependent diabetes mellitus (i.e., NIDDM, also known as Type 2 diabetes). Type 1 diabetes, or insulin-dependent diabetes, is the result of an absolute deficiency of insulin, the hormone which regulates glucose utilization. Type 2 diabetes, or insulin-independent diabetes (i.e., non-insulin-dependent diabetes mellitus), often occurs in the face of normal, or even elevated levels of insulin and appears to be the result of the inability of tissues to respond appropriately to insulin. Most of the Type 2 diabetics are also obese. The compositions of the present invention are useful for treating both Type 1 and Type 2 diabetes. The compositions are especially effective for treating Type 2 diabetes. The compositions of the present invention are also useful for treating and/or preventing gestational diabetes mellitus.

Treatment of diabetes mellitus refers to the administration of a compound or combination of the present invention to treat diabetes. One outcome of treatment may be decreasing the glucose level in a subject with elevated glucose levels. Another outcome of treatment may be decreasing insulin levels in a subject with elevated insulin levels. Another outcome of treatment is decreasing plasma triglycerides in a subject with elevated plasma triglycerides. Another outcome of treatment is decreasing LDL cholesterol in a subject with high LDL cholesterol levels. Another outcome of treatment is increasing HDL cholesterol in a subject with low HDL cholesterol levels. Another outcome of treatment is increasing insulin sensitivity. Another outcome of treatment may be enhancing glucose tolerance in a subject with glucose intolerance. Yet another outcome of treatment may be decreasing insulin resistance in a subject with increased insulin resistance or elevated levels of insulin.

Prevention of diabetes mellitus refers to the administration of a compound or combination of the present invention to prevent the onset of diabetes in a subject in need thereof.

The term "hypertension" as used herein includes essential, or primary, hypertension wherein the cause is not known or where hypertension is due to greater than one cause, such as changes in both the heart and blood vessels; and secondary hypertension wherein the cause is known. Causes of secondary hypertension include, but are not limited to obesity; kidney disease; hormonal disorders; use of certain drugs, such as oral contraceptives, corticosteroids, cyclosporin, and the like. The term "hypertension" encompasses high blood pressure, in which both the systolic and diastolic pressure levels are elevated, and isolated systolic hypertension, in which only the systolic pressure is elevated to greater than or equal to 140 mm Hg, while the diastolic pressure is less than 90 mm Hg. One outcome of treatment is decreasing blood pressure in a subject with high blood pressure.

Dyslipidemias or disorders of lipid metabolism, include various conditions characterized by abnormal concentrations of one or more lipids (i.e. cholesterol and triglycerides), and/or apolipoproteins (i.e., apolipoproteins A, B, C and E), and/or lipoproteins (i.e., the macromolecular complexes formed by the lipid and the apolipoprotein that allow lipids to circulate in blood, such as LDL, VLDL and IDL). Hyperlipidemia is associated with abnormally high levels of lipids, LDL and VLDL cholesterol, and/or triglycerides.

The term "metabolic syndrome", also known as syndrome X, is defined in the Third Report of the National Cholesterol Education Program Expert Panel on Detection, Evaluation and Treatment of High Blood Cholesterol in Adults (ATP-III). E. S. Ford et al., JAMA, vol. 287 (3), Jan. 16, 2002, pp 356-359. Briefly, a person is defined as having metabolic syndrome if the person has three or more of the following symptoms: abdominal obesity, hypertriglyceridemia, low HDL cholesterol, high blood pressure, and high fasting plasma glucose. The criteria for these are defined in ATP-III.

The term "left ventricular hypertrophy" (LVH) as used herein includes three patterns of left ventricular hypertrophy that have been identified based on left ventricular mass index (LVMI=left ventricular mass in grams divided by body surface area in meters 2) and relative wall thickness (RWT=2× posterior wall thickness/left ventricular end diastolic diameter). Concentric LVH is typically exemplified by a left ventricular mass index of 144 and a relative wall thickness of 0.52; eccentric LVH is typically exemplified by a left ventricular mass index of 136 and a relative wall thickness of 0.38; and concentric left ventricular remodeling which is typically exemplified by a LVMI of 93 and a relative wall thickness of 0.49. Normal LVMI are typically 85 and normal RWT approximately 0.36. Patients with concentric left ventricular (LV) remodeling have a cardiovascular risk intermediate between those with normal left ventricular structure and those with left ventricular hypertrophy.

One outcome of treatment of diabetes while minimizing cardiac hypertrophy, or left ventricular hypertrophy, may be a decrease in ventricular mass. Another outcome of treatment of diabetes while minimizing cardiac hypertrophy or left ventricular hypertrophy may be a decrease in the rate of increase of ventricular mass. Another outcome of treatment of diabetes while minimizing cardiac hypertrophy or left ventricular hypertrophy may be a decrease in ventricular wall thickness. Another outcome of treatment of diabetes while minimizing cardiac hypertrophy of left ventricular hypertrophy may be the decrease in the rate of increase in ventricular wall thickness.

The term "obesity" as used herein is a condition in which there is an excess of body fat. The operational definition of obesity is based on the Body Mass Index (BMI), which is calculated as body weight per height in meters squared (kg/m$^2$). "Obesity" refers to a condition whereby an otherwise healthy subject has a Body Mass Index (BMI) greater than or equal to 30 kg/m$^2$, or a condition whereby a subject with at least one co-morbidity has a BMI greater than or equal to 27 kg/m$^2$. An "obese subject" is an otherwise healthy subject with a Body Mass Index (BMI) greater than or equal to 30 kg/m$^2$ or a subject with at least one co-morbidity with a BMI greater than or equal to 27 kg/m$^2$. A "subject at risk of obesity" is an otherwise healthy subject with a BMI of 25 kg/m$^2$ to less than 30 kg/m$^2$ or a subject with at least one co-morbidity with a BMI of 25 kg/m$^2$ to less than 27 kg/m$^2$.

The increased risks associated with obesity occur at a lower Body Mass Index (BMI) in Asians. In Asian countries, including Japan, "obesity" refers to a condition whereby a subject with at least one obesity-induced or obesity-related co-morbidity, that requires weight reduction or that would be improved by weight reduction, has a BMI greater than or equal to 25 kg/m$^2$. In Asian countries, including Japan, an "obese subject" refers to a subject with at least one obesity-induced or obesity-related co-morbidity that requires weight reduction or that would be improved by weight reduction, with a BMI greater than or equal to 25 kg/m$^2$. In Asia-Pacific, a "subject at risk of obesity" is a subject with a BMI of greater than 23 kg/m$^2$ to less than 25 kg/m$^2$.

As used herein, the term "obesity" is meant to encompass all of the above definitions of obesity.

Obesity-induced or obesity-related co-morbidities include, but are not limited to, diabetes, non-insulin dependent diabetes mellitus—type 2, diabetes associated with obesity, impaired glucose tolerance, impaired fasting glucose, insulin resistance syndrome, dyslipidemia, hypertension, hypertension associated with obesity, hyperuricacidemia, gout, coronary artery disease, myocardial infarction, angina pectoris, sleep apnea syndrome, Pickwickian syndrome, fatty liver; cerebral infarction, cerebral thrombosis, transient ischemic attack, orthopedic disorders, arthritis deformans, lumbodynia, emmeniopathy, and infertility. In particular, co-morbidities include: hypertension, hyperlipidemia, dyslipidemia, glucose intolerance, cardiovascular disease, sleep apnea, diabetes mellitus, and other obesity-related conditions.

Treatment of obesity and obesity-related disorders refers to the administration of the compounds or combinations of the present invention to reduce or maintain the body weight of an obese subject. One outcome of treatment may be reducing the body weight of an obese subject relative to that subject's body weight immediately before the administration of the compounds or combinations of the present invention. Another outcome of treatment may be preventing body weight regain of body weight previously lost as a result of diet, exercise, or pharmacotherapy. Another outcome of treatment may be decreasing the occurrence of and/or the severity of obesity-related diseases. The treatment may suitably result in a reduction in food or calorie intake by the subject, including a reduction in total food intake, or a reduction of intake of specific components of the diet such as carbohydrates or fats; and/or the inhibition of nutrient absorption; and/or the inhibition of the reduction of metabolic rate; and in weight reduction in patients in need thereof. The treatment may also result in an alteration of metabolic rate, such as an increase in metabolic rate, rather than or in addition to an inhibition of the reduction of metabolic rate; and/or in minimization of the metabolic resistance that normally results from weight loss.

Prevention of obesity and obesity-related disorders refers to the administration of the compounds or combinations of the present invention to reduce or maintain the body weight of a subject at risk of obesity. One outcome of prevention may be reducing the body weight of a subject at risk of obesity relative to that subject's body weight immediately before the administration of the compounds or combinations of the present invention. Another outcome of prevention may be preventing body weight regain of body weight previously lost as a result of diet, exercise, or pharmacotherapy. Another outcome of prevention may be preventing obesity from occurring if the treatment is administered prior to the onset of obesity in a subject at risk of obesity. Another outcome of prevention may be decreasing the occurrence and/or severity of obesity-related disorders if the treatment is administered prior to the onset of obesity in a subject at risk of obesity. Moreover, if treatment is commenced in already obese subjects, such treatment may prevent the occurrence, progression or severity of obesity-related disorders, such as, but not limited to, arteriosclerosis, Type 2 diabetes, polycystic ovary disease, cardiovascular diseases, osteoarthritis, dermatological disorders, hypertension, insulin resistance, hypercholesterolemia, hypertriglyceridemia, and cholelithiasis.

The term "atherosclerosis" as used herein encompasses vascular diseases and conditions that are recognized and understood by physicians practicing in the relevant fields of medicine. Atherosclerotic cardiovascular disease, coronary heart disease (also known as coronary artery disease or ischemic heart disease), cerebrovascular disease and peripheral vessel disease are all clinical manifestations of atherosclerosis and are therefore encompassed by the terms "atherosclerosis" and "atherosclerotic disease." The combination comprised of a therapeutically effective amount of an anti-obesity agent in combination with a therapeutically effective amount of an anti-diabetic agent may be administered to prevent or reduce the risk of occurrence, or recurrence where the potential exists, of a coronary heart disease event, a cerebrovascular event, or intermittent claudication. Coronary heart disease events are intended to include CHD death, myocardial infarction (i.e., a heart attack), and coronary revascularization procedures. Cerebrovascular events are intended to include ischemic or hemorrhagic stroke (also known as cerebrovascular accidents) and transient ischemic attacks. Intermittent claudication is a clinical manifestation of peripheral vessel disease. The term "atherosclerotic disease event" as used herein is intended to encompass coronary heart disease events, cerebrovascular events, and intermittent claudication. It is intended that persons who have previously experienced one or more non-fatal atherosclerotic disease events are those for whom the potential for recurrence of such an event exists.

Circadian rhythms affect a variety of physiological parameters: rest-activity, sleep-wake cycles, body temperature, rhythms in hormone levels, oscillations in general physiology and the like. When these parameters are out of synchrony with the daily clock, a circadian rhythm imbalance occurs which can affect physiology, performance on a variety of tasks and one's emotional well being. The present invention is useful, for example, in the prevention or treatment of conditions associated with circadian rhythmicity as well as mental and physical disorders associated with travel across time zones and with rotating shift-work schedules.

In another embodiment, the present invention provides a method for the prevention or treatment of a circadian rhythm disorder in a mammal, including time-zone change (jet-lag) syndrome, shift-work sleep disorder, delayed sleep-phase syndrome, advanced sleep-phase syndrome, and non-24-hour sleep-wake disorder, which comprises administering to the mammal an effective amount of a NPY Y5 receptor antagonist.

In another embodiment, the present invention provides a method for shortening the time of re-entrainment (return to normal entrainment of the circadian rhythms; synchronized to the environmental light-dark cycle) in a subject following a shift in the sleep-wake cycle which comprises administering to the subject an appropriate amount of a NPY Y5 antagonist.

In another embodiment, the present invention provides a method for alleviating the effects of jet lag in a traveler, especially a mammal, which comprises administering to the traveler an alertness increasing amount of a NPY Y5 antagonist. The purpose of this embodiment is to assist the body to adjust physiologically to the changes in sleep and feeding patterns when crossing several time zones.

In another more preferred embodiment, the present invention provides a method for resetting the internal circadian clock in a subject to match the subject's current activity/sleep cycle. For example shift workers changing from a day to a night shift or vice versa, which comprises administering to the subject an appropriate amount of a NPY Y5 antagonist.

The present invention is further directed to the use of NPY Y5 antagonist, for enhancing or improving sleep quality as well as preventing and treating sleep disorders and sleep disturbances in a mammal. In particular, the present invention provides a method for enhancing or improving sleep quality by increasing sleep efficiency and augmenting sleep maintenance. In addition, the present invention provides a method for preventing and treating sleep disorders and sleep disturbances in a mammal which comprising the administration of a NPY Y5 antagonist. The present invention further provides a pharmaceutical composition for enhancing or improving sleep quality and increasing sleep efficiency and sleep maintenance. The present invention is useful for the treatment of sleep disorders, including Disorders of Initiating and Maintaining Sleep (insomnias) ("DIMS") which can arise from psychophysiological causes, as a consequence of psychiatric disorders (particularly related to anxiety), from drugs and alcohol use and abuse (particularly during withdrawal stages), childhood onset DIMS, nocturnal myoclonus and restless legs and non specific REM disturbances as seen in ageing.

The following outcomes in a subject which are provided by the present invention may be correlated to enhancement in sleep quality: an increase in the value which is calculated from the time that a subject sleeps divided by the time that a subject is attempting to sleep; a decrease in sleep latency (the time it takes to fall asleep); a decrease in the number of awakenings during sleep; a decrease in the time spent awake following the initial onset of sleep; an increase in the total amount of sleep; an increase the amount and percentage of REM sleep; an increase in the duration and occurrence of REM sleep; a reduction in the fragmentation of REM sleep; an increase in the amount and percentage of slow-wave (i.e. stage 3 or 4) sleep; an increase in the amount and percentage of stage 2 sleep; a decrease in the number of awakenings, especially in the early morning; an increase in daytime alertness; and increased sleep maintenance. Secondary outcomes which may be provided by the present invention include enhanced cognitive function and increased memory retention. A "method for enhancing the quality of sleep" refers to a method that results in outcomes in a subject which may be correlated to enhancement in sleep quality, including, but not limited to, the outcomes correlated to enhancement of sleep quality as defined above.

The present invention is further useful for the prevention and treatment of sleep disorders and sleep disturbances including sleep problems associated with insomnia, hypersomnia, sleep apnea, narcolepsy, nocturnal myoclonus, REM sleep interruptions, jet-lag, shift workers' sleep disturbances, dysomnias, night terror, night eating syndrome, insomnias associated with depression or with emotional/mood disorders, dysfunctions associated with sleep (parasomnias), as well as sleep walking and enuresis, as well as sleep disorders which accompany aging. Sleep disorders and sleep disturbances are generally characterized by difficulty in initiating or maintaining sleep or in obtaining restful or enough sleep.

In addition, certain drugs may also cause reductions in REM sleep as a side effect and the present invention may be used to correct those types of sleeping disorders as well. The present invention would also be of benefit in the treatment of syndromes such as fibromyalgia which are manifested by non-restorative sleep and muscle pain or sleep apnea which is associated with respiratory disturbances during sleep. It will be clear to one skilled in the art that the present invention is not limited to just sleep disorders and sleep disturbances, but is applicable to a wide variety of conditions which result from a diminished quality of sleep.

The present invention is also concerned with treatment and prevention of these conditions, and with the use of a NPY Y5 antagonist, combinations, and compositions thereof, for the manufacture of a medicament useful for treating or preventing these conditions.

In the present invention, it is preferred that the subject mammal is a human. Although the present invention is applicable both old and young people, it may find greater application in elderly people. Further, although the invention may be employed to enhance the sleep of healthy people, it may be especially beneficial for enhancing the sleep quality of people suffering from sleep disorders or sleep disturbances.

The compositions of the present invention may be used in combination with other drugs that may also be useful in the treatment, prevention, or control of disorders, such as hypertension, hypertension associated with obesity, hypertension-related disorders, cardiac hypertrophy, left ventricular hypertrophy, and metabolic syndrome, obesity and obesity-related disorders, for which compounds comprising the compositions are useful. Such other drugs may be administered, by a route and in an amount commonly used therefore, contemporaneously or sequentially with a composition of the present invention. When a composition of the present invention is used contemporaneously with one or more other drugs, a pharmaceutical composition in unit dosage form containing such other drugs and the composition of the present invention is preferred. However, the combination therapy also includes therapies in which the composition of the present invention and one or more other drugs are administered on different overlapping schedules. It is also contemplated that when used in combination with one or more other active ingredients, the composition of the present invention and the other active ingredients may be used in lower doses than when each is used singly. Accordingly, the pharmaceutical compositions of the present invention include those that contain one or more other active ingredients, in addition to a composition of the present invention.

Examples of other active ingredients that may be administered in combination with a composition of the present invention, and either administered separately or in the same pharmaceutical composition, include, but are not limited to:

(a) anti-diabetic agents such as (i) PPARγ agonists such as glitazones (e.g. ciglitazone; darglitazone; englitazone; isaglitazone (MCC-555); pioglitazone; rosiglitazone; troglitazone; BRL49653; CLX-0921; 5-BTZD, and the like), and GW-0207, LG-100641, and LY-300512, and the like; (ii) biguanides such as buformin; metformin; and phenformin, and the like; (iii) protein tyrosine phosphatase-1B (PTP-1B) inhibitors; (iv) sulfonylureas such as acetohexamide; chlorpropamide; diabinese; glibenclamide; glipizide; glyburide; glimepiride; gliclazide; glipentide; gliquidone; glisolamide; tolazamide; and tolbutamide, and the like; (v) meglitinides such as repaglinide, and nateglinide, and the like; (vi) alpha glucoside hydrolase inhibitors such as acarbose; adiposine; camiglibose; emiglitate; miglitol; voglibose; pradimicin-Q; salbostatin; CKD-711; MDL-25,637; MDL-73,945; and MOR 14, and the like; (vii) alpha-amylase inhibitors such as tendamistat, trestatin, and Al-3688, and the like; (viii) insulin secreatagogues such as linogliride; and A-4166, and the like; (ix) fatty acid oxidation inhibitors, such as clomoxir, and etomoxir, and the like; (x) A2 antagonists, such as midaglizole; isaglidole; deriglidole; idazoxan; earoxan; and fluparoxan, and the like; (xi) insulin or insulin mimetics, such as biota, LP-100, novarapid, insulin detemir, insulin lispro, insulin glargine, insulin zinc suspension (lente and ultralente); Lys-Pro insulin, GLP-1 (73-7) (insulintropin); and GLP-1 (7-36)-NH$_2$), and the like; (xii) non-thiazolidinediones such as JT-501, and farglitazar (GW-2570/GI-262579), and the like; (xiii) PPARα/γ dual agonists such as MK-0767, CLX-0940, GW-1536, GW1929, GW-2433, KRP-297, L-796449, LR-90, and SB 219994, and the like; (xiv) other insulin sensitizing drugs; and (xv) VPAC2 receptor agonists;

(b) lipid lowering agents such as (i) bile acid sequestrants such as, cholestyramine, colesevelem, colestipol, dialkylaminoalkyl derivatives of a cross-linked dextran; Colestid®; LoCholest®; and Questran®, and the like; (ii) HMG-CoA reductase inhibitors such as atorvastatin, itavastatin, fluvastatin, lovastatin, pravastatin, rivastatin, rosuvastatin, simvastatin, and ZD-4522, and the like; (iii) HMG-CoA synthase inhibitors; (iv) cholesterol absorption inhibitors such as stanol esters, beta-sitosterol, sterol glycosides such as tiqueside; and azetidinones such as ezetimibe, and the like; (v) acyl coenzyme A-cholesterol acyl transferase (ACAT) inhibitors such as avasimibe, eflucimibe, KY505, SMP 797, and the like; (vi) CETP inhibitors such as JTT 705, torcetrapib, CP 532,632, BAY63-2149, SC 591, SC 795, and the like; (vii) squalene, synthetase inhibitors; (viii) anti-oxidants such as probucol, and the like; (ix) PPARα agonists such as beclofibrate, benzafibrate, ciprofibrate, clofibrate, etofibrate, fenofibrate, gemcabene, and gemfibrozil, GW7647, BM170744, LY518674; and other fibric acid derivatives, such as Atromid®, Lopid® and Tricor®, and the like; (x) FXR receptor modulators such as GW 4064, SR 103912, and the like; (xi) LXR receptor such as GW 3965, T9013137, and XTC0179628, and the like; (xii) lipoprotein synthesis inhibitors such as niacin; (xiii) renin angiotensin system inhibitors; (xiv) PPARδ partial agonists; (xv) bile acid reabsorption inhibitors, such as BARI 1453, SC435, PHA384640, S8921, AZD7706, and the like; (xvi) PPARδ agonists such as GW 501516, and GW 590735, and the like; (xvii) triglyceride synthesis inhibitors; (xviii) microsomal triglyceride transport (MTTP) inhibitors, such as inplitapide, LAB687, and CP346086, and the like; (xix) transcription modulators; (xx) squalene epoxidase inhibitors; (xxi) low density lipoprotein (LDL) receptor inducers; (xxii) platelet aggregation inhibitors; (xxiii) 5-LO or FLAP inhibitors; and (xiv) niacin receptor agonists; and (c) anti-hypertensive agents such as (i) diuretics, such as thiazides, including chlorthalidone, chlorthiazide, dichlorophenamide, hydroflumethiazide, indapamide, and hydrochlorothiazide; loop diuretics, such as bumetanide, ethacrynic acid, furosemide, and torsemide; potassium sparing agents, such as amiloride, and triamterene; and aldosterone antagonists, such as spironolactone, epirenone, and the like; (ii) beta-adrenergic blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tertatolol, tilisolol, and timolol, and the like; (iii) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, and verapamil, and the like; (iv) angiotensin converting enzyme (ACE) inhibitors such as benazepril; captopril; cilazapril; delapril; enalapril; fosinopril; imidapril; losinopril; moexipril; quinapril; quinaprilat; ramipril; perindopril; perindropril; quanipril; spirapril; tenocapril; trandolapril, and zofenopril, and the like; (v) neutral endopeptidase inhibitors such as omapatrilat, cadoxatril and ecadotril, fosidotril, sampatrilat, AVE7688, ER4030, and the like; (vi) endothelin antagonists such as tezosentan, A308165, and YM62899, and the like; (vii) vasodilators such as hydralazine, clonidine, minoxidil, and nicotinyl alcohol, and the like; (viii) angiotensin II receptor antagonists such as candesartan, eprosartan, irbesartan, losartan, pratosartan, tasosartan, telmisartan, valsartan, and EXP-3137, FI6828K, and RNH6270, and the like; (viv) α/β adrenergic blockers as nipradilol, arotinolol and amosulalol, and the like; (x) alpha 1 blockers, such as terazosin, urapidil, prazosin, bunazosin, trimazosin, doxazosin, naftopidil, indoramin, WHIP 164, and XEN010, and the like; (xi) alpha 2 agonists such as lofexidine, tiamenidine, moxonidine, rilmenidine and guanobenz, and the like; and (xii) aldosterone inhibitors, and the like; and (d) anti-obesity agents, such as (i) 5HT (serotonin) transporter inhibitors, such as paroxetine, fluoxetine, fenfluramine, fluvoxamine, sertraline, and imipramine; (ii) NE (norepinephrine) transporter inhibitors, such as GW 320659, despiramine, talsupram, and nomifensine; (iii) CB-1 (cannabinoind-1 receptor) antagonist/inverse agonists, such as rimonabant (Sanofi Synthelabo), SR-147778 (Sanofi Synthelabo), BAY 65-2520 (Bayer), and SLV 319 (Solvay), and those disclosed in U.S. Pat. Nos. 5,532,237, 4,973,587, 5,013, 837, 5,081,122, 5,112,820, 5,292,736, 5,624,941 and U.S. Pat. No. 6,028,084; and WO96/33159, WO98/33765, WO98/43636, WO98/43635, WO 01/09120, WO 01.96330, WO98/31227, WO98/41519, WO98/37061, WO00/10967, WO00/10968, WO97/29079, WO99/02499, WO 01/58869, WO 02/076949, WO 01/64632, WO 01/64633, WO 01/64634, WO 03/006007, and WO 03/007887; and EPO Application No. EP-658546; (iv) ghrelin antagonists, such as those disclosed in WO 01/87335, and WO 02/08250; (v) H3 (histamine H3) antagonist/inverse agonists, such as thioperamide, 3-(1H-imidazol-4-yl)propyl N-(4-pentenyl)carbamate, clobenpropit, iodophenpropit, imoproxifan, GT2394 (Gliatech), and A331440, and those disclosed in WO 02/15905; and O-[3-(1H-imidazol-4-yl)propanol]carbamates (Kiec-Kononowicz, K. et al., Pharmazie, 55:349-55 (2000)), piperidine-containing histamine H3-receptor antagonists (Lazewska, D. et al., Pharmazie, 56:927-32 (2001), benzophenone derivatives and related compounds (Sasse, A. et al., Arch. Pharm. (Weinheim) 334:45-52 (2001)), substituted N-phenylcarbamates (Reidemeister, S. et al., Pharmazie, 55:83-6 (2000)), and proxifan derivatives (Sasse, A. et al., J. Med. Chem. 43:3335-43 (2000)); (vi) melanin-concentrating hormone 1 receptor (MCH1R) antagonists, such as T-226296 (Takeda), SNP-7941 (Synaptic), and those disclosed in WO 01/82925, WO 01/87834, WO 02/051809, WO 02/06245, WO 02/076929, WO 02/076947, WO 02/04433, WO 02/51809, WO 02/083134, WO 02/094799, WO 03/004027, and Japanese Patent Application No. JP 13226269; (vii) MCH2R (melanin concentrating hormone 2R) agonist/antagonists; (viii) NPY1 (neuropeptide Y Y1) antagonists, such as BIBP3226, 2-[1-(5-chloro-3-isopropyloxycarbonylaminophenyl)ethylamino]-6-[2-(5-ethyl-4-methyl-1,3-thiazol-2-yl)ethyl]-4-morpholinopyridine, BIBO 3304, LY-357897, CP-671906, and GI-264879A; and those disclosed in U.S. Pat. No. 6,001,836; and WO 96/14307, WO 01/23387, WO 99/51600, WO 01/85690, WO 01/85098, WO 01/85173, and WO 01/89528; (ix) NPY5 (neuropeptide Y Y5) antagonists, such as L-152,804, GW-569180A, GW-594884A, GW-587081X, GW-548118X; FR 235,208; FR226928, FR 240662, FR252384; 1229U91, GI-264879A, CGP71683A, LY-377897, LY366377, PD-160170, SR-120562A, SR-120819A, JCF-104, and H409/22; and those compounds disclosed in U.S. Pat. Nos. 6,140,354, 6,191,160, 6,258,837, 6,313,298, 6,337,332, 6,329,395, and 6,340,683; U.S. Pat. Nos. 6,326,375; 6,329,395; 6,337,332; 6,335,345; European Patent Nos. EP-01010691, and EP-01044970; and PCT International Patent Publication Nos. WO 97/19682, WO 97/20820, WO 97/20821, WO 97/20822, WO 97/20823, WO 98/27063, WO 00/107409, WO 00/185714, WO 00/185730, WO 00/64880, WO 00/68197, WO 00/69849, WO 01/09120, WO 01/14376, WO 01/85714, WO 01/85730, WO 01/07409, WO 01/02379, WO 01/02379, WO 01/23388, WO 01/23389, WO 01/44201, WO 01/62737, WO 01/62738, WO 01/09120, WO 02/20488, WO 02/22592, WO 02/48152, WO 02/49648 and WO 02/094789; and Norman et al., J. Med. Chem. 43:4288-4312 (2000); (x) leptin, such as recombinant human leptin (PEG-OB, Hoffman La Roche) and recombinant methionyl human leptin (Amgen); (xi) leptin derivatives, such as those disclosed in U.S. Pat. Nos. 5,552,524; 5,552, 523; 5,552,522; 5,521,283; and PCT International Publication Nos. WO 96/23513; WO 96/23514; WO 96/23515; WO 96/23516; WO 96/23517; WO 96/23518; WO 96/23519; and WO 96/23520; (xii) opioid antagonists, such as nalmefene (Revex®), 3-methoxynaltrexone, naloxone, and naltrexone; and those disclosed in WO 00/21509; (xiii) orexin antagonists, such as SB-334867-A; and those disclosed in WO 01/96302, WO 01/68609, WO 02/51232, WO 02/51838, and WO 03/023561; (xiv) BRS3 (bombesin receptor subtype 3) agonists; (xv) CCK-A (cholecystokinin-A) agonists, such as AR-R 15849, GI 181771, JMV-180, A-71378, A-71623 and SR146131, and those disclosed in U.S. Pat. No. 5,739,106; (xvi) CNTF (ciliary neurotrophic factors), such as GI-181771 (Glaxo-SmithKline); SR146131 (Sanofi Synthelabo); butabindide; and PD170,292, PD 149164 (Pfizer); (xvii) CNTF derivatives, such as axokine (Regeneron); and WO 94/09134, WO 98/22128, and WO 99/43813; (xviii) GHS (growth hormone secretagogue receptor) agonists, such as NN703, hexarelin, MK-0677, SM-130686, CP-424,391, L-692,429 and L-163,255, and those disclosed in U.S. Pat. No. 6,358, 951, U.S. Patent Application Nos. 2002/049196 and 2002/022637; and WO 01/56592, and WO02/32888; (xix) 5HT2c (serotonin receptor 2c) agonists, such as BVT933, DPCA37215, IK264; PNU 22394; WAY161503, R-1065, and YM 348; and those disclosed in U.S. Pat. No. 3,914,250; and WO 02/36596, WO 02/48124, WO 02/10169, WO 01/66548, WO 02/44152; WO 02/51844, WO 02/40456, and WO 02/40457; (xx) Mc3r (melanocortin 3 receptor) agonists; (xxi) Mc4r (melanocortin 4 receptor) agonists, such as CHIR86036 (Chiron); ME-10142, and ME-10145 (Melacure), and those disclosed in WO 99/64002, WO 00/74679, WO 01/991752, WO 01/74844, WO 01/70708, WO 01/70337, WO 01/91752, WO 02/059095, WO 02/059107, WO 02/059108, WO 02/059117, WO 02/12166, WO 02/11715, WO 02/12178, WO 02/15909, WO 02/068387, WO 02/068388, WO 02/067869, WO 03/007949, and WO 03/009847; (xxii) monoamine reuptake inhibitors, such as sibutratmine (Meridia®/Reductil®) and a salt thereof, and those compounds disclosed in U.S. Pat. Nos. 4,746,680, 4,806,570, and 5,436,272, and U.S. Patent Publication No. 2002/0006964, and WO 01/27068, and WO 01/62341; (xxiii) serotonin reuptake inhibitors, such as dexfenfluramine, fluoxetine, and those in U.S. Pat. No. 6,365,633, and WO 01/27060, and WO 01/162341; (xxiv) GLP-1 (glucagon-like peptide 1) agonists; (xxv) Topiramate (Topimax®); (xxvi) phytopharm compound 57 (CP 644,673); (xxvii) ACC2 (acetyl-CoA carboxylase-2) inhibitors; (xxviii) β3 (beta adrenergic receptor 3) agonists, such as AD9677/TAK677 (Dainippon/Takeda), CL-316,243, SB 418790, BRL-37344, L-796568, BMS-196085, BRL-35135A, CGP12177A, BTA-243, GW 427353, Trecadrine, Zeneca D7114, and SR 59119A, and those disclosed in U.S. Pat. No. 5,705,515, U.S. Pat. No. 5,451,677; and WO 01/74782, and WO 02/32897; (xxix) DGAT1 (diacylglycerol acyltransferase 1) inhibitors; (xxx) DGAT2 (diacylglycerol acyltransferase 2) inhibitors; (xxxi) FAS (fatty acid synthase) inhibitors, such as Cerulenin and C75; (xxxii) PDE (phosphodiesterase) inhibitors, such as theophylline, pentoxifylline, zaprinast, sildenafil, amrinone, milrinone, cilostamide, rolipram, and cilomilast; (xxxii) thyroid hormone β agonists, such as KB-2611 (KaroBioBMS), and those disclosed in WO 02/15845; and Japanese Patent Application No. JP 2000256190; (xxxiii) UCP-1 (uncoupling protein 1), 2, or 3 activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; and those disclosed in WO 99/00123; (xxxiv) acyl-estrogens, such as oleoyl-estrone, disclosed in del Mar-Grasa, M. et al., Obesity Research, 9:202-9 (2001); (xxxv) glucocorticoid antagonists; (xxxvi) 11β HSD-1 (11-beta hydroxy steroid dehydrogenase type 1) inhibitors, such as BVT 3498, BVT 2733, and those compounds disclosed in WO 01/90091, WO 01/90090, WO 01/90092; (xxxvii) SCD-1 (stearoyl-CoA desaturase-1) inhibitors; (xxxviii) dipeptidyl peptidase IV (DP-IV) inhibitors, such as isoleucine thiazolidide, valine pyrrolidine, NVP-DPP728, LAF237, P93/01, TSL 225, TMC-2A/2B/2C, FE 999011, P9310/K364, VIP 0177, SDZ 274-444; and the compounds disclosed in WO 03/004498, WO 03/004496, EP 1 258 476, WO 02/083128, WO 02/062764, WO 03/000250, WO 03/002530, WO 03/002531, WO 03/002553, WO 03/002593, WO 03/000180, and WO 03/000181; (xxxviii) lipase inhibitors, such as tetrahydrolipstatin (orlistat/Xenical®), Triton WR1339, RHC80267, lipstatin, teasaponin, and diethylumbelliferyl phosphate, FL-386, WAY-121898, Bay-N-3176, valilactone, esteracin, ebelactone A, ebelactone B, and RHC 80267, and those disclosed in WO 01/77094, and U.S. Pat. Nos. 4,598,089. 4,452,813, 5,512,565, 5,391,571, 5,602,151, 4,405,644, 4,189,438, and 4,242,453; (xxxix) fatty acid transporter inhibitors; (xxxx) dicarboxylate transporter inhibitors; (xxxxi) glucose transporter inhibitors; (xxxxii) phosphate transporter inhibitors; (xxxxiii) melanocortin agonists, such as Melanotan II or those described in WO 99/64002 and WO 00/746799; (xxxxiv) melanin concentrating hormone antagonists; (xxxxv) galanin antagonists; (xxxxvi) CCK agonists; (xxxxvii) corticotropin-releasing hormone agonists; and (xxxxviii) phosphodiesterase-3B (PDE3B) inhibitors; and the like.

The above combinations include combinations of a composition of the present invention not only with one other active compound, but also with two or more other active compounds. Non-limiting examples include combinations of the compositions of the present invention with one, two or more active compounds selected from lipid-lowering agents, and anti-hypertensive agents. Combinations of the compositions of the present invention with one, two or more active compounds selected from lipid lowering agents, and anti-diabetic agents are useful to treat, control or prevent metabolic syndrome. In particular, compositions comprising an anti-obesity agent, an anti-hypertensive agent, in addition to an anti-diabetic agent and/or a lipid lowering agent will be useful to synergistically treat, control or prevent metabolic syndrome.

EXAMPLES

The following Examples and Reference Examples are provided to illustrate the present invention more concretely, but they should not be construed as limiting the invention in any way.

The mass spectrum was determined by electron spray ionization (ESI) method using QuattroII (Product of Micromass Ltd.).

Unless otherwise noted, melting point was disclosed in this specification without correction.

Example 1

Preparation of 5,6-dichloro-2-[1-methylsulfonyl-spiro[indoline-3,4'-piperidin]-1'-yl]benzimidazole (1) Preparation of 2,5,6,-trichloro-N-tetrahydropyranyl-benzimidazole To a solution of 2,5,6-trichlorobenzimidazole (2.07 g, 9.33 mmol) in tetrahydrofuran (20 mL) were added 3,4-dihydro-2H-pyran (2.55 mL, 28.0 mmol) and camphor sulfonic acid (216 mg, 0.93 mmol). The mixture was stirred at room temperature for 3 hours, and the reaction mixture was neutralized by addition of 0.1M aqueous sodium hydroxide, then extracted with ethyl acetate. The organic layer was washed with saturated brine, dried over anhydrous sodium sulfate, and concentrated in vacuo. The residue was purified by silica gel column chromatography (C-300, hexane:ethyl acetate=4:1) to give the title compound (487 mg, 9%).

(2) Preparation of 5,6-dichloro-2-[1-methylsulfonyl-spiro[indoline-3,4'-piperidin]-1'-yl]benzimidazole To a solution of 2,5,6-trichloro-N-tetrahydropyranyl-benzimidazole (213 mg, 0.70 mmol) and 1-methylsulfonyl-spiro

[indoline-3,4'-piperidine]hydrochloride (168 mg, 0.56 mmol) in dioxane (10 mL) was added cesium carbonate (562 mg, 0.47 mmol). The mixture was stirred at 150° C. for 14 hours in a sealed tube and then cooled. After addition of water, the reaction mixture was extracted with ethyl acetate. The organic layer was dried over sodium sulfate, and concentrated in vacuo. The resulting residue was dissolved in methanol (10 mL), and camphor sulfonic acid (100 mg, 0.70 mmol) was added thereto, then stirred at room temperature for 12 hours. The reaction mixture was concentrated in vacuo, and the residue was neutralized with 0.1M aqueous sodium hydroxide, then extracted with chloroform. The organic layer was washed with brine, dried over anhydrous sodium sulfate, and concentrated in vacuo. The precipitate formed upon addition of ethyl acetate to the residue was collected by filtration and dried to give the title compound (86 mg, 34%).

$^1$HNMR (300 MHz, DMSO-$d_6$, δ ppm): 1.73-1.79 (2H, m), 1.85-1.96 (2H, m), 3.05 (3H, s), 3.18-3.30 (2H, m), 3.96 (2H, s), 4.08-4.18 (2H, m), 7.00-7.05 (1H, m), 7.20-7.32 (5H, m); mass spectrum (ESI): 452 (M+H)

The following compound was prepared according to the procedure described in Example 1.

Example 2

2-[1-Methylsulfonylspiro[indoline-3,4'-piperidin]-1'-yl]-5-chlorobenzimidazole $^1$HNMR (300 MHz, DMSO-$d_6$, δ ppm): 1.72-1.80 (2H, m), 1.87-1.98 (2H, m), 3.06 (3H, s), 3.12-3.28 (2H, m), 3.96 (2H, s), 4.08-4.17 (2H, m), 6.85-7.30 (7H, m), 11.51 (1H, s); mass spectrum (ESI): 418 (M+H)

Example 3

8-[3,4-dihydro-3-oxospiro[isoquinoline-1(2H),4'-piperidin]-1'-yl]-2-phenylpurine $^1$HNMR (300 MHz, DMSO-$d_6$, δ ppm): 1.87 (2H, d, J=13.8 Hz), 2.15 (2H, m), 3.62 (4H, m), 4.20 (2H, brd, J=12.6 Hz), 7.24 (3H, m), 7.43 (4H, m), 8.31 (1H, t, J=3.9 Hz), 8.36 (2H, dd, J=6.9 Hz), 8.50 (1H, brs); mass spectrum (ESI): 411 (M+H)

Example 4

Preparation of trans-5-methoxycarbonyl-2-[3'-oxospiro[cyclohexane-1,1'(3'H)-isobenzofuran]-4-yl]benzimidazole (1) Preparation of trans-N-[2-amino-5-methoxycarbonyl-phenyl]-3'-oxospiro[cyclohexane-1,1'(3'H)-isobenzofuran]-4-carboxamide To a solution of trans-3'-oxospiro[cyclohexane-1,1'(3'H)-isobenzofuran]-4-carboxylic acid (20 mg, 0.081 mmol) and methyl 3,4-diaminobenzoate (20 mg, 0.12 mmol) in pyridine (1 mL) was added 1-(3-dimethylaminopropyl)-3-ethylcarbodiimide hydrochloride (25 mg, 0.13 mmol). The mixture was stirred at room temperature for one hour under a nitrogen atmosphere, and then concentrated. After addition of saturated aqueous sodium bicarbonate to the residue, the mixture was extracted with ethyl acetate. The organic layer was dried over anhydrous magnesium sulfate, and concentrated in vacuo. The residue was washed with ethyl acetate-hexane, and dried to give the title compound (30.4 mg, 95%).

(2) Preparation of trans-5-methoxycarbonyl-2-[3'-oxospiro[cyclohexane-1,1'(3'H)-isobenzofuran]-4-yl]benzimidazole To a solution of trans-N-[2-amino-5-methoxycarbonyl-phenyl]-3'-oxospiro[cyclohexane-1,1'(3'H)-isobenzofuran]-4-carboxamide (27.7 mg, 0.070 mmol) in xylene (2 mL) was added a catalytic amount of p-toluenesulfonic acid monohydrate. The mixture was heated under ref lux for 3 hours, cooled to room temperature, and concentrated in vacuo. The residue was purified by preparative thin-layer chromatography (chloroform:methanol=20:1) to give the title compound (20 mg, 75%).

$^1$HNMR (300 MHz, CD$_3$OD, δ ppm): 1.78-2.55 (8H, m), 3.25-3.44 (1H, m), 3.93 (3H, s), 7.51-7.58 (4H, m), 7.85 (1H, dd, J=1.0 Hz, 7.6 Hz), 7.93 (1H, dd, J=1.6 Hz, 8.6 Hz), 8.27 (1H, s); mass spectrum (ESI): 377 (M+H)

The following compound was prepared according to the procedure described in Example 4.

Example 5

Trans-2-[3-oxospiro[6-azaisobenzofuran-1(3H),1'-cyclohexan]-4'-yl]-5-phenylbenzimidazole $^1$HNMR (400 MHz, CDCl$_3$, δ ppm): 1.80-2.02 (2H, m), 2.16-2.68 (6H, m), 3.30-3.44 (1H, m), 7.20-7.90 (9H, m), 8.85 (1H, d, J=4.8 Hz), 8.97 (1H, s); mass spectrum (ESI): 396 (M+H)

Example 6

Preparation of trans-8-[3'-oxospiro[cyclohexane-1,1'(3'H)-isobenzofuran]-4-yl]-2-phenylpurine (1) Preparation of trans-N-[4-amino-2-phenyl-5-pyrimidyl]-3'-oxospiro[cyclohexane-1,1'(3'H)-isobenzofuran]-4-carboxamide To a solution of trans-3'-oxospiro[cyclohexane-1,1'(3'H)-isobenzofuran]-4-carboxylic acid (190 mg, 0.77 mmol) and 2-phenyl-4,5-diaminopyrimidine (130 mg, 0.70 mmol) in pyridine (3.5 mL) was added 1-(3-dimethylaminopropyl)-3-ethylcarbodiimide hydrochloride (25 mg, 0.13 mmol) at 0° C. The mixture was stirred at room temperature for 10 hours under a nitrogen atmosphere and then concentrated. After addition of saturated aqueous sodium bicarbonate to the residue, the mixture was extracted with ethyl acetate. The organic layer was dried over anhydrous magnesium sulfate and concentrated. The residue was purified by silica gel column chromatography (chloroform:methanol=10:1) to give the title compound (212 mg, 73%).

(2) Preparation of trans-8-[3'-oxospiro[cyclohexane-1,1'(3'H)-isobenzofuran]-4-yl]-2-phenylpurine To a solution of trans-N-[4-amino-2-phenyl-5-pyrimidyl]-3'-oxospiro[cyclohexane-1,1'(3'H)-isobenzofuran]-4-carboxamide (100 mg, 0.24 mmol) in pyridine (3.5 mL) was added phosphorus oxychloride (0.027 mL, 0.28 mmol). The mixture was stirred at 50° C. for 12 hours under a nitrogen atmosphere. The reaction mixture was cooled to room temperature, and then concentrated in vacuo. The residue was diluted with ethyl acetate, and the mixture was washed successively with saturated aqueous sodium bicarbonate and saturated brine, dried over anhydrous magnesium sulfate, and concentrated in vacuo. The resulting residue was purified by preparative thin-layer chromatography (chloroform:methanol=10:1) to give the title compound (87 mg, 91%).

$^1$HNMR (300 MHz, CDCl$_3$, δ ppm): 1.70-1.90 (2H, m), 2.20-2.50 (6H, m), 3.25-3.40 (1H, m), 7.40-7.70 (6H, m), 7.89 (1H, d, J=7.8 Hz), 8.40-8.50 (2H, m), 9.21 (1H, s); mass spectrum (ESI): 397 (M+H)

The following compounds were prepared according to the procedure described in Example 6.

Example 7

Cis-8-[3'-oxospiro[cyclohexane-1,1'(3'H)-isobenzofuran]-4-yl]-2-phenylpurine $^1$HNMR (300 MHz, CDCl$_3$, δ ppm): 1.80-2.00 (2H, m), 2.05-2.45 (6H, m), 2.95-3.15 (1H, m), 7.36 (1H, d, J=7.8 Hz), 7.45-7.65 (4H, m), 7.65-7.80 (1H, m), 7.99 (1H, d, J=7.5 Hz), 8.42-8.55 (2H, m), 9.16 (1H, s); mass spectrum (ESI): 397 (M+H)

Example 8

Trans-2-(2-fluorophenyl)-8-[3'-oxospiro[cyclohexane-1,1'(3'H)-isobenzofuran]-4-yl]purine $^1$HNMR (300 MHz, CDCl$_3$, δ ppm): 1.60-1.90 (2H, m), 2.05-2.35 (6H, m), 3.00-3.10 (1H, m), 7.20-7.75 (6H, m), 7.88 (1H, d, J=7.5 Hz), 8.09 (1H, t, J=6.0 Hz), 9.28 (1H, s); mass spectrum (ESI): 415 (M+H)

Example 9

Trans-2-[2-(difluoromethoxy)phenyl]-8-[3'-oxospiro[cyclohexane-1,1'(3'H)-isobenzofuran]-4-yl]purine $^1$HNMR (300 MHz, CDCl$_3$, δ ppm): 1.40-1.90 (2H, m), 2.00-2.55 (6H, m), 2.85-3.00 (1H, m), 6.70 (1H, t, J=7.5 Hz), 7.20-7.75 (5H, m), 7.88 (1H, d, J=7.5 Hz), 7.97 (1H, d, J=7.5 Hz), 8.55-8.70 (1H, m), 9.25 (1H, s); mass spectrum (ESI): 463 (M+H)

Example 10

Trans-2-(2,6-difluorophenyl)-8-[3'-oxospiro[cyclohexane-1,1'(3'H)-isobenzofuran]-4-yl]purine $^1$HNMR (300 MHz, DMSO-d$_6$, δ ppm): 1.75-1.88 (2H, m), 2.21-3.03 (6H, m), 3.41-3.52 (1H, br), 7.25 (2H, t, J=7.8 Hz), 7.50-7.80 (5H, m), 7.82 (1H, d, J=7.8 Hz), 9.18 (1H, s); mass spectrum (ESI): 433 (M+H)

Example 11

Trans-8-[3-oxospiro[6-azaisobenzofuran-1(3H),1'-cyclohexan]-4'-yl]-2-phenylpurine $^1$HNMR (300 MHz, CDCl$_3$, δ ppm): 1.50-1.90 (2H, m), 2.15-2.40 (4H, m), 3.10-3.24 (1H, m), 7.47-7.65 (3H, m), 7.77 (1H, d, J=4.8 Hz), 8.35-8.50 (2H, m), 8.85 (1H, d, J=5.1 Hz), 8.95 (1H, s), 9.23 (1H, s); mass spectrum (ESI): 398 (M+H)

Example 12

Trans-2-(3-fluorophenyl)-8-[3-oxospiro[6-azaisobenzofuran-1(3H),1'-cyclohexan]-4'-yl]purine $^1$HNMR (300 MHz, DMSO-d$_6$, δ ppm): 1.88-2.56 (8H, m), 3.38-3.50 (1H, m), 7.28-7.40 (1H, m), 7.50-7.65 (1H, m), 7.87 (1H, d, J=4.9 Hz), 8.16 (1H, dd, J=1.1 Hz, 10.8 Hz), 8.29 (1H, d, J=7.8 Hz), 8.87 (1H, d, J=4.9 Hz), 9.15 (1H, s), 9.19 (1H, s); mass spectrum (ESI): 416 (M+H)

Example 13

Trans-2-(4-fluorophenyl)-8-[3-oxospiro[6-azaisobenzofuran-1(3H),1'-cyclohexan]-4'-yl]purine (1) Preparation of trans-N-[4-amino-2-(4-fluorophenyl)-5-pyrimidinyl]-3-oxospiro[6-azaisobenzofuran-1(3H),1'-cyclohexane]-4'-carboxamide To a solution of trans-3-oxospiro[6-azaisobenzofuran-1(3H),1'-cyclohexane]-4'-carboxylic acid (4.96 g, 20.0 mmol) and 2-(4-fluorophenyl)-4,5-diaminopyrimidine (3.7 g, 18.1 mmol) in pyridine (60 mL) was added 1-(3-dimethylaminopropyl)-3-ethylcarbodiimide hydrochloride (4.5 g, 23.5 mmol) at 0° C. The mixture was stirred at room temperature for 4 hours under a nitrogen atmosphere, and water (500 mL) and ethyl acetate (120 mL) were added thereto. The resulting precipitate was collected by filtration and dried to give the title compound as a colorless solid (3.97 g, 51%). The filtrate was extracted with ethyl acetate, and the extract was dried over anhydrous magnesium sulfate, then concentrated. The residue was suspended in ethyl acetate, stirred for a while, filtered off, and dried to further give the title compound (3.13 g, 39%).

$^1$HNMR (400 MHz, DMSO-d$_6$, δ ppm): 1.85-1.95 (2H, m), 2.00-2.30 (6H, m), 2.75-2.85 (1H, m), 6.82 (2H, brs), 7.25 (2H, t, J=7.2 Hz), 7.84 (1H, d, J=5.2 Hz), 8.25-8.35 (2H, m), 8.40 (1H, s), 8.86 (1H, d, J=5.2 Hz), 9.11 (1H, s), 9.23 (1H, s); mass spectrum (ESI): 434 (M+H)

(2) Preparation of trans-2-(4-fluorophenyl)-8-[3-oxospiro[6-azaisobenzofuran-1(3H),1'-cyclohexan]-4'-yl]purine To a solution of trans-N-[4-amino-2-(4-fluorophenyl)-5-pyrimidinyl]-3-oxospiro[6-azaisobenzofuran-1(3H),1'-cyclohexane]-4'-carboxamide (6.89 g, 15.9 mmol) in pyridine (100 mL) was added phosphorus oxychloride (2.3 mL, 24.6 mmol) at 0° C. After stirring at 50° C. for 16 hours under a nitrogen atmosphere, the reaction mixture was cooled down to room temperature and concentrated in vacuo. Ice-water was added to the residue, and the mixture was stirred for a while, then extracted with chloroform. The organic layer was dried over anhydrous magnesium sulfate, and concentrated in vacuo. The residue was purified by silica gel column chromatography (C-300, chloroform:tetrahydrofuran=4:1) to give the title compound (hereinafter referred to as Compound No. 13) as a colorless solid (3.0 g, 45%).

$^1$HNMR (400 MHz, CDCl$_3$, δ ppm): 1.44-2.58 (8H, m), 3.30-3.50 (1H, m), 7.19 (2H, t, J=8.8 Hz), 7.80 (1H, d, J=4.8 Hz), 8.46 (2H, dd, J=5.6 Hz, 8.8 Hz), 8.88 (1H, d, J=4.8 Hz), 8.96 (1H, s), 9.18 (1H, s); mass spectrum (ESI): 416 (M+H)

(3) Preparation of a Crystal (Form-A) of Compound No. 13

Tetrahydrofuran (1.5 L) was added to the compound (5.0 g) obtained in the above procedure (2). The mixture was dissolved by heating under reflux, and concentrated until the volume of the solvent was reduced to about 30 mL. The solution was cooled to room temperature, and the precipitated crystal formed upon stirring was collected by filtration to give a colorless crystal (Form-A, 4.1 g) of Compound No. 13.

M.p. 285° C.-288° C. (Yanagimoto Seisakusho, MP-S3).

| Powder X-ray diffraction | |
|---|---|
| 2θ | Intensity(cps) |
| 8.0 | 242 |
| 11.1 | 342 |
| 11.5 | 273 |
| 12.6 | 397 |
| 14.9 | 1497 |
| 16.0 | 808 |
| 16.2 | 728 |
| 17.7 | 1435 |
| 18.2 | 430 |
| 18.5 | 208 |
| 19.9 | 482 |
| 22.3 | 1103 |
| 22.6 | 1187 |
| 22.9 | 802 |
| 23.6 | 365 |
| 25.2 | 837 |
| 25.7 | 223 |
| 27.5 | 1585 |
| 27.9 | 178 |
| 28.2 | 202 |
| 28.7 | 362 |
| 29.6 | 165 |
| 30.2 | 538 |
| 33.8 | 163 |
| 34.1 | 185 |
| 35.5 | 153 |
| 36.6 | 135 |
| 41.5 | 147 |
| 41.6 | 153 |
| 45.3 | 178 |

The above powder X-ray diffraction data were measured using an automated X-ray apparatus RINT-Ultima+system (2 kW) (Rigaku International Corporation). The analysis was carried out as follows:

X-ray source: Cu

Tube voltage/tube current: 40 kV/30 mA

Monochromator: automated monochromator

Goniometer: wide angle goniometer

Scan step: 0.02 deg.

Scan velocity: 2.00 deg./min.

Divergence slit: 1 deg.

Scattering slit: 1 deg.

Receiving slit: 0.15 mm

Determination temperature: 5° C. to 40° C.

(4) Preparation of a Crystal (Form-B) of Compound No. 13

The crystal (Form-A, 4.6 g) obtained in the above procedure (3) was added to tetrahydrofuran (1.5 L), and the mixture was dissolved by heating under reflux. The solution was then cooled to 0° C., and a solution of maleic acid (1.33 g) in ethanol (10 ml) was added thereto. After the solvent was concentrated in vacuo, the residue was washed with ethyl acetate to give a maleate (6.0 g) of Compound No. 13.

The maleate (6.0 g) was suspended in water (300 ml), and the suspension was vigorously stirred at room temperature for 9 hours. The resulting precipitate was collected by filtration to give a colorless crystal (Form-B, 4.4 g) of Compound No. 13. M.p. 246° C.-252° C. (Yanagimoto Seisakusho, MP-S3).

| Powder X-ray diffraction | |
|---|---|
| 2θ | Intensity(cps) |
| 9.5 | 447 |
| 10.8 | 1197 |
| 13.8 | 243 |
| 14.1 | 438 |
| 14.4 | 413 |
| 15.0 | 1408 |
| 16.0 | 457 |
| 16.1 | 528 |
| 16.9 | 795 |
| 17.2 | 1550 |
| 17.7 | 285 |
| 19.4 | 332 |
| 19.7 | 403 |
| 20.2 | 755 |
| 22.4 | 367 |
| 22.6 | 473 |
| 23.1 | 613 |
| 23.2 | 520 |
| 24.9 | 245 |
| 26.1 | 2600 |
| 26.5 | 695 |
| 27.1 | 527 |
| 27.8 | 657 |
| 28.3 | 488 |
| 28.8 | 457 |
| 29.8 | 438 |
| 30.3 | 350 |
| 31.7 | 250 |
| 32.0 | 333 |
| 48.8 | 277 |

The above X-ray diffraction data were measured under the same conditions as in Example 13(3) except that the tube current was changed to 40 mA.

(5) Preparation of a Crystal (Form-C) of Compound No. 13

The crystal (Form-A, 680 mg) of Compound No. 13 obtained in the above procedure of (3) was suspended in water (35 mL). The suspension was stirred while heated under reflux for 15 hours, and the resulting precipitate was collected by filtration to give a colorless crystal (Form-C, 650 mg) of Compound No. 13.

M.p. 267° C.-270° C. (Mettler hot stage FP82).

| Powder X-ray diffraction | |
|---|---|
| 2θ | Intensity(cps) |
| 9.7 | 652 |
| 11.6 | 328 |
| 12.6 | 375 |
| 13.3 | 907 |
| 14.2 | 638 |
| 15.5 | 692 |
| 15.9 | 787 |
| 18.3 | 3808 |
| 18.7 | 1475 |
| 18.9 | 798 |
| 19.5 | 337 |
| 19.8 | 927 |
| 20.2 | 1453 |
| 21.2 | 705 |
| 23.9 | 733 |
| 24.7 | 4958 |
| 25.3 | 400 |
| 25.6 | 1140 |

-continued

Powder X-ray diffraction

| 2θ | Intensity(cps) |
|---|---|
| 25.9 | 538 |
| 26.6 | 390 |
| 27.1 | 668 |
| 27.3 | 375 |
| 28.3 | 2590 |
| 28.7 | 2395 |
| 29.9 | 805 |
| 31.4 | 927 |
| 32.2 | 363 |
| 34.0 | 393 |
| 41.1 | 378 |
| 43.7 | 330 |

The above X-ray diffraction data were measured under the same conditions as in Example 13(3).

(6) Preparation of a Crystal (Form-C) of Compound No. 13

(Alternative Method of the Procedure (5))

(6-1) 2-Propanol (20 mL) and 1N aqueous potassium hydroxide (2.6 mL) were successively added to Compound No. 13 (1.0 g) at 0° C., followed by stirring at the same temperature for 30 minutes. After dropwise addition of 0.15N hydrochloric acid (20 ml) to the reaction solution, the resulting precipitate was collected by filtration, and then dried to give a colorless solid (740 mg).

(6-2) The solid (380 mg) obtained above was suspended in 1N hydrochloric acid (10 mL), and the suspension was stirred at room temperature for 12 hours. The resulting precipitate was collected by filtration to give a colorless crystal (Form-C, 290 mg) of Compound No. 13.

The following compounds were prepared according to the procedure described in Example 6.

Example 14

Trans-2-(2-fluorophenyl)-8-[3-oxospiro[4-azaisobenzofuran-1(3H),1'-cyclohexane]-4'-yl]purine $^1$HNMR (300 MHz, CDCl$_3$, δ ppm): 1.60-1.90 (2H, m), 2.10-2.50 (6H, m), 2.97-3.10 (1H, m), 7.20-7.45 (6H, m), 7.45-7.63 (2H, m), 7.93 (1H, d, J=7.8 Hz), 8.12 (1H, t, J=7.8 Hz), 8.92 (1H, d, J=4.5 Hz), 9.28 (1H, s); mass spectrum (ESI): 416 (M+H)

Example 15

Trans-2-(2,4-difluorophenyl)-8-[3-oxospiro[4-azaisobenzofuran-1(3H),1'-cyclohexan]-4'-yl]purine $^1$HNMR (300 MHz, CDCl$_3$, δ ppm): 1.58-2.60 (8H, m), 3.10-3.80 (1H, m), 6.84-7.14 (2H, m), 7.78 (1H, d, J=4.8 Hz), 8.17 (1H, dd, J=8.4 Hz, J=14.8 Hz), 8.87 (1H, d, J=4.8 Hz), 8.94 (1H, s), 9.20 (1H, s); mass spectrum (ESI): 434 (M+H)

Example 16

Trans-2-(4-fluorophenyl)-8-[3-oxospiro[5-azaisobenzofuran-1(3H),1'-cyclohexan]-4'-yl]purine $^1$HNMR (300 MHz, DMSO-d$_6$, δ ppm): 1.80-2.60 (8H, m), 2.96-3.48 (1H, m), 7.22-7.42 (2H, m), 7.81 (1H, d, J=4.2 Hz), 8.38-8.54 (2H, m), 8.84 (1H, d, J=4.2 Hz), 9.07 (2H, s), 9.10 (2H, s); mass spectrum (ESI): 416 (M+H)

Example 17

Preparation of Trans-2-(2,5-difluorophenyl)-8-[3-oxospiro[6-azaisobenzofuran-1(3H),1'-cyclohexan]-4'-yl]purine (1) Working up in the same manner as Example 13 by use of trans-3-oxospiro[6-azaisobenzofuran-1(3H),1'-cyclohexane]-4'-carboxylic acid (24.0 g, 97.1 mmol) and 2-(2,5-difluorophenyl)-4,5-diaminopyrimidine (19.4 g, 87 mmol), there was obtained the title compound (hereinafter referred to as Compound No. 17) as a colorless solid (11.3 g, 30%).

$^1$HNMR (300 MHz, DMSO-d$_6$, δ ppm): 1.83-2.02 (8H, m), 3.38-3.49 (1H, br), 7.31-7.48 (2H, m), 7.78-7.92 (2H, m), 8.88 (1H, d, J=4.9 Hz), 9.19 (2H, s); mass spectrum (ESI): 434 (M+H)

(2) Preparation of a Crystal (Form-A) of Compound No. 17

Ethanol (390 mL) was added to Compound No. 17 (3.9 g) obtained in the above procedure (1). The mixture was dissolved by heating under reflux, and concentrated until the volume of the solvent was reduced to 120 mL. The solution was cooled down to room temperature, and stirred for 12 hours. The resulting precipitate was collected by filtration to give a colorless crystal (Form-A, 3.6 g) of Compound No. 17.

M.p. 265° C.-270° C. (Mettler hot stage FP82).

Powder X-ray diffraction

| 2θ | Intensity(cps) |
|---|---|
| 9.1 | 387 |
| 14.3 | 448 |
| 15.2 | 155 |
| 16.6 | 1155 |
| 17.2 | 263 |
| 18.0 | 1147 |
| 18.3 | 315 |
| 18.8 | 933 |
| 19.1 | 1002 |
| 19.3 | 1582 |
| 19.7 | 628 |
| 21.0 | 287 |
| 21.8 | 583 |
| 22.3 | 303 |
| 22.9 | 997 |
| 23.7 | 407 |
| 24.2 | 428 |
| 24.6 | 518 |
| 24.8 | 802 |
| 25.3 | 368 |
| 26.0 | 270 |
| 27.7 | 278 |
| 28.4 | 365 |
| 29.1 | 245 |
| 29.6 | 243 |
| 31.0 | 393 |
| 33.3 | 235 |
| 33.7 | 175 |
| 36.7 | 192 |
| 38.2 | 162 |

The above powder X-ray diffraction data were measured in the same manner as Example 13(3).

(3) Preparation of a Crystal (Form-B) of Compound No. 17

2-Propanol (10 mL) and 1N aqueous potassium hydroxide (1.2 mL) were successively added to Compound No. 17 (500 mg) at 0° C., followed by stirring for 30 minutes. After dropwise addition of 0.15N hydrochloric acid (10 mL), the mixture was further stirred for 30 minutes. The resulting precipitate was collected by filtration to give a colorless crystal (Form-B, 390 mg) of Compound No. 17.

M.p. 223° C.-227° C. (Mettler hot stage FP82).

| Powder X-ray diffraction | |
|---|---|
| 2θ | Intensity(cps) |
| 10.2 | 103 |
| 11.5 | 292 |
| 12.6 | 708 |
| 13.3 | 105 |
| 14.8 | 202 |
| 15.5 | 153 |
| 16.4 | 137 |
| 16.9 | 110 |
| 18.2 | 212 |
| 18.9 | 92 |
| 19.0 | 122 |
| 19.3 | 82 |
| 19.4 | 80 |
| 20.1 | 247 |
| 20.2 | 213 |
| 21.5 | 113 |
| 23.3 | 282 |
| 25.3 | 57 |
| 25.9 | 368 |
| 26.3 | 75 |
| 26.9 | 102 |
| 27.2 | 203 |
| 27.6 | 338 |
| 27.9 | 83 |
| 28.1 | 68 |
| 30.4 | 70 |
| 31.6 | 55 |
| 32.0 | 70 |
| 33.2 | 58 |

The above powder X-ray diffraction data were measured under the same conditions as Example 13(3).

The following compounds were prepared according to the procedure described in Example 6.

Example 18

Trans-2-(5-chloro-2-fluorophenyl)-8-[3-oxospiro[6-aza-isobenzofuran-1(3H),1'-cyclohexan]-4'-yl]purine $^1$HNMR (300 MHz, CDCl$_3$, δ ppm): 1.70-1.95 (2H, m), 2.20-2.60 (6H, m), 3.20-3.40 (1H, m), 7.10-7.30 (1H, m), 7.40-7.55 (1H, m), 7.78 (1H, d, J=5.1 Hz), 8.10-8.25 (1H, m), 8.87 (1H, d, J=5.1 Hz), 8.93 (1H, s), 9.27 (1H, s); mass spectrum (ESI): 450 (M+H)

Example 19

Trans-8-[5-fluoro-3-oxospiro[6-azaisobenzofuran-1 (3H),1'-cyclohexan]-4'-yl]-2-phenylpurine $^1$HNMR (300 MHz, DMSO-d$_6$, δ ppm): 1.90-2.06 (2H, m), 2.10-2.28 (4H, m), 2.29-2.45 (2H, m), 3.35-3.45 (1H, m), 7.42-7.56 (3H, m), 7.70 (1H, d, J=3.3 Hz), 8.44 (2H, dd, J=7.8 Hz, J=1.8 Hz), 8.82 (1H, s), 9.12 (1H, s); mass spectrum (ESI): 416 (M+H)

Example 20

Trans-8-[5-fluoro-3-oxospiro[6-azaisobenzofuran-1 (3H),1'-cyclohexan]-4'-yl]-2-(2-fluorophenyl)purine $^1$HNMR (400 MHz, DMSO-d$_6$, δ ppm): 1.90-2.70 (8H, m), 3.08-3.60 (1H, m), 7.24-7.42 (2H, m), 7.42-7.60 (1H, m), 7.69 (1H, s), 8.00-8.14 (1H, m), 8.80 (1H, s), 9.13 (1H, s); mass spectrum (ESI): 434 (M+H)

Example 21

Trans-2-(2,4-difluorophenyl)-8-[5-fluoro-3-oxospiro[6-azaisobenzofuran-1(3H),1'-cyclohexan]-4'-yl]purine $^1$HNMR (400 MHz, DMSO-d$_6$, δ ppm): 1.90-2.06 (2H, m), 2.06-2.60 (6H, m), 3.16-3.50 (1H, m), 7.14-7.30 (1H, m), 7.30-7.42 (1H, m), 7.69 (1H, s), 8.02-8.18 (1H, m), 8.79 (1H, s), 9.12 (1H, s); mass spectrum (ESI): 459 (M+H)

Example 22

Trans-2-chloro-8-[3'-oxospiro[cyclohexane-1,1' (3'H)-isobenzofuran]-4-yl]purine $^1$HNMR (300 MHz, DMSO-d$_6$, δ ppm): 1.73-1.82 (2H, m), 1.96-2.20 (4H, m), 2.23-2.35 (2H, m), 3.14-3.32 (1H, m), 7.56-7.65 (1H, m), 7.76-7.87 (3H, m), 8.82 (1H, s); mass spectrum (ESI): 355, 357 (M+H)

Example 23

Preparation of trans-2-(6-fluoropyridin-2-yl)-8-[3'-oxospiro[cyclohexane-1,1'(3'H)-isobenzofuran]-4-yl] purine (1) Preparation of trans-2-chloro-8-[3'-oxospiro[cyclohexane-1,1'(3'H)-isobenzofuran]-4-yl]-7-(2-trimethylsilylethoxymethyl)purine To a solution of trans-2-chloro-8-[3'-oxospiro[cyclohexane-1,1'(3'H)-isobenzofuran]-4-yl]purine (205 mg, 0.49 mmol) in dimethylformamide (5 mL) were added 2-(trimethylsilyl)ethoxymethyl chloride (0.12 mL, 0.59 mmol) and 60% sodium hydride (30 mg, 0.75 mmol). The mixture was stirred at 50° C. for 3 days, cooled to room temperature, and diluted with ethyl acetate and water. The organic layer was washed successively with water and saturated brine, dried over anhydrous sodium sulfate, and concentrated in vacuo. The residue was purified by silica gel column chromatography (C-300, hexane:ethyl acetate=3:2) to give the title compound (115 mg, 41%).

(2) Preparation of trans-2-(6-fluoropyridine-2-yl)-8-[3'-oxospiro[cyclohexane-1,1'(3'H)-isobenzofuran]-4-yl]purine To a solution of trans-2-chloro-8-[3'-oxospiro[cyclohexane-1,1'(3'H)-isobenzofuran]-4-yl]-7-(2-trimethylsilylethoxymethyl)purine (100 mg, 0.21 mmol) in toluene (2 mL) were added 6-fluoro-2-trimethyl-stannylpyridine (80 mg, 0.21 mmol) and [1,1'-bis(diphenylphosphino)ferrocene]

palladium(II) dichloride (17 mg, 0.02 mmol). The mixture was stirred under reflux at 120° C. for 15 hours under a nitrogen atmosphere. After the reaction solution was cooled to room temperature, it was diluted with ethyl acetate and water. The organic layer was washed successively with water and saturated brine, dried over anhydrous magnesium sulfate, and then concentrated in vacuo. The residue was purified by silica gel column chromatography (C-300, hexane:ethyl acetate=2:3) to give the title compound (67 mg, 59%).

$^1$HNMR (300 MHz, CDCl$_3$, δ ppm): 1.67-1.95 (2H, m), 2.15-2.36 (6H, m), 3.40-3.52 (1H, m), 7.03-7.11 (1H, m), 7.42-7.63 (3H, m), 7.87 (1H, d, J=7.5 Hz), 8.04 (1H, q, J=7.7 Hz), 8.56 (1H, d, J=7.7 Hz), 9.23 (1H, s), 12.4 (1H, brs); mass spectrum (ESI): 416 (M+H)

The following compounds were prepared according to the procedure described in Example 23.

Example 24

Trans-2-(2-furyl)-8-[3'-oxospiro[cyclohexane-1,1' (3'H)-isobenzofuran]-4-yl]purine $^1$HNMR (300 MHz, CDCl$_3$, δ ppm): 1.73-1.85 (2H, m), 2.25-2.47 (6H, m), 3.40-3.48 (1H, m), 6.64-6.66 (1H, m), 7.35 (1H, d, J=3.5 Hz), 7.43-7.55 (2H, m), 7.60-7.68 (2H, m), 7.89 (1H, d, J=7.6 Hz), 9.16 (1H, s), 11.17 (1H, s); mass spectrum (ESI): 387 (M+H)

Example 25

Trans-2-(indol-5-yl)-8-[3-oxospiro[6-azaisobenzofuran-1(3H),1'-cyclohexan]-4'-yl]purine $^1$HNMR (300 MHz, CDCl$_3$, δ ppm): 1.70-1.82 (2H, m), 2.05-2.35 (6H, m), 3.13-3.22 (1H, m), 6.66 (1H, d, J=2.5 Hz), 7.26-7.32 (1H, m), 7.55 (1H, d, J=8.5 Hz), 7.79 (1H, d, J=5.0 Hz), 8.24 (1H, d, J=8.5 Hz), 8.69 (1H, s), 8.85 (1H, d, J=5.0 Hz), 9.00 (1H, s), 9.17 (1H, s); mass spectrum (ESI): 437 (M+H)

Example 26

Preparation of trans-6-(4-fluorophenyl)-2-[3'-oxospiro[cyclohexane-1,1'(3'H)-isobenzofuran]-4-yl] imidazo[4,5-b]pyridine (1) Preparation of 2-amino-5-(4-fluorophenyl)-3-nitropyridine To a suspension of 2-amino-5-bromo-3-nitropyridine (2.2 g, 10.1 mmol) in dimethoxyethane (20 mL) were added 4-fluorophenylboronic acid (4.83 g, 13.1 mmol), tetrakis(triphenylphosphine)palladium (580 mg, 0.50 mmol) and 2N aqueous sodium carbonate solution (10 mL). The mixture was stirred at 80° C. for 9 hours under a nitrogen atmosphere. After the reaction mixture was cooled to room temperature, it was diluted with ethyl acetate to give a precipitate, which was collected by filtration, washed with ethyl acetate and then dried to give the title compound (1.76 g, 76%).

(2) Preparation of 2,3-diamino-5-(4-fluorophenyl)pyridine

2-Amino-5-(4-fluorophenyl)-3-nitropyridine (200 mg, 0.86 mmol) was suspended in a mixture of methanol (5 mL), ethyl acetate (5 mL), tetrahydrofuran (5 mL) and triethylamine (2 mL). After addition of 10% palladium carbon (100 mg), the mixture was stirred at room temperature for 1.5 hours under a hydrogen atmosphere. The reaction mixture was filtered, and the filtrate was concentrated in vacuo. The residue was purified by silica gel column chromatography (C-300, chloroform:methanol=50:1) to give the title compound (76 mg, 44%) as a white solid.

(3) Preparation of trans-N-[2-amino-5-(4-fluorophenyl)-3-pyridyl]-3'-oxospiro[cyclohexane-1,1'(3'H)-isobenzofuran]-4-carboxamide To a solution of 2,3-diamino-5-(4-fluorophenyl)pyridine (76 mg, 0.37 mmol) and trans-3'-oxospiro[cyclohexane-1,1' (3'H)-isobenzofuran]-4-carboxylic acid (92 mg, 0.37 mmol) in pyridine (1 mL) was added 1-(3-dimethylaminopropyl)-3-ethylcarbodiimide hydrochloride (86 mg, 0.45 mmol). The mixture was stirred at room temperature for 28 hours under a nitrogen atmosphere, and concentrated in vacuo. After addition of saturated aqueous sodium bicarbonate to the residue, the mixture was extracted with ethyl acetate. The organic layer was dried over anhydrous magnesium sulfate, and concentrated in vacuo. The residue was further washed with ethyl acetate and then dried to give the title compound (132 mg, 82%).

(4) Preparation of trans-6-(4-fluorophenyl)-2-[3'-oxospiro[cyclohexane-1,1'(3'H)-isobenzofuran]-4-yl] imidazo[4,5-b]pyridine To a solution of trans-N-[2-amino-5-(4-fluorophenyl)-3-pyridyl]-3'-oxospiro[cyclohexane-1,1'(3'H)-isobenzofuran]-4-carboxamide (130 mg, 0.30 mmol) in pyridine (4 mL) was added phosphorus oxychloride (0.15 mL, 1.5 mmol). The mixture was stirred at 50° C. for 16 hours. After the reaction mixture was cooled to room temperature, it was concentrated in vacuo. Aqueous ammonia was added to the residue, and the mixture was extracted with chloroform. The organic layer was dried over anhydrous magnesium sulfate, and concentrated in vacuo. The residue was purified by preparative thin-layer chromatography (chloroform:methanol=10:1) to give the title compound (32 mg, 32%).

$^1$HNMR (300 MHz, CDCl$_3$, δ ppm): 1.75-2.09 (2H, m), 2.23-2.75 (6H, m), 3.63 (1H, brs), 7.00-7.69 (7H, m), 7.88 (1H, d, J=7.4 Hz), 8.29 (1H, brs), 8.53 (1H, brs), 13.2-13.6 (1H, br); mass spectrum (ESI): 414 (M+H)

Example 27

Trans-5-(2-fluorophenyl)-2-[3-oxospiro[6-azaisobenzofuran-1(3H),1'-cyclohexan]-4'-yl]imidazo[4,5-b] pyridine (1) Working up in the same manner as Example 13 by use of trans-3'-oxospiro[cyclohexane-1,1'(3'H)-isobenzofuran]-4-carboxylic acid (13.1 g, 53 mmol) and 2,3-diamino-6-(2-fluorophenyl)pyridine (10.8 g, 53 mmol), there was obtained the title compound (hereinafter referred to as Compound No. 27) as a colorless solid (7.4 g, 34%).

$^1$HNMR (400 MHz, DMSO-d$_6$, δ ppm): 1.70-2.80 (8H, m), 2.80-3.68 (1H, m), 7.20-7.50 (2H, m), 7.61 (1H, d, J=7.2 Hz), 7.76-8.02 (2H, m), 7.85 (1H, d, J=4.8 Hz); 8.08 (1H, d, J=8.4 Hz), 8.86 (1H, d, J=4.8 Hz), 9.21 (1H, s); mass spectrum (ESI): 415 (M+H)

(2) Preparation of a Crystal (Form-A) of Compound No. 27

Ethyl acetate (2.0 L) was added to Compound No. 27 (6.1 g) obtained in the above procedure (1). The mixture was dissolved by heating to reflux, and concentrated until the volume of the solvent was reduced to 30 mL. The solution was cooled down to room temperature, and stirred vigorously. The resulting precipitate was collected by filtration to give a colorless crystal (Form-A, 5.7 g) of Compound No 27.

M.p. 242° C.-244° C. (BUCHI Melting Point B-545).

| Powder X-ray diffraction | |
|---|---|
| 2θ | Intensity(cps) |
| 8.0 | 1092 |
| 12.1 | 390 |
| 12.3 | 328 |
| 13.9 | 1273 |
| 15.2 | 312 |
| 15.4 | 320 |
| 16.2 | 937 |
| 17.4 | 537 |
| 18.3 | 177 |
| 19.4 | 303 |
| 20.2 | 288 |
| 20.3 | 355 |
| 20.9 | 760 |
| 21.3 | 580 |
| 21.8 | 690 |
| 22.5 | 167 |
| 23.4 | 193 |
| 24.4 | 552 |
| 25.3 | 258 |
| 25.9 | 165 |
| 26.0 | 167 |
| 26.5 | 458 |
| 26.6 | 527 |
| 27.0 | 472 |
| 27.9 | 222 |
| 28.1 | 217 |
| 28.9 | 168 |
| 29.1 | 190 |
| 29.3 | 215 |
| 29.6 | 213 |

The above powder X-ray diffraction data were measured under the same conditions as in Example 13(3).

(3) Preparation of a Crystal (Form-B) of Compound No. 27

The colorless crystal (Form-A, 20 mg) of Compound No. 27 obtained in the above procedure was suspended in water (2 ml). The suspension was stirred while heated under reflux for 12 hours, and the resulting precipitate was collected by filtration to give a colorless crystal (Form-B, 19 mg) of Compound No. 27.

M.p. 255° C.-256° C. (BUCHI Melting Point B-545).

| Powder X-ray diffraction | |
|---|---|
| 2θ | Intensity(cps) |
| 8.2 | 255 |
| 9.7 | 767 |
| 11.5 | 1162 |
| 12.8 | 358 |
| 13.2 | 323 |
| 14.4 | 250 |
| 14.9 | 330 |
| 15.3 | 797 |
| 16.5 | 490 |
| 18.1 | 2052 |
| 19.5 | 1180 |
| 20.0 | 1012 |
| 21.0 | 1552 |
| 23.1 | 475 |
| 23.4 | 652 |
| 24.4 | 2197 |
| 25.1 | 357 |
| 25.3 | 262 |
| 25.9 | 770 |
| 27.2 | 553 |
| 27.6 | 810 |
| 28.0 | 773 |
| 28.2 | 920 |
| 28.6 | 250 |
| 29.0 | 525 |
| 30.4 | 318 |
| 32.9 | 243 |
| 34.9 | 252 |
| 37.0 | 255 |
| 44.5 | 247 |

The above powder X-ray diffraction data were measured in the same manner as Example 13(3).

The following compounds were prepared according to the procedure described in Example 26.

Example 28

Trans-6-(2-fluorophenyl)-2-[3-oxospiro[6-azaisobenzofuran-1(3H),1'-cyclohexan]-4'-yl]imidazo[4,5-c]pyridine $^1$HNMR (400 MHz, DMSO-$d_6$, δ ppm): 1.70-2.70 (8H, m), 2.70-3.60 (1H, m), 7.20-7.48 (3H, m), 7.48-8.12 (2H, m), 7.85 (2H, d, J=4.8 Hz), 8.86 (1H, d, J=4.8 Hz), 9.00 (1H, s), 9.16 (1H, s); mass spectrum (ESI): 415 (M+H)

Example 29

Trans-2-[3'-oxospiro[cyclohexane-1,1'(3'H)-isobenzofuran]-4-yl]-5-phenylimidazo[4,5-b]pyrazine $^1$HNMR (400 MHz, CDCl$_3$, δ ppm): 1.70-2.70 (8H, m), 3.22-3.60 (1H, m), 7.20-8.20 (9H, m), 8.70-9.00 (1H, m); mass spectrum (ESI): 397 (M+H)

Example 30

Trans-2-[3'-oxospiro[cyclohexane-1,1'(3'H)-isobenzofuran]-4-yl]-6-phenylimidazo[4,5-b]pyridazine $^1$HNMR (400 MHz, DMSO-$d_6$, δ ppm): 1.70-1.90 (2H, m), 2.00-2.80 (6H, m), 3.20-3.40 (1H, m), 7.40-8.00 (7H, m), 8.10-8.40 (3H, m); mass spectrum (ESI): 397 (M+H)

Example 31

Trans-2-(2-fluorophenoxy)-8-[3'-oxospiro[cyclohexane-1,1'(3'H)-isobenzofuran]-4-yl]purine $^1$HNMR (300 MHz, DMSO-$d_6$, δ ppm): 1.73-1.87 (2H, m), 2.04-2.25 (4H, m), 2.29-2.41 (2H, m), 3.25-3.50 (1H, m), 7.24-7.45 (4H, m), 7.59 (1H, d, J=7.6 Hz), 7.64-7.80 (2H, m), 7.83 (1H, d, J=7.6 Hz), 8.85 (1H, s), 13.28 (1H, brs); mass spectrum (ESI) 431 (M+H)

Example 32

Trans-2-(2,6-difluorophenoxy)-8-[3'-oxospiro[cyclohexane-1,1'(3'H)-isobenzofuran]-4-yl]purine $^1$HNMR (300 MHz, DMSO-d$_6$, δ ppm): 1.72-1.84 (2H, m), 2.03-2.25 (4H, m), 2.31-2.41 (2H, m), 3.23-3.49 (1H, m), 7.26-7.44 (3H, m), 7.59 (1H, d, J=7.3 Hz), 7.65-7.80 (2H, m), 7.83 (1H, d, J=7.3 Hz), 8.87 (1H, s), 13.38 (1H, brs); mass spectrum (ESI): 449 (M+H)

Example 33

Trans-2-morpholino-8-[3'-oxospiro[cyclohexane-1,1'(3'H)-isobenzofuran]-4-yl]purine $^1$HNMR (300 MHz, DMSO-d$_6$, δ ppm): 1.72-1.86 (2H, m), 2.05-2.23 (4H, m), 2.24-2.38 (2H, m), 3.21-3.42 (1H, m), 3.65-3.74 (8H, m), 7.57-7.68 (2H, m), 7.73 (1H, d, J=7.7 Hz), 7.84 (1H, d, J=7.7 Hz), 8.67 (1H, s), 12.72 (1H, brs); mass spectrum (ESI): 406 (M+H)

Example 34

Trans-2-(N-methylanilino)-8-[3'-oxospiro[cyclohexane-1,1'(3'H)-isobenzofuran]-4-yl]purine $^1$HNMR (300 MHz, DMSO-d$_6$, δ ppm): 1.71-1.87 (2H, m), 2.02-2.22 (4H, m), 2.23-2.38 (2H, m), 3.20-3.41 (1H, m), 3.51 (3H, s), 7.14-7.23 (1H, m), 7.33-7.44 (4H, m), 7.60 (1H, t, J=7.4 Hz), 7.66 (1H, d, J=7.4 Hz), 7.74 (1H, t, J=7.4 Hz), 7.84 (1H, d, J=7.4 Hz), 8.66 (1H, s), 12.81 (1H, brs); mass spectrum (ESI): 426 (M+H)

Example 35

Trans-2-(4-fluorophenyl)-8-[7-hydroxy-3-oxospiro[6-azaisobenzofuran-1(3H),1'-cyclohexan]-4'-yl]purine $^1$HNMR (400 MHz, CD$_3$OD, δ ppm): 2.22-2.50 (2H, m), 2.50-2.80 (6H, m), 3.42-3.70 (1H, m), 6.62 (1H, d, J=6.8 Hz), 7.12-7.30 (2H, m), 7.51 (1H, d, J=6.8 Hz), 8.40-8.58 (2H, m), 8.98 (1H, s); mass spectrum (ESI): 432 (M+H)

Example 36

Trans-2-(4-fluorophenyl)-8-[3-oxospiro[6-azaisobenzofuran-1(3H),1'-cyclohexan]-4'-yl]purine 6-oxide $^1$HNMR (400 MHz, DMSO-d$_6$, δ ppm): 1.80-2.02 (2H, m), 2.02-2.28 (4H, m), 2.28-2.62 (2H, m), 3.02-3.60 (1H, m), 7.32 (2H, t, J=8.8 Hz), 7.82 (1H, d, J=6.8 Hz), 8.32 (2H, d, J=6.8 Hz), 8.42-8.54 (2H, m), 8.84 (1H, s), 9.08 (1H, s), 9.18 (1H, s); mass spectrum (ESI): 432 (M+H)

Example 37

Trans-2-(4-fluoro-2-hydroxyphenyl)-8-[3-oxospiro[6-azaisobenzofuran-1(3H),1'-cyclohexan]-4'-yl]purine $^1$HNMR (400 MHz, CD$_3$OD, δ ppm): 1.94-2.10 (2H, m), 2.22-2.58 (6H, m), 3.42-3.58 (1H, m), 6.62-6.78 (2H, m), 7.82-7.90 (1H, m), 8.50-8.62 (1H, m), 8.83 (1H, d, J=4.8 Hz), 9.04 (1H, s), 9.09 (1H, s); mass spectrum (ESI): 432 (M+H)

Example 38

Trans-2-(4-fluorophenyl)-6-hydroxy-8-[3-oxospiro[6-azaisobenzofuran-1(3H),1'-cyclohexan]-4'-yl]purine $^1$HNMR (400 MHz, CD$_3$OD, δ ppm): 1.94-2.10 (2H, m), 2.22-2.46 (6H, m), 3.22-3.40 (1H, m), 7.29 (2H, t, J=8.4 Hz), 7.85 (1H, d, J=4.4 Hz), 8.08-8.18 (2H, m), 8.83 (1H, d, J=4.4 Hz), 9.18 (1H, s); mass spectrum (ESI): 432 (M+H)

Example 39

Trans-2-(4-hydroxyphenyl)-8-[3-oxospiro[6-azaisobenzofuran-1(3H),1'-cyclohexan]-4'-yl]purine $^1$HNMR (400 MHz, CD$_3$OD, δ ppm): 1.94-2.10 (2H, m), 2.26-2.58 (6H, m), 3.52-3.62 (1H, m), 7.14 (2H, d, J=8.8 Hz), 7.88 (1H, d, J=5.2 Hz), 8.35 (2H, d, J=8.8 Hz), 8.85 (1H, d, J=5.2 Hz), 9.05 (1H, s), 9.13 (1H, s); mass spectrum (ESI): 414 (M+H)

Example 40

Trans-2-(4-fluoro-3-hydroxyphenyl)-8-[3-oxospiro[6-azaisobenzofuran-1(3H),1'-cyclohexan]-4'-yl]purine $^1$HNMR (400 MHz, DMSO-d$_6$, δ ppm): 1.80-2.70 (8H, m), 3.00-3.54 (1H, m), 7.23 (1H, d, J=7.6 Hz), 7.80-8.00 (2H, m), 8.07 (1H, d, J=7.6 Hz), 8.86 (1H, d, J=5.2 Hz), 9.06 (1H, s), 9.16 (1H, s); mass spectrum (ESI): 432 (M+H)

Example 41

Cis-2-(4-fluorophenyl)-8-[4'-hydroxy-3-oxospiro[6-azaiso-benzofuran-1(3H),1'-cyclohexan]-4'-yl]purine $^1$HNMR (400 MHz, CD$_3$OD, δ ppm): 1.94-3.42 (8H, m), 7.10-7.26 (2H, m), 7.80-7.98 (1H, m), 8.20-8.40 (2H, m), 8.80-8.96 (1H, m), 9.01 (1H, s), 9.09 (1H, s); mass spectrum (ESI): 432 (M+H)

Reference Example 1

Preparation of 2-phenyl-4,5'-diaminopyrimidine 2-phenyl-4-chloro-5-nitro-6-aminopyrimidine (367 mg, 1.46 mmol) which was produced according to the method described in the Journal of Chemical Society (C), 1408-1412 (1969) was suspended in a mixture of methanol (3 mL), ethyl acetate (2 mL) and triethylamine (0.21 mL). After addition of 10% palladium-carbon (40 mg), the mixture was stirred at room temperature for 2 hours under a hydrogen atmosphere and then filtered. The filtrate was concentrated in vacuo, and purified by silica gel column chromatography (C-300, chloroform:methanol=50:1) to give the title compound (175 mg, 64%) as a brown solid.

$^1$HNMR (300 MHz, CDCl$_3$, δ ppm): 7.35-7.47 (3H, m), 7.97 (1H, s), 8.20-8.27 (1H, m); mass spectrum (ESI): 187 (M+H)

Reference Example 2

Preparation of 2-phenyl-4,5-diaminopyrimidine

To a solution of 2-phenyl-5-nitropyrimidine (50.1 g, 250 mmol), which was produced according to the method described in the Journal of American Chemical Society, 78, 1434-1437 (1956), in dimethyl sulfoxide (1 L) were added trimethylammonium hydrazine iodide (106 g) and potassium t-butoxide (61.5 g). The mixture was stirred at room temperature for 2.5 hours, and then added to 1N hydrochloric acid. The resulting precipitate was collected by filtration to give a compound and the compound was dissolved in methanol (700 mL). After addition of 10% palladium carbon (8 g) to the solution, the mixture was stirred at room temperature overnight under a hydrogen atmosphere. The reaction mixture was filtered and the filtrate was concentrated in vacuo to give the title compound (25.9 g, 86%) as a brown solid.

Reference Example 3

Preparation of 2-phenyl-4,5-diaminopyrimidine

Zinc chloride (136 mg), potassium t-butoxide (505 mg) and O-methylhydroxylamine monohydrochloride (125 mg) were successively added to a solution of 2-phenyl-5-nitropyrimidine (201 mg, 1.00 mmol), which was prepared according to the method described in the Journal of American Chemical Society, 78, 1434-1437 (1956), in dimethyl sulfoxide (5 mL). The mixture was stirred at room temperature for 40 minutes, and saturated aqueous ammonium chloride was added thereto, then the mixture was extracted with ethyl acetate. The organic layer was washed with 5% aqueous sodium bicarbonate, dried over aqueous sodium sulfate, and concentrated in vacuo. The residue was dissolved in methanol (8 mL), and 10% palladium carbon (50 mg) was added thereto. The mixture was stirred at room temperature for one hour under a hydrogen atmosphere, and then filtered. The filtrate was concentrated in vacuo to give the title compound (148 mg, 80%) as a brown solid.

Reference Example 4

Preparation of 2,3-diamino-6-(2-fluorophenyl)pyridine (1) Preparation of 6-amino-2-bromo-5-nitropyridine To a solution of commercially available 2,6-dichloro-5-nitropyridine (20.0 g, 95.3 mmol) in ethanol (300 mL) was added aqueous ammonia (60 mL), and the mixture was stirred at room temperature for 10 hours. The resulting precipitate was filtered, washed with ethanol, and dried in vacuo to give 6-amino-2-chloro-5-nitropyridine (13.8 g, 83%). The compound thus obtained was suspended in an acetic acid solution (130 mL) of 30% hydrogen bromide. The suspension was stirred at 100° C. for 26 hours, cooled to room temperature, and concentrated in vacuo. The resulting residue was extracted with ethyl acetate. The organic layer was washed with saturated aqueous sodium bicarbonate and saturated brine, dried over anhydrous magnesium sulfate, and concentrated in vacuo. The residue thus obtained was recrystallized from ethyl acetate to give the title compound (14.93 g, 86%).

(2) Preparation of 2,3-diamino-6-(2-fluorophenyl)pyridine

To a solution of 6-amino-2-bromo-5-nitropyridine (2.0 g, 9.2 mmol) and 2-fluorophenylboronic acid (2.57 g, 18 mmol) in dimethoxyethane (60 mL) were added 2M aqueous sodium carbonate solution (18 mL) and tetrakistriphenylphosphine palladium(0) (106 mg, 0.092 mmol). The mixture was stirred at 105° C. for 16 hours under a nitrogen atmosphere. After the reaction mixture was cooled to room temperature, it was extracted with ethyl acetate. The organic layer was washed with saturated brine, dried over anhydrous magnesium sulfate, and concentrated in vacuo. The residue was dissolved in a mixture of ethyl acetate (30 mL) and methanol (30 mL). To the solution was added 10% palladium carbon (200 mg), and the mixture was stirred at room temperature for 14 hours under a hydrogen atmosphere. After removal of the palladium catalyst by filtration, the filtrate was concentrated in vacuo. The residue was purified by silica gel column chromatography (chloroform:methanol=30:1) to give the title compound (1.87 g, 100%) as a reddish brown oil.

$^1$HNMR (300 MHz, CD$_3$OD, δ ppm): 6.89-6.96 (2H, m), 7.06-7.12 (1H, m), 7.15-7.20 (1H, m), 7.25-7.30 (1H, m), 7.65-7.70 (1H, m); mass spectrum (ESI): 204 (M+H)

Reference Example 5

Preparation of 4,5-diamino-2-(4-fluorophenyl)pyrimidine (1) Preparation of 2-(4-fluorophenyl)-4,6-dihydroxy-5-nitropyrimidine 4,6-dihydroxy-2-(4-fluorophenyl)pyrimidine (11 g, 53 mmol) described in European patent No. 136976A was gradually added to fuming nitric acid (100 mL) at 0° C. The reaction temperature was raised to room temperature, and the mixture was stirred for 15 hours. The reaction mixture was poured onto ice-water (150 mL), and then neutralized with sodium carbonate at 0° C. The resulting precipitate was collected by filtration and dried to give the objective compound as a solid (9.2 g, 68%).

(2) Preparation of 4,6-dichloro-2-(4-fluorophenyl)-5-nitropyrimidine

Phosphorus oxychloride (17 mL) and N,N-dimethylaniline (4.21 mL) were added to 2-(4-fluorophenyl)-4,6-dihydroxy-5-nitropyrimidine (8.2 g, 32.6 mmol). The mixture was heated under reflux for 3 hours, cooled down to room temperature, and concentrated in vacuo to give a residue, to which was added ice-water. The resulting precipitate was collected by filtration, washed with water, and dried to give the objective compound as a solid (9.0 g, 96%).

(3) Preparation of 4-amino-6-chloro-2-(4-fluorophenyl)-5-nitropyrimidine

28% aqueous ammonia (3.1 mL) was added to a solution of 4,6-dichloro-2-(4-fluorophenyl)-5-nitropyrimidine (5.0 g, 17.4 mmol) in tetrahydrofuran (50 mL) at −50° C. until the starting material disappeared. After addition of 3N hydrochloric acid (5 mL) to the reaction solution at the same temperature, the reaction temperature was raised and then the mixture was concentrated in vacuo. Water was added to the residue, and the resulting suspension was filtered, then dried to give the objective compound as a solid (4.05 g, 87%).

(4) Preparation of 4,5-diamino-2-(4-fluorophenyl)pyrimidine 4-amino-6-chloro-2-(4-fluorophenyl)-5-nitropyrimidine (15.3 g, 57 mmol) was dissolved in a mixture of methanol (200 mL) and ethyl acetate (100 mL), and after adding thereto 10% palladium on carbon (2.88 g) and triethylamine (12 mL), the mixture was stirred in a hydrogen stream for 18 hours. The reaction mixture was filtered and the filtrate was concentrated in vacuo to give a residue, to which was added water. The mixture was extracted with ethyl acetate, and the organic layer was dried over anhydrous magnesium sulfate, then concentrated in vacuo. The residue was purified by silica gel column chromatography (C-300, chloroform:methanol=20: 1) to give the title compound as a brown solid (7.16 g, 68%).

$^1$HNMR (400 MHz, DMSO-d$_6$, δ ppm): 4.83 (2H, s), 6.36 (1H, s), 7.10-7.23 (2H, m), 7.64 (1H, s), 8.11-8.22 (2H, m); mass spectrum (ESI): 205 (M+H)

Reference Example 6

Preparation of 4,5-diamino-2-(2,5-difluoro-phenyl)-pyrimidine

Working up in the same manner as Reference Example 5, there was obtained the title compound (59.7 g) as a yellow solid from 3,5-dihydroxy-2-(2,5-difluorophenyl)pyrimidine (125 g).

Mass spectrum (ESI): 223 (M+H)

Formulation Example 1

20.0 g of the compound of Example 6, 417 g of lactose, 80 g of crystalline cellulose and 80 g of partial alpha-starch were blended with a V-cone blender. To the mixture was added 3.0 g of magnesium stearate, and the whole was blended. The blended powder was compressed into 3000 tablets by conventional procedure so that each tablet has a weight of 150 mg and a diameter of 7.0 mm.

| The content per one tablet(150 mg) | |
|---|---|
| The compound of Example 1 | 5.0 mg |
| Lactose | 104.25 mg |
| Crystalline cellulose | 20.0 mg |
| Partial alpha-starch | 20.0 mg |
| Magnesium stearate | 0.75 mg |

Formulation Example 2

10.8 g of hydroxypropylcellulose 2910 and 2.1 g of polyethylene glycol 6000 were dissolved in 172.5 g of purified water. To the solution was dispersed 2.1 g of titanium dioxide to provide a coating liquid. 2,500 tablets separately prepared according to Formulation Example 1 were subjected to spray-coating with the coating liquid using HICOATER-MINI to provide film coated tablets with a weight of 155 mg.

| The content per one tablet(155 mg) | |
|---|---|
| The tablet prepared in Formulation Example 1 | 150 mg |
| Hydroxypropylcellulose 2910 | 3.6 mg |
| Polyethylene glycol 6000 | 0.7 mg |
| Titanium dioxide | 0.7 mg |

INDUSTRIAL APPLICABILITY

Compounds of the present invention (I) exhibit NPY antagonistic effects, show excellent pharmacokinetics such as transport into brain or transport to cerebrospinal fluid, etc., and are very safe. Thus, the compound of the present invention (I) are useful as agents for the treatment of various diseases related to NPY, for example, cardiovascular disorders such as angina, acute or congestive heart failure, myocardial infarction, hypertension, nephropathy, electrolyte abnormality, vasospasm, arteriosclerosis, etc., central nervous system disorders such as bulimia, depression, anxiety, seizure, epilepsy, dementia, pain, alcoholism, drug withdrawal, circadian rhythm disorders, schizophrenia, memory impairment, sleep disorders, cognitive impairment, etc., metabolic diseases such as obesity, diabetes, hormone abnormality, hypercholesterolemia, hyperlipidemia, gout, fatty liver, etc., genital or reproductive disorders such as infertility, preterm labor, sexual dysfunction, etc., gastro-intestinal disorders, respiratory disorder, inflammatory diseases or glaucoma, and the like, also for example, atherosclerosis, hypogonadism, hyperandrogenism, polycystic ovary syndrome, hirsutism, gastro-intestinal motility disorder, obesity-related gastro-esophageal reflux, obesity hypoventilation (Pickwickian syndrome), sleep apnea, inflammation, systemic inflammation of the vasculature, osteoarthritis, insulin resistance, bronchoconstriction, alcohol preference, metabolic syndrome, Alzheimer's disease, cardiac hypertrophy, left ventricular hypertrophy, hypertriglyceridemia, low HDL cholesterol, cardiovascular disorders such as coronary heart disease (CHD), cerebrovascular disease, stroke, peripheral vascular disease, sudden death, gallbladder diseases, cancer (breast, endometrial, colon), breathlessness, hyperuricemia, impaired fertility, low back pain, or increased anesthetic risk, and the like.

The invention claimed is:

1. A compound of the formula (I),

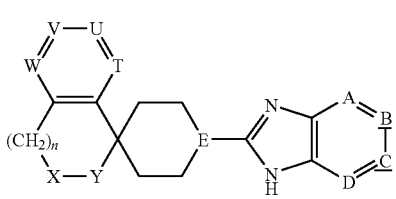

wherein A, and C are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and —Q$^1$—Ar$^1$, and at least one of A, and C is said methine group, and B and D are nitrogen;

Ar$^1$ is aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —Q$^2$—Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

E is methine or hydroxy substituted methine;

n is 0 or 1;

Q$^1$ and Q$^2$ are independently a single bond, oxygen, carbonyl or —N(R$^3$)—;

R$^1$ and R$^2$ are independently hydrogen or lower alkyl, or R$^1$ and R$^2$, taken together, form lower alkylene which may be intervened by oxygen, sulfur or imino;

R$^3$ is hydrogen or lower alkyl;

R$^4$ is lower alkyl, aralkyl or aryl;

R$^5$ and R$^8$ are independently hydrogen, lower alkyl, aralkyl or aryl;

R$^6$ and R$^7$ are independently hydrogen, hydroxy, lower alkyl, aralkyl or aryl;

T, U, V and W are independently methine or nitrogen, said methine being optionally substituted by a substituent selected from the group consisting of halogen, lower alkyl, halo-lower alkyl, hydroxy, lower alkoxy and halo-lower alkoxy, and at least two of T, U, V and W are said methine group;

X is —N(SO$_2$R$^4$)—, —N(COR$^5$)— or —CO—;

Y is —C(R$^6$)(R$^7$)—, —O— or —N(R$^8$)—, provided that the compound (I) when E is nitrogen, n is 0, X is —CO— and Y is —O— is excluded, and a pharmaceutically acceptable salt, ester or N-oxide derivative thereof.

2. The compound as claimed in claim 1, wherein n is 0, X is —N(SO$_2$R$^4$)— or —N(COR$^5$)— and Y is —C(R$^6$)(R$^7$)—, or X is —CO— and Y is —O— or —N(R$^8$)—; or a pharmaceutically acceptable salt thereof.

3. The compound as claimed in claim 1, wherein T, U, V and W are independently methine optionally substituted by halogen, lower alkyl, hydroxy or lower alkoxy; or a pharmaceutically acceptable salt thereof.

4. The compound as claimed in claim 1, wherein at least one of T, U, V and W is nitrogen; or a pharmaceutically acceptable salt thereof.

5. The compound as claimed in claim 1, wherein one of T, U, V and W is nitrogen, and one of the remainder is methine optionally substituted by halogen, lower alkyl, hydroxy or lower alkoxy; or a pharmaceutically acceptable salt thereof.

6. The compound as claimed in claim 1, wherein X is —CO— and Y is —O— or —NH—; or a pharmaceutically acceptable salt thereof.

7. The compound as claimed in claim 1, wherein X is —CO— and Y is —O—; or a pharmaceutically acceptable salt thereof.

8. The compound of the formula (I-a) as claimed in claim 1,

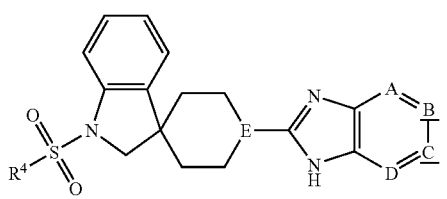

(I-a)

wherein A, and C are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and —Q$^1$—Ar$^1$, and at least one of A, and C is said methine group, and B and D are nitrogen;

Ar$^1$ is aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —Q$^2$—Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

E is methine or hydroxy substituted methine;

Q$^1$ and Q$^2$ are independently a single bond, oxygen, carbonyl or —N(R$^3$)—;

R$^1$ and R$^2$ are independently hydrogen or lower alkyl, or R$^1$ and R$^2$, taken together, form lower alkylene which may be intervened by oxygen, sulfur or imino;

R$^3$ is hydrogen or lower alkyl;

R$^4$ is hydrogen, lower alkyl, aralkyl or aryl;

or a pharmaceutically acceptable salt thereof.

9. The compound of the formula (I-b) as claimed in claim 1,

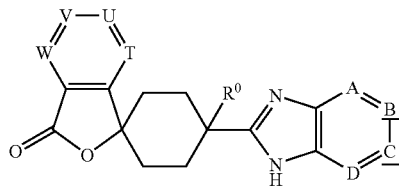

(I-b)

wherein A, and C are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and —Q$^1$—Ar$^1$, and at least one of A, and C is said methine group, and B and D are nitrogen;

Ar$^1$ is aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl and —Q$^2$—Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

Q$^1$ and Q$^2$ are independently a single bond, oxygen, carbonyl or —N(R$^3$)—;

R$^0$ is hydrogen or hydroxy;

R$^1$ and R$^2$ are independently hydrogen or lower alkyl, or R$^1$ and R$^2$, taken together, form lower alkylene which may be intervened by oxygen, sulfur or imino;

R$^3$ is hydrogen or lower alkyl;

T, U, V and W are independently methine or nitrogen, said methine being optionally substituted by a substituent selected from the group consisting of halogen, lower alkyl, halo-lower alkyl, hydroxy, lower alkoxy and halo-lower alkoxy, and at least two of T, U, V and W are said methine group;

or a pharmaceutically acceptable salt thereof.

10. The compound as claimed in claim 9, wherein each of T, U, V and W is unsubstituted methine; or a pharmaceutically acceptable salt thereof.

11. The compound as claimed in claim 9, wherein one of T, U, V and W is nitrogen; or a pharmaceutically acceptable salt thereof.

12. The compound as claimed in claim 9, wherein one of T, U, V and W is nitrogen, and one of the remainder is methine having a substituent selected from the group consisting of halogen, lower alkyl, hydroxy and lower alkoxy; or a pharmaceutically acceptable salt thereof.

13. The compound as claimed in claim 9, wherein one of T, U, V and W is nitrogen, and one of the remainder is methine having a substituent selected from the group consisting of fluorine and hydroxy; or a pharmaceutically acceptable salt thereof.

14. The compound of the formula (I-c) as claimed in claim 1,

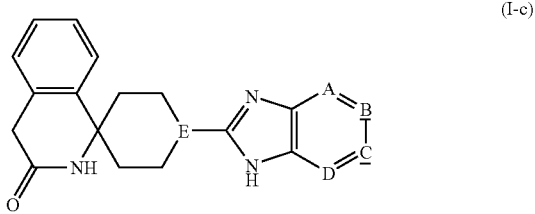

(I-c)

wherein A, and C are independently methine or nitrogen, said methine being optionally substituted by a substituent selected from the group consisting of halogen, cyano, lower alkyl, halo-lower alkyl, hydroxy, lower alkoxy, halo-lower alkoxy, lower alkoxycarbonyl, lower alkylsulfonyl, lower alkylsulfonyloxy, —N(R$^1$)R$^2$ and —Q$^1$—Ar$^1$, and at least one of A, and C is said methine group, and B and D are nitrogen;

Ar$^1$ is aryl or heteroaryl, any of which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —Q$^2$—Ar$^2$;

Ar$^2$ is aryl or heteroaryl, any of which is optionally substituted by a substituent selected from the group consisting of halogen, cyano, lower alkyl, halo-lower alkyl, hydroxy-lower alkyl, hydroxy, lower alkoxy, halo-lower alkoxy, lower alkylamino, di-lower alkylamino, lower alkanoyl and aryl;

E is methine or hydroxy substituted methine;

Q$^1$ and Q$^2$ are independently a single bond, oxygen, carbonyl or —N(R$^3$)—;

R$^1$ and R$^2$ are independently hydrogen or lower alkyl, or R$^1$ and R$^2$, taken together, form lower alkylene which may be intervened by oxygen, sulfur or imino; and R$^3$ is hydrogen or lower alkyl;

or a pharmaceutically acceptable salt thereof.

15. The compound as claimed in claim 1, wherein Ar$^1$ is phenyl which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —Q$^2$—Ar$^2$; or a pharmaceutically acceptable salt thereof.

16. The compound as claimed in claim 1, wherein Ar$^1$ is heteroaryl which is optionally substituted by a substituent selected from the group consisting of halogen, nitro, hydroxy, lower alkyl, halo-lower alkyl, hydroxy-lower alkyl, cyclo-lower alkyl, lower alkenyl, lower alkoxy, halo-lower alkoxy, lower alkylthio, lower alkylsulfonyl, carboxyl, lower alkanoyl, lower alkoxycarbonyl, lower alkanoylamino and —Q$^2$—Ar$^2$; or a pharmaceutically acceptable salt thereof.

17. The compound as claimed in claim 16, wherein the heteroaryl is pyridyl; or a pharmaceutically acceptable salt thereof.

18. The compound as claimed in claim 1, which is selected from the group consisting of (1) trans-2-(2-fluorophenyl)-8-[3'-oxospiro[cyclohexane-1,1'(3'H)-isobenzofuran]-4-yl]purine, (2) trans-2-(3-fluorophenyl)-8-[3'-oxospiro[cyclohexane-1,1'(3'H)-isobenzofuran]-4-yl]purine, (3) trans-2-(4-fluorophenyl)-8-[3'-oxospiro[cyclohexane-1,1'(3'H)-isobenzofuran]-4-yl]purine, (4) trans-2-(2-methoxyphenyl)-8-[3'-oxospiro[cyclohexane-1,1'(3'H)-isobenzofuran]-4-yl]purine, (5) trans-2-(4-methoxyphenyl)-8-[3'-oxospiro[cyclohexane-1,1'(3'H)-isobenzofuran]-4-yl]purine, (6) trans-2-(2-methylphenyl)-8-[3'-oxospiro[cyclohexane-1,1'(3'H)-isobenzofuran]-4-yl]purine, (7) trans-8-[3'-oxospiro[cyclohexane-1,1'(3'H)-isobenzofuran]-4-yl]-2-(2-trifluoro-methylphenyl)purine, (8) trans-2-(2-chloro-4-fluorophenyl)-8-[3'-oxospiro[cyclo-hexane-1,1'(3'H)-iso-benzofuran]-4-yl]purine, (9) trans-2-(2-hydroxymethylphenyl)-8-[3'-oxospiro[cyclo-hexane-1,1'(3'H)-iso-benzofuran]-4-yl]purine,

(10) trans-2-(2-furyl)-8-[3'-oxospiro[cyclohexane-1,1'(3'H)-isobenzofuran]-4-yl]purine,

(11) trans-8-[3'-oxospiro[cyclohexane-1,1'(3'H)-isobenzofuran]-4-yl]-2-(2-thienyl)purine,

(12) trans-8-[3'-oxospiro[cyclohexane-1,1'(3'H)-isobenzofuran]-4-yl]-2-(2-payroll)purine,

(13) trans-2-(3-fluoropyridin-6-yl)-8-[3'-oxospiro[cyclohexane-1,1'(3'H)-isobenzofuran]-4-yl]purine,

(14) trans-2-(2-chloropyridin-6-yl)-8-[3'-oxospiro[cyclohexane-1,1'(3'H)-isobenzofuran]-4-yl]purine,

(15) trans-2-(2-fluorophenoxy)-8-[3'-oxospiro[cyclohexane-1,1'(3'H)-isobenzofuran]-4-yl]purine,

(16) trans-2-(2,6-difluorophenoxy)-8-[3'-oxospiro[cyclo-hexane-1,1'(3'H)-isobenzofuran]-4-yl]purine,

(17) trans-8-[3'-oxospiro[cyclohexane-1,1'(3'H)-isobenzofuran]-4-yl]-2-(1-piperidyl)purine,

(18) trans-8-[3',4'-dihydro-3'-oxospiro[cyclohexane-1,1'(2'H)-isoquinolin]-4-yl]-2-phenylpurine,

(19) trans-8-[3',4'-dihydro-3'-oxospiro[cyclohexane-1,1'(2'H)-isoquinolin]-4-yl]-2-(2-fluorophenyl)purine, and

(20) trans-8-[3',4'-dihydro-3'-oxospiro[cyclohexane-1,1'(2'H)-isoquinolin]-4-yl]-2-(4-fluorophenyl)purine, or a pharmaceutically acceptable salt, ester or N-oxide derivative thereof.

19. The compound of claim 1, which is trans-8-[3'-oxospiro[cyclohexane-1,1'(3'H)-isobenzofuran]-4-yl]-2-phenylpurine; or a pharmaceutically acceptable salt thereof.

20. The compound of claim 1, which is trans-2-(2-fluorophenyl)-8-[3'-oxospiro[cyclohexane-1,1'(3'H)-isobenzofuran]-4-yl]purine; or a pharmaceutically acceptable salt thereof.

* * * * *